United States Patent [19]

Selsted et al.

[11] Patent Number: 5,840,498
[45] Date of Patent: Nov. 24, 1998

[54] ANTIBIOTIC CRYPTDIN PEPTIDES AND METHODS OF THEIR USE

[75] Inventors: Michael E. Selsted, Irvine, Calif.; Andre J. Ouellette, Lynn, Mass.

[73] Assignee: The Regents of the University of California, Alameda, Calif.

[21] Appl. No.: 482,279

[22] Filed: Jun. 7, 1995

Related U.S. Application Data

[63] Continuation of Ser. No. 342,268, Nov. 18, 1994, which is a continuation-in-part of Ser. No. 930,649, Aug. 14, 1992, Pat. No. 5,422,424, which is a continuation-in-part of Ser. No. 889,020, May 26, 1992, abandoned.

[51] Int. Cl.⁶ .................... G01N 33/53; G01N 33/542; G01N 33/537; G01N 33/543
[52] U.S. Cl. .................... 435/7.1; 530/387.1; 530/388.1; 530/387.9; 530/389.1; 435/4; 435/7.2; 435/7.21; 435/7.9; 435/7.91; 435/7.92; 435/7.93; 435/7.94; 435/7.95; 435/40.5; 435/40.52; 435/325; 435/326; 435/331; 436/518; 436/161; 436/162
[58] Field of Search .................... 530/387.1, 388.1, 530/389.9, 389.1; 435/4, 7.1, 7.2, 7.21, 7.9–7.95, 40.5, 40.52, 240.27, 960, 325, 326, 331; 436/518, 161, 162

[56] References Cited

U.S. PATENT DOCUMENTS

| | | | |
|---|---|---|---|
| 4,304,715 | 12/1981 | Hudson et al. | |
| 4,543,252 | 9/1985 | Lehrer et al. | 514/12 |
| 4,659,692 | 4/1987 | Lehrer et al. | 514/12 |
| 4,705,777 | 11/1987 | Lehrer et al. | 514/12 |
| 5,032,574 | 7/1991 | Wilde et al. | 514/12 |
| 5,191,015 | 3/1993 | Sheppard et al. | 525/54.1 |
| 5,459,235 | 10/1995 | Selsted et al. | 530/300 |

FOREIGN PATENT DOCUMENTS

| | | |
|---|---|---|
| WO93/24139 | 12/1993 | WIPO. |
| WO93/24513 | 12/1993 | WIPO. |

OTHER PUBLICATIONS

Campbell, Monoclonal Antibody Techonology, Elseiver Science Pub. pp. 1–32, 1986.
Panyutoch et al J. Immunological Methods vol. 141 p. 149, Aug. 1991.
Selsted, Michael A. "Enteric Defensins: Antibiotic Peptide Components of Intestinal Host Defense." *J. Cell. Biol.* 118:929–936 (1992).
Maurer, Paul H. and Callahan, Hugh J., "Proteins and Polypeptides as Antigens." *Methods in Ezymology* 70:49–70 (1980).
Eisenhauer, Patricia B. et al., "Cryptdins: Antimicrobial Defensins of the Murine Small Intestine." *Infection and Immunity* 60:3556–3565 (1992).
Ouellette, Andre J. et al., "Developmental Regulation of Cryptdin, a Corticostatin/Defensin Precursor mRNA in Mouse Small Intestinal Crypt Epithelium." *J. Cell. Biol.* 108:1687–1695 (1989)..

Ouellette, Andre J. et al., "Purification and Primary Structure of Murine Cryptdin-1, a Paneth Cell Defensin." *FEBS* 304:146–148 (1992).
Ouellette, Andre J. and Lualdi, John C., "A Novel Mouse Gene Family Coding for Cationic, Cysteine–rich Peptides." *J. Biol. Chem.* 265:9831–9837 (1990).
Ganz, Tomas et al., "Defensins." *Eur. J. Haematol.* 44:1–8 (1990).
Kagan, Bruce L. "Antimicrobial Defensin Peptides Form Voltage–Dependent Ion–Permeable Channels in Planar Lipid Bilayer Membranes." *Proc. Natl. Acad. Sci. USA* 87:210–214 (1990).
Ouellette, Andre J. et al., "Localization of the Cryptdin Locus on Mouse Chromosome 8." *Genomics* 5:233–239 (1989).
Wimley, William C. et al., "Interactions Between Human Defensins and Lipid Bilayers: Evidence for Formation of Multimeric Pores." *Protein Sci.* 3:1362–1373 (1994).
Selsted, Michael E., "Investigational Approaches for Studying the Structures and Biological Functions of Myeloid Antimicrobial Peptides." *Genetic Eng.* 15:131–147 (1993).
Huttner, Kenneth M. et al., "Structure and Diversity of the Murine Cryptdin Gene Family." *Genomics* 19:448–453 (1994).

(List continued on next page.)

*Primary Examiner*—Sheela Huff
*Attorney, Agent, or Firm*—Campbell & Flores LLP

[57] ABSTRACT

The present invention provides substantially purified cryptdin peptides having a consensus amino acid sequence:

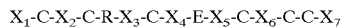

$$X_1\text{-C-}X_2\text{-C-R-}X_3\text{-C-}X_4\text{-E-}X_5\text{-C-}X_6\text{-C-C-}X_7$$

wherein $X_1$ is 3 to 9 amino acids; $X_2$ is one amino acid, preferably Y, H or R; $X_3$ is 2 or 3 amino acids; $X_4$ is three amino acids; $X_5$ is five amino acids; $X_6$ is 6 to 10 amino acids; and $X_7$ is 0 to 9 amino acids. The invention also provides a substantially purified mouse cryptdin having a consensus amino acid sequence:

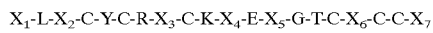

$$X_1\text{-L-}X_2\text{-C-Y-C-R-}X_3\text{-C-K-}X_4\text{-E-}X_5\text{-G-T-C-}X_6\text{-C-C-}X_7$$

wherein $X_1$ is 3 or 4 amino acids, preferably LRD, LSKK (SEQ ID NO: 1) or LRG; $X_2$ is 1 amino acid, preferably V, L or I; $X_3$ is 3 amino acids, preferably KGH or *RG, where * is S, T, K, I or A; $X_4$ is 2 amino acids, preferably GR, RR or RG; $X_5$ is 3 amino acids, preferably RMN, RVR, RVF HMN or HIN; $X_6$ is 6 to 9 amino acids, preferably GIRFLY (SEQ ID NO: 2) or RNLFLTFVF (SEQ ID NO: 3), RRGHLMYTL (SEQ ID NO: 4) or RKGHL*YT* (SEQ ID NO: 5), where * independently is L or M; and $X_7$ is 0 to 3 amino acids, preferably R, S or PRR. The invention also provides cryptdin analogs, which are devoid of one or more amino acids N-terminal to the first cysteine. In addition, the invention provides nucleic acid molecules encoding cryptdin peptides. The invention further provides methods for detecting inflammatory pathologies in a subject and for treating an inflammatory pathology in a subject by administering a pharmaceutical composition containing a cryptdin peptide.

6 Claims, 27 Drawing Sheets

OTHER PUBLICATIONS

Ouellette, Andre J. et al., "Mouse Paneth Cell Defensins: Primary Structures and Antibacterial Activities of Numerous Cryptdin Isoforms." *Infect. and Immun.* 62:5040–5047 (1994).

Aley, Stephen B. et al., "Killing of *Giardia Lamblia* by Cryptdins and Cationic Neutrophil Peptides." *Infect. and Immun.* 62:5397–5403 (1994).

Miller, S.I. et al., "Purification and Characterization of a Secreted Paneth Cell Defensin Using phoP Mutants of *Salmonella Typhimurium*." *ASCB/EMBO Summer Conference.* (1991). Abstract.

Chow, M.–S. et al., "Fmoc Solid Phase Peptide Synthesis of Defensins." *Proceeding of the Sixth Symposium of The Protein Society.* (1992). Abstract.

Notification of Transmittal of International Search Report for PCT/US95/13328 mailed 21 Feb. 1996.

FIG. 8

```
RAT CRYPT-1               LKQCHCRKF  CRPYEKAEGSCRPGLFIKRKICCIQQWTPGRT
RAT CRYPT-2      IGRPVRRCRCRAN  CGPKEYATAFCAQGPFKQFKFCCT
RAT CRYPT-3      IRWPWKRCHCRSF  CRPYENATSFCAQGLFKQHKFCCLDTWPPRMK

HUMAN HD-5  TSGSQARATCYCRTGRCATRESLSGVCEISGRL  YRLCCR
HUMAN HD-6              AFTCHCRR-SCYSTEYSYGTCTVMGIN  HRFCCL

Def CONSENSUS        CxCRxxxxCxxxxERxxGxCxxxxxxxxxCC
```

```
                                   25                  50
                        1
RAT CRYPT-1 (cDNA)      MKTLVLLLSALVLLAFQVQADPIQEAEEETKTEEQPADEDQDVSVSFEGPE
RAT CRYPT-2 (genomic)   MKTLVLLLSALVLVAYQVQADPIQGAEEETKTEEQPSDEDQDVSVSFEGPE
RAT CRYPT-3 (cDNA)      MKTLVLLLSALVLLAFQIQADPIQEAEEETKTEEQPADEDQDVSVSFEGPE 75                  100
                       51
RAT CRYPT-1            PSALQNLEIGWPLKQCHCRKFCRPYEKAEGSCRPGLFIKRKICCIQQWTPGRT
RAT CRYPT-2            ASALQDFEIGRPVRRCRCRANCGPKEYATAFCAQGPFKQFKFCCT
RAT CRYPT-3            PSALQNLEIRWPWKRCHCRSFCRPYENATSFCAQGLFKQHKFCCLDTWPPRMK
```

FIG. 9A

|  | <---SIGNAL PEPTIDE---><----------- Exon 1 -----------><---------- PROPIECE ----------><------ Exon 2 ------><---- CRYPTDIN ----> |
|---|---|
|  | 1                                                                                         58                                         93 |
| Cryp01 | MKTLVLLSAL VLLAFQVQAD PIQNTDEETK TEEQPGEDDQ AVSVSFGDPE GTSLQEES LRDLVCYCRS RGCKGRERMN GTCRKGHLLY TLCCR |
| Cryp02 | MKTLILLSAL VLLAFQVQAD PIQNTDEETK TEKQPGEEDQ AVSVSFGDPE GSSLQEES LRDLVCYCRT RGCKRRERMN GTCRKGHLMY TLCCR |
| Cryp03 | MKTLVLLSAL VLLAFQVQAD PIQNTDEETK TEEQPGEDDQ AVSVSFGDPE GSSLQEES LRDLVCYCRK RGCKRRERMN GTCRKGHLMY TLCCR |
| Cryp04 | ...LVLLSAL VLLAFQVQAD PIQNTDEETK TEEQPGEEDQ AVSISFGGQE GSALHEKS LRGLLCYCRK GHCKRGERVR GTC**G*IRF LYCCPRR |
| Cryp05 | MKTFVLLSAL VLLAFQVQAD PIHKTDEETN TEEQPGEEDQ AVSISFGGQE GSALHEE LSKKLICYCRI RGCKRRERVF GTCRNLFLTF VFCCS |
| Cryp06 | MKTLVLLSAL VLLAFQVQAD PIQNTDEETK TEEQPGEEDQ AVSVSFGDPE GTSLQEES LRDLVCYCRA RGCKGRERMN GTCRKGHLLY MLCCR |
| Cryp07 | MKTLILLSAL VLLAFQVQAD PIQNTDEETK TEEQPGEDDQ AVSVSFGDPE GSSLQEES LRDLVCYCRT RGCKRREHMN GTCRKGHLMY TLCCR |
| Cryp08 | MKTLVLLSAL VLLAFQVQAD PIQNTDEETK TEEQPGEEDQ AVSVSFGDPE GSSLQEES LRDLVCYCRK RGCKRREHMN GTCRKGHLMY TLCCR |
| Cryp09 | .........  .LAFQVQAD PIQNTDEETK TEEQPGEDDQ AVSVSFGDPE GSSLQEES LRDLVCYCRK RGCKRREHMN GTCRKGHLMY TLCCR |
| Cryp10 | .KTLVLLSAL VLLAFQVQAD PIQNTDEETK TEEQPGEEDQ AVSVSFGDPE GSSLQEES LRDLVCYCRK RGCKRERMN GTCRKGHLLY TLCCR |
| Cryp11 | .......AL VLLAFQVQAD PIQNTDEETK TEEQPGEEDQ AVSVSFGDPE GTSLQEES LRDLVCYCRS RGCKGRERMN GTCRKGHLLY MLCCR |
| Cryp12 | MKTLILLSAL VLLAFQVQAD PIQNTDEETK TEEQPGEEDQ AVSVSFGDPE GTSLQEES LRDLVCYCRA RGCKGRERMN GTCRKGHLLY TLCCR |
| Cryp13 | MKTLVLLSAL VLLAFQVQAD PIQNTDEETK TEEQPGEEDQ AVSVSFGDPE GTSLQEES LRDLVCYCRK RGCKRRERMN GTCRRGHLMY TLCCR |
| Cryp14 | .......AL VLLAFQVQAD PIQNTDEETK TEEQPGEEDQ AVSVSFGDPE GSSLQEES LRDLVCYCRT RGCKRRERMN GTCRKGHLMH TLCCR |
| Cryp15 | MKTLVLLSAL VLLAFQVQAD PIQNTDEETK TEEQPGEEDQ AVSVSFGDPE GSSLQEES LRDLVCYCRI RGCKRREHIN GTCRKGHLLY MLCCR |
| Cryp16 | MKTLILLSAL VLLAFQVQAD PIQNTDEETK TEEQPGEEDQ AVSVSFGDPE GTSLQEES LRDLVCYCRS RGCKGRERMN GTCRKGHLMY TLCCR |
| Cryp17 | ........  .LLAFQVQAD PIQNTDEETK TEEQPGEEDQ AVSVSFGDPE GTSLQEES LRDLVCYCRK RGCKRREHMN GTCRKGHLLY TLCCR |

FIG. 9B

| | MKTLVLLSAL | VLLAFQVQAD | PIQNTDEETK | TEEQPGEDDQ | AVSVSFGDPE | GTSLQEES | LRDLVCYCRS | RGCKGRERMN | GTCRKGHLLY | TLCCR |
|---|---|---|---|---|---|---|---|---|---|---|
| Cryp01 | .......... | .......... | .......... | .......... | .......... | ........ | .......... | .......... | .......... | ..... |
| Cryp02 | ....I..... | .......... | .......... | ..K....E.. | .......... | .S...... | .......... | ...T...R.. | .......... | ...M. |
| Cryp03 | .......... | .......... | .......... | .......... | .......... | .S...... | .......... | ......R... | .......... | ...M. |
| Cryp04 | .......... | .......... | .......... | .......... | ....I..GQ. | SA.H.K.. | .G.L....K  | GH..RG..VR | ...**.*IRF | LY..PRR |
| Cryp05 | ....F..... | .......... | ..HK.....N | .......... | ....I..GQ. | SA.H.... | LSKK.I...I | ....R...VF | ....NLF.TF | VF..S |
| Cryp06 | .......... | .......... | .......... | .......... | .......... | ........ | .......A.. | .......... | .......... | ...M.. |
| Cryp07 | ....I..... | .......... | .......... | .......... | .......... | .S...... | .......... | ...T...R.H | .......... | ...M. |
| Cryp09 | .......... | .......... | .......... | .......E.. | .......... | .S...... | .......K.. | .......R.H | .......... | ...M. |
| Cryp08 | .......... | .......... | .......... | .......E.. | .......... | .S...... | .......K.. | .......R.H | .......... | ...M. |
| Cryp10 | .......... | .......... | .......... | .......... | .......... | ........ | .......K.. | .......R.H | .......... | ...M. |
| Cryp11 | .......... | .......... | .......... | .......E.. | .......... | ........ | .......A.. | .......... | .......... | ..... |
| Cryp12 | ....I..... | .......... | .......... | .......E.. | .......... | ........ | .......K.. | .......R.H | .......... | ...M. |
| Cryp13 | .......... | .......... | .......... | .......E.. | .......... | ........ | .......K.. | .......R.. | .......R.. | ..... |
| Cryp14 | .......... | .......... | .......... | .......E.. | .......... | .S...... | .......T.. | .......R.. | .......... | ..MH. |
| Cryp15 | .......... | .......... | .......... | .......E.. | .......... | .S...... | .......K.. | .......R.HI | .......... | ...M. |
| Cryp16 | ....T..... | .......... | .......... | .......... | .......... | ........ | .......... | .......... | .......... | ..... |
| Cryp17 | .......... | .......... | .......... | .......E.. | .......... | ........ | .......K.. | .......R.H | .......... | ..... |

FIG. 10(a)

```
                                                              MetLysThrLeuVallLeuLeuSerAlaLeuValLeuVallLeuLeuAlaPheGlnValAla
Cryptdin-1
Codon:                                                         1                    10                    20
Cryp01      acacattgagctcctgctcaccaatcctccaggtgactcccagccATGAAGACACTAGTCCTCCTCTCTGCCCTTGTCCTGCTGGCCTTCCAGGTCCAGG
Base        -40       -30       -20       -10       +1        1         10        20        30        40        50
Cryp01      ......T..A...C..G........................................................T.....................
Cryp02      ......C..A..CG..A.......................A.......................C..............................
Cryp03      ......T..G...C..G.......................................................C.....................
Cryp04      ..............................................................................C..............
Cryp05      ......T..G...C..G...........T...................C........T.T...................................
Cryp06      ......C..A...G..A.......................A.......................C..............................
Cryp07      ......C..A...G..A.......................A.......................C..............................
Cryp08      ..............................................................................................
Cryp09      ..............................................................................C..............
Cryp10      ..............................................................................C..............
Cryp11      ..............................................................................C..............
Cryp12      ......T..G...C..G...............................................................C..............
Cryp13      ..............................................................................T..............
Cryp14      ..............................................................................C..............
Cryp15      ..............................................................................T..............
Cryp16      .....................................CA......................A................C..............
Cryp17      ..............................................................................................
Consensus   acaca-tg-gct-ct-ctcaccaatcctccaggtgactcccagccATGAAGACACTAGTCCTCCTCTCTGCCCT-GTCCTGCTGGCCTGGCCTTCCAGGTCCAGG
```

FIG. 10(b)

```
Cryptdin-1  AspProIleGlnAsnThrAspGluGluThrLysThrGluGluGlnProGlyGluAspAspGlnAlaValSerValSerPheGlyAspProGluGlyThr
Codon:           20                    30                    40                    50
Cryp01      CTGATCCTATCCAAAACACAGATGAAGAGACTAAAACTGAGGAGCAGCCAGGGGAAGACAGCCAGGAAGACGACCAGGCCGTATCTGTCTCCTTTGGAGACCCAGAAGGCAC
Base             60        70        80        90        100       110       120       130       140       150
Cryp01      ..........................................................................................................A.
Cryp02      ..................T..................................................................................T.
Cryp03      ...........................................................C........................................T.
Cryp04      ..................T..................................................G...............A..C..........G..A....GT.
Cryp05      ..................C.A..............................T................G...............A..C..........G..A....GT.
Cryp06      ..................T...................................................G....................................A.
Cryp07      ......................................................................C..............................T.
Cryp08      ...........................................................C........................................T.
Cryp09      ......................................................................G..............................T.
Cryp10      ......................................................................C..............................T.
Cryp11      ......................................................................C..............................A.
Cryp12      ......................................................................G..............................A.
Cryp13      ...................................................A................G.........C..A...................T.
Cryp14      ......................................................................G.............................T.
Cryp15      ......................................................................C.............................T.
Cryp16      ...................................................A................G.........C..A...................A.
Cryp17      ..................T..................................A...............G.........C..A...................A.

Consensus   CTGATCCTATCCAAAACACAGATGAAGAGACTAAAACTGAGGAGCAGCCAGGGGAAGA·GACCAGGCTGTGTCTGTGTCTCTTTTGGAGACCAGAAGGC·C
```

```
Cryptdin-1  LeuLeuTyrThrLeuCysCysArgEnd
Codon:                   90        ***
Cryp01     TTATTG.ACACGCTCTGCTGTCGCTGAacatggagaccacagaggacaagacgaacatgagtactgaggccactgatgctggtgcctgatgaccacttcg
Base          260       270       280       290       300       310       320       330       340       350
Cryp01     ...T......C...................................A......G......CG.A..........................................
Cryp02     ...A......C...................................A......G......TG.C..........................................
Cryp03     ...A.....CA...................................A......G......CG.A..........................................C..G
Cryp04     .GTAC.G.TGC.C.C..C.CT.AAC.TGCA.AT..AAAGATATGAC.ACCATTGTCTCTG.GGCC.CTG.TGCCG.GGCC..ATGACCACTTCTCAA...........
Cryp05     ..ACT.T.GTAT........CA......T..C..TGA..A..ATATGACAACCATC.GC.CTGAG.C.ACTGATGCTG..GT.TGATGAT.AC..CGC..........
Cryp06     ...T......T..................................T......A......CG.C..........................................
Cryp07     ...A......T..................................T......A......CG.C..........................................
Cryp08     ...A......C..................................A......G......CA.G..........................................
Cryp09     ...T......T..................................A......G......TG.A..........................................
Cryp10     ...T......C..................................A......G......CG.A..........................................
Cryp11     ...T......T..................................A......A......CG.C..........................................
Cryp12     ...A......C..................................T......A......CG.C..........................................
Cryp13     ...A......CA..................................A......G......CG.A..........................................C..G
Cryp14     ...A.C....C..................................A......G......CA.G..........................................
Cryp15     ...T......T..................................A......G......TG.C..........................................
Cryp16     ...A......C..................................T......A......CG.C..........................................CG*
Cryp17     ...T......T.........T........................A......G......T.C..........................................C..G
Consensus  TTA-TGTACA-GCTCTGCTGTCCT.CGCTGAacatggagacc-cagag-acaaga--a-catgagtactgaggccactgatgctggtgcctgatgaccacttct
```

FIG. 10(e)

```
Cryp01    cataaattgttcgcaatatgc(A)n
Base                360       370
Cryp01    ....................................
Cryp02    .........C.T........................
Cryp03    ....................................
Cryp04    A....-GT...CAATATGC.................
Cryp05    A.TA..T.GT.CGCA.TATG.................
Cryp06    .....C..............................
Cryp07    ....................................
Cryp08    ....................................
Cryp09    ....................................
Cryp10    ....................................
Cryp11    ........C...........................
Cryp12    ....................................
Cryp13    ....................................
Cryp14    ..................A.................
Cryp15    ....................................
Cryp16    ....................................
Cryp17    .........C.T........................
Consensus caataaattgttcgcaatatgc
```

RAT CRYPTIN 1 cDNA SEQUENCE

```
10         20         30         40         50
1234567890 1234567890 1234567890 1234567890 1234567890
ACACTGGTCT CCAGCTCACC AATCCTCCAG GTGACTTCCA GCCATGAAGA    50
CTCTTGTCCT CCTCTCTGCC CTTGTCCTGC TGGCATTCCA GGTCCAGGCT   100
GATCCCATTC AAGAGGCAGA AGAAGAGACT AAAACTGAGG AGCAGCCAGC   150
AGATGAGGAC CAGGATGTGT CTGTCTCCTT TGAAGGCCCA GAACCCTCTG   200
CTCTTCAAAA TTTAGAGATA GGATGGCCAT TAAAGCAGTG CCATTGCCGA   250
AAGTTCTGCA GACCTTATGA AAAGGCCGAG GGGTCCTGTC GTCCAGGTCT   300
ATTTATAAAA CGCAAAATCT GCTGCATACA ACAATGGACA CCAGGGAGGA   350
CATAACCACG TGAACTGGGA CCTCACAATC TGTCATTCTT GGGCTTCAAC   400
TCGACTGCTT TTCCTTCTCC AATAAACCCC TTGCAGACAA AAAAA        445
```

FIG. 14B

RAT CRYPTIN 2 cDNA SEQUENCE

```
10         20         30         40         50
1234567890 1234567890 1234567890 1234567890 1234567890
ACACTGGTCT CCAGCTCACC AATCCTCCAG GTGACTTCCA GCCATGAAGA    50
CTCTTGTCCT CCTCTCTGCC CTTGTCCTGG TGGCCTACCA GGTCCAGGCT   100
GATCCCATTC AAGGGGCAGA AGAAGAGACT AAAACTGAAG AGCAACCATC   150
AGATGAGGAC CAGGATGTGT CTGTCTCCTT TGAAGGCCCA GAAGCCTCTG   200
CTCTTCAAGA TTTTGAGATA GGAAGGCCAG TGAGGAGGTG CCGTTGCAGA   250
GCAAACTGCG GACCTAAAGA ATATGCCACT GCGTTCTGTG CTCAAGGTCC   300
ATTTAAACAG TTCAAATTCT GCTGCACATG AACATGGATC CCAAGTCTGA   350
GATAACCACG TGCTCTGGGA CCTCACAATC TGTCATTATT GTGCTTGACC   400
TCAACTGCTT TTCCTTCTCC AATAAACTCC TGGCAGACAA AAAAA        445
```

FIG. 14C

RAT CRYPTIN 3 cDNA SEQUENCE

```
10         20         30         40         50
1234567890 1234567890 1234567890 1234567890 1234567890
ACACTGGTCT CCAGCTCACC AATCCTCCAG GTGACTTCCA GCCATGAAGA    50
CTCTTGTCCT CCTCTCTGCC CTTGTCCTGC TGGCATTCCA GATCCAGGCT   100
GATCCCATTC AAGAGGCAGA AGAAGAGACT AAAACTGAGG AGCAGCCAGC   150
AGATGAGGAC CAGGATGTGT CTGTCTCCTT TGAAGGCCCA GAACCCTCTG   200
CTCTTCAAAA TTTAGAGATC AGATGGCCAT GGAAGAGGTG CCATTGCAGA   250
AGTTTCTGCA GACCTTATGA AAATCGGACT TCGTTCTGTG CTCAAGGTCT   300
ATTTAAACAA CACAAATTCT GCTGCCTAGA AACATGGCCC CCAAGGATGA   350
AATAACCACG TGCTCTGGGA CCTCACAATC TGTCATCATT GTGCTTGGCC   400
TCAACTTCTT TTCCTTCTCC AATAAACTCC TTGCAGACAA AAAAA        445
```

FIG. 15A(1)

RAT CRYPTIN 1 GENOMIC SEQUENCE

| 10 | 20 | 30 | 40 | 50 | |
|---|---|---|---|---|---|
| 1234567890 | 1234567890 | 1234567890 | 1234567890 | 1234567890 | |
| CCTGAGACCA | ACTCTGTGAT | AATCAGAAAA | GTCAATAATG | TGTCTGAAAT | 50 |
| GTAAGGTGTG | CTTCTTGACT | GATAGTTCTA | AGCCTACAGA | GAGATTCATG | 100 |
| TGGTCATATC | CCATTTAACA | ATGATATATA | TGTTAAATAT | ATAAAGATAT | 150 |
| ATGTATGTTC | AGTATGTATG | TTCAATATGT | ATGTAAATAA | TATTCTTGCT | 200 |
| GCTTCACTAG | CTTTTACACA | GAGCTGTAAG | TAAAAACATT | GTAGCCAATG | 250 |
| AATAGTATTT | ATTAACATGT | AAATAGGAGC | TGGCACCTGT | GACAGTGGGA | 300 |
| CTCCATACAC | TGACTGTAAA | CAACAGGATG | CTCTGGACCT | TTTGCTGTGT | 350 |
| GTGTGGTGAG | AGACATGGGA | TAAACACAGA | CTGAAGAGTG | TTCCTGAATG | 400 |
| ACATGGCGGC | ACTTCTCGAG | ACCGGGTAGC | AGCTTCTGAG | CCTCTCTACA | 450 |
| TTGTGGATGT | CCTTTCCTGT | AGGTCAGGTC | TCATTGTCTA | AAAGTAAAAG | 500 |
| CATTGCAGCA | TCTCAGACCT | GGGAAACACC | CCATGGCTTG | AGGGTCCTGA | 550 |
| GCATGAAGAG | CCACCTGGAG | CTCACTCTTG | GCAGATGTGT | TCCATGACTT | 600 |
| TGGCTTCTTC | AGAACAACCC | ACTACAGCTT | CACTCTGACA | AATCCTAGAA | 650 |
| ACTTGAACTC | AATTCACTAG | AGGGCACCAT | AAAGCCATCA | TACCTTATAA | 700 |
| TGGCCCCAAA | GGAGGTGATT | CACAAAGTTT | GCCTTGATGA | GGACAATTGC | 750 |
| TAATACACAA | AAACTTGCAA | AAAAAAATTG | AGTGTCCAGT | CCACCTGGTC | 800 |
| AAGGACTGGT | CCCGGATCCA | CAGTTTCTGA | GAATAGCAGG | CTCTAACTTG | 850 |
| AAAACACAAA | AATTGTTTGT | TCTATGAGCT | CATTAAATTA | GGCAGTGTTC | 900 |
| AGCTATTTTC | TTTCCTGACC | ACTGAGAGGT | AAATACTCAA | GCAGATGGGA | 950 |
| AACAGGGGAG | GACAGTAAAG | CCTGTTCATC | ATTATCAGTG | GGAGTGTGCA | 1000 |
| TGAGGGGAGG | GGTGTCAGTG | AACACACAGA | GCATCAGGAA | GGAAGCCTTG | 1050 |
| AGGACAGAGG | AACATCAAAG | GGATCCTGAG | GACAACAGCT | GGGAGCAGTT | 1100 |
| GCCATCAATG | AGTGCCTTCT | CTAAGTATGG | GGCATGTTCT | TTGCCCTATA | 1150 |
| AATGCAGGCT | GGCTTCTCTC | TCCACACACT | GGTCTCCAGC | TCACCAATCC | 1200 |
| TCCAGGTGAC | TTCCAGCCAT | GAAGACTCTT | GTCCTCCTCT | CTGCCCTTGT | 1250 |
| CCTGCTGGCA | TTCCAGGTCC | AGGCTGATCC | CATTCAAGAG | GCAGAAGAAG | 1300 |
| AGACTAAAAC | TGAGGAGCAG | CCAGCAGATG | AGGACCAGGA | TGTGTCTGTC | 1350 |
| TCCTTTGAAG | GCCCAGAACC | CTCTGCTCTT | CAAAATTTAG | GTGCGTGCTT | 1400 |
| GTGCACAGAA | TGATGGAGGC | TTGGAGTCTC | CTGATGGAGG | GTTGTAGATT | 1450 |
| AGCCCTGGAG | TCCTGTCAAG | GACAGTCTGG | TTCAGGTAGC | TGTCTACTGA | 1500 |
| TCCTTTCAGA | ACTTCCCTGT | CTTATTCATA | GAAATAACAG | TGAGAGACAA | 1550 |
| GCCATTGGGC | TTGACTTTTT | CCTTTTAAGA | TTTCGGTCTA | ACAATTTATC | 1600 |
| TGTGAAAAAC | CTTTAAAATA | TAAAACATAT | TGATTAGTTC | TTTAAACCTG | 1650 |
| AGTGATAATT | TTCTTACAGG | AAGAAATATC | CGTTTTACCC | TAAAAATTAG | 1700 |
| ATTGGTACCC | AAATGCCAGT | GTATGAAGGT | GTTGGGTCAA | GAAAACACAA | 1750 |
| AAAAACTGTT | AGAATATGGT | GTAGATGAAA | ATTCCTATAT | GTGATTAACA | 1800 |
| CTTGTTAAAC | ATCTTATCTC | CATGTGTTTG | GGGTTGATCA | CTGTGCTGGC | 1850 |
| TGTGATGTCA | CCCACACAGC | AAACCTACTC | TCTACCATGC | ACAGGACATC | 1900 |

FIG. 15A(2)

RAT CRYPTIN 1 GENOMIC SEQUENCE

| 10 | 20 | 30 | 40 | 50 | |
|---|---|---|---|---|---|
| 1234567890 | 1234567890 | 1234567890 | 1234567890 | 1234567890 | |
| TTCATGGGGT | AGTTCACTGT | TACACACTAC | TGGCCTCCTT | ACTTCATGCC | 1950 |
| TGATGCTTTC | TTGTTTCCTC | AGAGATAGGA | TGGCCATTAA | AGCAGTGCCA | 2000 |
| TTGCCGAAAG | TTCTGCAGAC | CTTATGAAAA | GGCCGAGGGG | TCCTGTCGTC | 2050 |
| CAGGTCTATT | TATAAAACGC | AAAATCTGCT | GCATACAACA | ATGGACACCA | 2100 |
| GGGAGGACAT | AACCACGTGA | ACTGGGACCT | CACAATCTGT | CATTCTTGGG | 2150 |
| CTTCAACTCG | ACTGCTTTTC | CTTCTCCAAT | AAACCCCTTG | CAGACAAATA | 2200 |
| ACCTGTTTAT | GTTTTTTTGA | TGCTTTCTAT | GTGGCGTAGA | CAGGACTCTC | 2250 |
| CTGAGCCATG | TAGCAAAATC | TTCAGTGAAT | CCTTTGTAAA | AGAAGTCTTG | 2300 |
| GTCACATTTC | AGCAGTCATA | TCAAGGATGA | GCAGGAGGTT | AGATCCAAAG | 2350 |
| AGACAAGATG | GTCTGCGCCA | GCTGCTTCTG | TGTCTATCAA | GTCTTCTGTC | 2400 |
| CTTTAGATTA | GAGTCACCCT | CAAAAATTAG | TTCCAGATTT | TCATGTTCTA | 2450 |
| TTTTTTC | | | | | 2457 |

FIG. 15B(1)

RAT CRYPTIN 2 GENOMIC SEQUENCE

| 10 | 20 | 30 | 40 | 50 | |
|---|---|---|---|---|---|
| 1234567890 | 1234567890 | 1234567890 | 1234567890 | 1234567890 | |
| TATTACGAAT | TCGAGCTCGG | TACCGGTATA | TGAAGAGCGA | CCACTGCCAG | 50 |
| GACGAAAGTG | CAATGCGGCA | TACCTCAGTG | GCGTGGAGTG | CAGGTATACA | 100 |
| GATTAATCCG | GCAGCGTCCG | TCGTTGTTGA | TATTGCTTAT | GAAGGCTCCG | 150 |
| GCAGTGGCGA | CTGGCGTACT | GACGGATTCA | TCGTTGGGGT | CGGTTATAAA | 200 |
| TTCTGATTAG | CCAGGTAACA | CAGTGTTATG | ACAGCCCGCC | GGAACCGGTG | 250 |
| GGCTTTTTTG | TGGGGTGAAT | ATGGCAGTAA | AGATTTCAGG | AGTCCTGAAA | 300 |
| GACGGCACAG | GAAAACCGGT | ACAGAACTGC | ACCATTCAGC | TGAAAGCCAG | 350 |
| ACGTAACAGC | ACCACGGTGG | TGGTGAACAC | GGTGGGCTCA | GAGAATCCGG | 400 |
| ATGAAGCCTG | CTTTTTTATA | CTAAGTTGGC | ATTATAAAAA | AGCATTGCTT | 450 |
| ATCAATTTGT | TGCAACGAAC | AGGTCACTAT | CAGTCAAAAT | AAAATCATTA | 500 |
| TTTGATTTCA | ATTTTGTCCC | ACTCCCTGCC | TCTGTCATCA | CGATACTGTG | 550 |
| ATGCCATGGT | GTCCGACTTA | TGCCCGAGAA | GATGTTGAGC | AAACTTATCG | 600 |
| CTTATCTGCT | TCTCATAGAG | TCTTGCAGAC | AAACTGCGCA | ACTCGTGAAA | 650 |
| GGTAGGCGGA | TCTGGGTCGA | CTCTAGGCCT | CACTGGCCTA | ATACGACTCA | 700 |
| CTATAGGGAG | CTCGAGGATC | ATTGCTAATA | CCATGAAACT | TGACCACCTG | 750 |
| GTCAAGGACT | GGTCCAGGGT | CCACAGTTTC | TGAGAAGAGC | AGGCTCCAAC | 800 |
| TTCTAACCAC | AAAAACTATT | TTTTCCATGC | GCTCCTTAAA | TTAGGCAGCG | 850 |
| CCCAGCTATT | TTCTTTCCTG | ACCACTGAGA | GGTAAATACT | CAAGCAGATG | 900 |
| GGAAACAGGG | GAAGATAGCA | AGGCCTCTTC | ATCATTATCA | CTGGGTGTGT | 950 |
| GCGTGAGGGG | AGGGGTGTCA | TTGCATACAC | AGGGCAACAT | CAGGATGGAA | 1000 |
| GCCTTGAGGA | CAGAGGAACA | TCAAAGGGAT | CCTGAGGACA | ACAGCTGGGA | 1050 |
| GCAGTTGCCA | TCAGTGAGTG | CCTTCTCTAA | GTGTGGGGCC | TTTCTCTGCC | 1100 |
| ACATAAATGC | AGGCTGCCTC | CTCTCTCCAC | ACACTGGTCT | CCAGCTCACC | 1150 |
| AATCCTCCAG | GTGACTTCCA | GCCATGAAGA | CTCTTGTCCT | CCTCTCTGCC | 1200 |
| CTTGTCCTGG | TGGCCTACCA | GGTCCAGGCT | GATCCCATTC | AAGGGGCAGA | 1250 |
| AGAAGAGACT | AAAACTGAAG | AGCAACCATC | AGATGAGGAC | CAGGATGTGT | 1300 |
| CTGTCTCCTT | TGAAGGCCCA | GAAGCCTCTG | CTCTTCAAGA | TTTTGGTGAG | 1350 |
| TGCTTATGCA | CAGAATGATG | GAGGCTTGGA | GTCTCCTGAT | GGAGGGTTGT | 1400 |
| AGATTAGACC | TGGAATCCTG | TCAAGAACTG | TCTGGTTCAG | GTAGCTGTCT | 1450 |
| CTTGGTCCCT | TTACATTCCT | TGTCTTCTTC | ATAGAAGTAA | CGGAGAGAGA | 1500 |
| TTAACCATTG | GGCTTGACTT | TTTTCCTTTT | AAAATTTTTG | ATCTAACAAT | 1550 |
| TTATCTGTGG | AAAACCTTTA | AAATATAAAA | CATATTGATT | AGTTCTTTTA | 1600 |
| GACCTGATTG | ATAATTTTGT | TATAAGAAGA | AATATTCGTT | CTACTTTAAA | 1650 |
| AATTAGATTT | GGGACCCAAA | TGCCAGTGTA | TGAAGCTGTT | GGGTAAGGAA | 1700 |
| AAACCAAAAA | TGGTGATAGA | ATGTTGTGTA | GATGACAATT | CCTTTATGCG | 1750 |
| ATTAACACTT | TTTAAAATGT | CTTATCTCCA | TGTGTTTGGG | GTTGATCATG | 1800 |

FIG. 15B(2)

RAT CRYPTIN 2 GENOMIC SEQUENCE

| 10 | 20 | 30 | 40 | 50 | |
|---|---|---|---|---|---|
| 1234567890 | 1234567890 | 1234567890 | 1234567890 | 1234567890 | |
| GTGCTGACTG | TGATGTCACC | CACAGAGCAA | ACCTACTCTC | TACCATGCAC | 1850 |
| AGGACATCTT | CATAGGGTAG | TTCACTGTCA | CACACTGCTG | GCCTCGTTAC | 1900 |
| TTCATGCCTG | ATGCTTTCTT | GTTTCCTCAG | AGATAGGAAG | GCCAGTGAGG | 1950 |
| AGGTGCCGTT | GCAGAGCAAA | CTGCGGACCT | AAAGAATATG | CCACTGCGTT | 2000 |
| CTGTGCTCAA | GGTCCATTTA | AACAGTTCAA | ATTCTGCTGC | ACATGAACAT | 2050 |
| GGATCCCAAG | TCTGAGATAA | CCACGTGCTC | TGGGACCTCA | CAATCTGTCA | 2100 |
| TTATTGTGCT | TGACCTCAAC | TGCTTTTCCT | TCTCCAATAA | ACTCCTGGCA | 2150 |
| GACAAATAAT | CGGTATATGT | TTATTTGATG | CTTTCTATTT | GGCTTAGACA | 2200 |
| GAACTCTCCT | GAGCCATGTA | GCTGAATCTT | CAGTGAATCC | TTTGTAAAGG | 2250 |
| TCACATTTCA | GCAGTCATAT | CAAGGATGAG | CAGGAGGTTA | GATACAAAGA | 2300 |
| GACAAGATGG | TCTGCGCCAG | CTGCTTCTTT | GTCTATCAAG | TCTGCTTTCC | 2350 |
| TTTAGATTAG | AGTCACCATC | AAAAATTATT | CCCACATTTT | CATGTTCTAT | 2400 |
| ATTTTTTT | | | | | 2408 |

FIG. 15C(1)

RAT CRYPTIN 3 GENOMIC SEQUENCE

| 10 | 20 | 30 | 40 | 50 | |
|---|---|---|---|---|---|
| 1234567890 | 1234567890 | 1234567890 | 1234567890 | 1234567890 | |
| CCTGAGACCA | ACTCTGTGAT | AATCAGAAAA | GACAATTATG | TGTCTTAAAT | 50 |
| GTAAGGTTTG | CTTCTTGACT | GATAGATCTA | ACCCTACAGA | GAGATTCAAG | 100 |
| TGGTCTTGTC | CCATTGAACA | ATAGTATATA | TGTTTTATAT | ATATATATAT | 150 |
| ATATATGTAT | ATGTATATAT | ATATGTGTGT | GTGTGTGTGT | GTGTGTCTGT | 200 |
| GTCTGTGTGT | CTGTGTGTCT | GTGTGTCTGT | GTGTCTGTGT | GTGTATGTGT | 250 |
| GTGTATGTGT | ACATATGTTC | AATATGTCTG | TAAAATAGTA | TTCTTGTAGC | 300 |
| TTCACTTACT | TTTGCACAGA | GCTGTAAATA | AGAACATTGT | AGCCAATGAA | 350 |
| TAGTATTTAT | TAACATGTAA | ATAGGAGCTG | GCACCTCTGA | CAGTGGGACT | 400 |
| CCATACAGTG | ACTGTAAACA | ACAGGATGCT | CTAGACCTTT | TGCTGTGTGT | 450 |
| GTGGTGAGAG | ACATGGGATA | AACACAGACT | GAAGTGTATG | ACATGGCGGC | 500 |
| ACTTCTCGAG | ACCGGGTAGC | AGCTTCTGAG | CCTCTCTACA | TTGTGGATGT | 550 |
| CCTTTCCTGT | AGGTCAGGTC | TCATTGTCTA | AAAGTAAAAG | CATTGCAGCA | 600 |
| TCTCAGACCT | GGGAAACACC | CCATGGCTTG | AGGGTCCCGC | AGGTGAAGAG | 650 |
| CCACCTGGAG | CTCACTCTTG | GCAGATGTGT | TCCATGACTT | TGGCTTCTTC | 700 |
| AGAACCACCC | ACTACAGCTT | CACTCTGACA | AATCTTAGAA | ACTTGAACTC | 750 |
| AATTCACTGG | AGGGCACAAT | AAAGCCATCT | TACTTTCTCT | AAAATGGCCC | 800 |
| CAAAGGAGGG | GATTCACAAA | GTTTGCCTTG | ATGAGGACCA | TTGCTAATAC | 850 |
| CCCAAAACTT | GCAAAAAAAA | TTGAGTGTCC | AGTCAACCTG | GTCAAGGACT | 900 |
| GGTCCTGGAT | CCACAGTTTC | TGAGAAAAGA | AGGCTCCAAC | TTCAAAACAC | 950 |
| AAACCACTCC | TGTTCTATGC | GCTCATTAAA | TTAGGCAGTG | TTAAGCTATT | 1000 |
| TTCTTTCCTG | ACCACTGAGA | GGTAAATACT | CAAGCAGATG | GGAAACAGGG | 1050 |
| GAGGACAGCA | AAGCCTGTTC | ATCATTATCA | GTGGGAGTGT | GCGTGAGGGG | 1100 |
| AGGGGTGTCA | GTGAACACAC | AGAGCATCAG | GAAGGAAGCC | TTGAGGACAG | 1150 |
| AGGAACATCA | AAGGGATCCT | GAGGACAACA | GCTGGGAGCA | GTTGGCATCA | 1200 |
| GTGAGTGCCG | TCTCTAAGTG | TGGGGCCTTT | CTCTGCCACA | TAAATGCAGG | 1250 |
| CTGGCTCCTC | TCTCCACACA | CTGGTCTCCA | GCTCACCAAT | CCTCCAGGTG | 1300 |
| ACTTCCAGCC | ATGAAGACTC | TTGTCCTCCT | CTCTGCCCTT | GTCCTGCTGG | 1350 |
| CATTCCAGAT | CCAGGCTGAT | CCCATTCAAG | AGGCAGAAGA | AGAGACTAAA | 1400 |
| ACTGAGGAGC | AGCCAGCAGA | TGAGGACCAG | GATGTGTCTG | TCTCCTTTGA | 1450 |
| AGGCCCAGAA | CCCTCTGCTC | TTCAAAATTT | AGGTGCGTGC | TTGTGCACAG | 1500 |
| AATGATGGAG | GCTTGGAGTC | TCCTGATGGA | GGGTTGTAGA | TTAGCCCTGG | 1550 |
| AGTCCTGTCA | AGGACAGTCT | GGTTCAGGTA | GCTGTCTATT | GATCCTTTCA | 1600 |
| GAACTTCCCT | GTCTTATTCA | TAGAAATAAC | AGTGAGAGAC | AAGCCATTGG | 1650 |
| GCTTGACTTT | TTCCTTTTAA | GATTTTGGTC | TAACAATTTA | TCTGTGAAAA | 1700 |
| ACCTTTAAAA | TATAAAACAT | ATTGATTAGT | TCTTTTAAAC | CTGATTGATA | 1750 |
| ATTTTGTTAT | AGGAAGAAAT | AACTGTTCTA | CTTTAAAAAT | TAGATTTGGT | 1800 |
| ACCTAAATGC | CAGTGTATTA | AGGTGTTGGG | TCAGGAAAAC | ACAATAATGC | 1850 |
| TGATAGAATG | TGGTGTAGAT | GACAATTCCT | ATATGCGATT | AACACTTGTT | 1900 |

FIG. 15C(2)

RAT CRYPTIN 3 GENOMIC SEQUENCE

|  10        |  20        |  30        |  40        |  50        |      |
|------------|------------|------------|------------|------------|------|
| 1234567890 | 1234567890 | 1234567890 | 1234567890 | 1234567890 |      |
| AAATTGTCCT | ATCTCCATGT | GTTTGGGGTT | GATCATGGTG | CTGGCTGTGA | 1950 |
| TGTCACCCAC | ACAGCAAACC | TACTTTCTAC | CATGCACAGG | ACATCTTCAT | 2000 |
| AGGGTAGTTC | ACTGTCACAC | ACTGCTGGCC | TCCTTACTTC | ATGCCTGATG | 2050 |
| CTTTCTCGTT | TCCTCAGAGA | TCAGATGGCC | ATGGAAGAGG | TGCCATTGCA | 2100 |
| GAAGTTTCTG | CAGACCTTAT | GAAAATGCCA | CTTCGTTCTG | TGCTCAAGGT | 2150 |
| CTATTTAAAC | AACACAAATT | CTGCTGCCTA | GAAACATGGC | CCCCAAGGAT | 2200 |
| GAAATAACCA | CGTGCTCTGG | GACCTCACAA | TCTGTCATCA | TTGTGCTTGG | 2250 |
| CCTCAACTTC | TTTTCCTTCT | CCAATAAACT | CCTTGCAGAC | AAATAACCTG | 2300 |
| TTTATGTTTT | TTTGATGCTT | TCTATGTGGC | TTAGACAGGG | CTCTCCTGAG | 2350 |
| CCATGTAGCA | GAATCTTCAG | TGAATCCTTT | GTAAAAGAAG | TCTTGGTCAC | 2400 |
| ATTTCAACAG | TCATATCAAG | GATGAGCAGG | AGGTTAGATC | CAAAGAGACA | 2450 |
| AGATGCTCTG | CTCCAGCTGC | TTCTTGACTA | TCAAGTCTTC | TGTCCTTCAG | 2500 |
| ATTAGAGTCA | CCCTCAAAAA | TTAGTCCCAC | CTTTTCATGT | TCTATTTTTT | 2550 |
| T          |            |            |            |            | 2551 |

SEQUENCE LISTING ( 1 ) GENERAL INFORMATION:

( i i i ) NUMBER OF SEQUENCES: 70

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( x i ) SEQUENCE DESCRIPTION: SEQ ID NO:1:

Leu   Ser   Lys   Lys
    1

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:2:

Gly   Ile   Arg   Phe   Leu   Tyr
    1                            5

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:3:

Arg   Asn   Leu   Phe   Leu   Thr   Phe   Val   Phe
    1                            5

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:4:

```
Arg  Arg  Gly  His  Leu  Met  Tyr  Thr  Leu
1                   5
```

(2) INFORMATION FOR SEQ ID NO:5:

(i) SEQUENCE CHARACTERISTICS:
        (A) LENGTH: 9 amino acids
        (B) TYPE: amino acid
        (D) TOPOLOGY: linear (ix) FEATURE:
        (A) NAME/KEY: Peptide
        (B) LOCATION: 6
        (D) OTHER INFORMATION: /note= "Xaa = Amino acid is
            independently L or M."

(ix) FEATURE:
        (A) NAME/KEY: Peptide
        (B) LOCATION: 9
        (D) OTHER INFORMATION: /note= "Xaa = Amino acid is
            independently L or M"

(xi) SEQUENCE DESCRIPTION: SEQ ID NO:5:

```
Arg  Lys  Gly  His  Leu  Xaa  Tyr  Thr  Xaa
1                   5
```

(2) INFORMATION FOR SEQ ID NO:6:

(i) SEQUENCE CHARACTERISTICS:
        (A) LENGTH: 35 amino acids
        (B) TYPE: amino acid
        (D) TOPOLOGY: linear (xi) SEQUENCE DESCRIPTION: SEQ ID NO:6:

```
Leu  Arg  Asp  Leu  Val  Cys  Tyr  Cys  Arg  Ser  Arg  Gly  Cys  Lys  Gly  Arg
1                   5                        10                       15
Glu  Arg  Met  Asn  Gly  Thr  Cys  Arg  Lys  Gly  His  Leu  Leu  Tyr  Thr  Leu
               20                       25                       30
Cys  Cys  Arg
          35
```

(2) INFORMATION FOR SEQ ID NO:7:

(i) SEQUENCE CHARACTERISTICS:
        (A) LENGTH: 35 amino acids
        (B) TYPE: amino acid
        (D) TOPOLOGY: linear (xi) SEQUENCE DESCRIPTION: SEQ ID NO:7:

```
Leu  Arg  Asp  Leu  Val  Cys  Tyr  Cys  Arg  Thr  Arg  Gly  Cys  Lys  Arg  Arg
1                   5                        10                       15
Glu  Arg  Met  Asn  Gly  Thr  Cys  Arg  Lys  Gly  His  Leu  Met  Tyr  Thr  Leu
               20                       25                       30
Cys  Cys  Arg
          35
```

(2) INFORMATION FOR SEQ ID NO:8:

(i) SEQUENCE CHARACTERISTICS:
        (A) LENGTH: 35 amino acids
        (B) TYPE: amino acid
        (D) TOPOLOGY: linear (xi) SEQUENCE DESCRIPTION: SEQ ID NO:8:

```
Leu  Arg  Asp  Leu  Val  Cys  Tyr  Cys  Arg  Lys  Arg  Gly  Cys  Lys  Arg  Arg
1                   5                        10                       15
Glu  Arg  Met  Asn  Gly  Thr  Cys  Arg  Lys  Gly  His  Leu  Met  Tyr  Thr  Leu
```

Cys Cys Arg
      35

(2) INFORMATION FOR SEQ ID NO:9:

(i) SEQUENCE CHARACTERISTICS:
       (A) LENGTH: 31 amino acids
       (B) TYPE: amino acid
       (D) TOPOLOGY: linear (xi) SEQUENCE DESCRIPTION: SEQ ID NO:9:

Gly Leu Leu Cys Tyr Cys Arg Lys Gly His Cys Lys Arg Gly Glu Arg
1               5                   10                  15

Val Arg Gly Thr Cys Gly Ile Arg Phe Leu Tyr Cys Cys Pro Arg
            20                  25                  30

(2) INFORMATION FOR SEQ ID NO:10:

(i) SEQUENCE CHARACTERISTICS:
       (A) LENGTH: 35 amino acids
       (B) TYPE: amino acid
       (D) TOPOLOGY: linear (xi) SEQUENCE DESCRIPTION: SEQ ID NO:10:

Leu Ser Lys Lys Leu Ile Cys Tyr Cys Arg Ile Arg Gly Cys Lys Arg
1               5                   10                  15

Arg Glu Arg Val Phe Gly Thr Cys Arg Asn Leu Phe Leu Thr Phe Val
            20                  25                  30

Phe Cys Cys
        35

(2) INFORMATION FOR SEQ ID NO:11:

(i) SEQUENCE CHARACTERISTICS:
       (A) LENGTH: 39 amino acids
       (B) TYPE: amino acid
       (D) TOPOLOGY: linear (xi) SEQUENCE DESCRIPTION: SEQ ID NO:11:

Leu Lys Gln Cys His Cys Arg Lys Phe Cys Arg Pro Tyr Glu Lys Ala
1               5                   10                  15

Glu Gly Ser Cys Arg Pro Gly Leu Phe Ile Lys Arg Lys Ile Cys Cys
            20                  25                  30

Ile Gln Gln Trp Thr Pro Gly
        35

(2) INFORMATION FOR SEQ ID NO:12:

(i) SEQUENCE CHARACTERISTICS:
       (A) LENGTH: 32 amino acids
       (B) TYPE: amino acid
       (D) TOPOLOGY: linear (xi) SEQUENCE DESCRIPTION: SEQ ID NO:12:

Gly Leu Leu Cys Tyr Cys Arg Lys Gly His Cys Lys Arg Gly Glu Arg
1               5                   10                  15

Val Arg Gly Thr Cys Gly Ile Arg Phe Leu Tyr Cys Cys Pro Arg Arg
            20                  25                  30

(2) INFORMATION FOR SEQ ID NO:13:

(i) SEQUENCE CHARACTERISTICS:
       (A) LENGTH: 36 amino acids (B) TYPE: amino acid
(D) TOPOLOGY: linear (xi) SEQUENCE DESCRIPTION: SEQ ID NO:13:

| Leu | Ser | Lys | Lys | Leu | Ile | Cys | Tyr | Cys | Arg | Ile | Arg | Gly | Cys | Lys | Arg |
|---|---|---|---|---|---|---|---|---|---|---|---|---|---|---|---|
| 1 | | | | 5 | | | | | 10 | | | | | 15 | |
| Arg | Glu | Arg | Val | Phe | Gly | Thr | Cys | Arg | Asn | Leu | Phe | Leu | Thr | Phe | Val |
| | | | 20 | | | | | 25 | | | | | 30 | | |
| Phe | Cys | Cys | Ser | | | | | | | | | | | | |
| | | | 35 | | | | | | | | | | | | |

(2) INFORMATION FOR SEQ ID NO:14:

(i) SEQUENCE CHARACTERISTICS:
(A) LENGTH: 35 amino acids
(B) TYPE: amino acid
(D) TOPOLOGY: linear (xi) SEQUENCE DESCRIPTION: SEQ ID NO:14:

| Leu | Arg | Asp | Leu | Val | Cys | Tyr | Cys | Arg | Ala | Arg | Gly | Cys | Lys | Gly | Arg |
|---|---|---|---|---|---|---|---|---|---|---|---|---|---|---|---|
| 1 | | | | 5 | | | | | 10 | | | | | 15 | |
| Glu | Arg | Met | Asn | Gly | Thr | Cys | Arg | Lys | Gly | His | Leu | Leu | Tyr | Met | Leu |
| | | | 20 | | | | | 25 | | | | | 30 | | |
| Cys | Cys | Arg | | | | | | | | | | | | | |
| | | | 35 | | | | | | | | | | | | |

(2) INFORMATION FOR SEQ ID NO:15:

(i) SEQUENCE CHARACTERISTICS:
(A) LENGTH: 41 amino acids
(B) TYPE: amino acid
(D) TOPOLOGY: linear (xi) SEQUENCE DESCRIPTION: SEQ ID NO:15:

| Leu | Lys | Gln | Cys | His | Cys | Arg | Lys | Phe | Cys | Arg | Pro | Tyr | Glu | Lys | Ala |
|---|---|---|---|---|---|---|---|---|---|---|---|---|---|---|---|
| 1 | | | | 5 | | | | | 10 | | | | | 15 | |
| Glu | Gly | Ser | Cys | Arg | Pro | Gly | Leu | Phe | Ile | Lys | Arg | Lys | Ile | Cys | Cys |
| | | | 20 | | | | | 25 | | | | | 30 | | |
| Ile | Gln | Gln | Trp | Thr | Pro | Gly | Arg | Thr | | | | | | | |
| | | | 35 | | | | | 40 | | | | | | | |

(2) INFORMATION FOR SEQ ID NO:16:

(i) SEQUENCE CHARACTERISTICS:
(A) LENGTH: 37 amino acids
(B) TYPE: amino acid
(D) TOPOLOGY: linear (xi) SEQUENCE DESCRIPTION: SEQ ID NO:16:

| Ile | Gly | Arg | Pro | Val | Arg | Arg | Cys | Arg | Cys | Arg | Ala | Asn | Cys | Gly | Pro |
|---|---|---|---|---|---|---|---|---|---|---|---|---|---|---|---|
| 1 | | | | 5 | | | | | 10 | | | | | 15 | |
| Lys | Glu | Tyr | Ala | Thr | Ala | Phe | Cys | Ala | Gln | Gly | Pro | Phe | Lys | Gln | Phe |
| | | | 20 | | | | | 25 | | | | | 30 | | |
| Lys | Phe | Cys | Cys | Thr | | | | | | | | | | | |
| | | | 35 | | | | | | | | | | | | |

(2) INFORMATION FOR SEQ ID NO:17:

(i) SEQUENCE CHARACTERISTICS:
(A) LENGTH: 45 amino acids
(B) TYPE: amino acid
(D) TOPOLOGY: linear (xi) SEQUENCE DESCRIPTION: SEQ ID NO:17:

```
        Ile  Arg  Trp  Pro  Trp  Lys  Arg  Cys  His  Cys  Arg  Ser  Phe  Cys  Arg  Pro
        1              5                        10                           15

Tyr  Glu  Asn  Ala  Thr  Ser  Phe  Cys  Ala  Gln  Gly  Leu  Phe  Lys  Gln  His
                       20                       25                      30

Lys  Phe  Cys  Cys  Leu  Asp  Thr  Trp  Pro  Pro  Arg  Met  Lys
                  35                      40                      45
```

( 2 ) INFORMATION FOR SEQ ID NO:18:

( i ) SEQUENCE CHARACTERISTICS:
        ( A ) LENGTH: 39 amino acids
        ( B ) TYPE: amino acid
        ( D ) TOPOLOGY: linear ( x i ) SEQUENCE DESCRIPTION: SEQ ID NO:18:

```
        Thr  Ser  Gly  Ser  Gln  Ala  Arg  Ala  Thr  Cys  Tyr  Cys  Arg  Thr  Gly  Arg
        1              5                        10                           15

Cys  Ala  Thr  Arg  Glu  Ser  Leu  Ser  Gly  Val  Cys  Glu  Ile  Ser  Gly  Arg
                       20                       25                      30

Leu  Tyr  Arg  Leu  Cys  Cys  Arg
                  35
```

( 2 ) INFORMATION FOR SEQ ID NO:19:

( i ) SEQUENCE CHARACTERISTICS:
        ( A ) LENGTH: 32 amino acids
        ( B ) TYPE: amino acid
        ( D ) TOPOLOGY: linear ( x i ) SEQUENCE DESCRIPTION: SEQ ID NO:19:

```
        Ala  Phe  Thr  Cys  His  Cys  Arg  Arg  Ser  Cys  Tyr  Ser  Thr  Glu  Tyr  Ser
        1              5                        10                           15

Tyr  Gly  Thr  Cys  Thr  Val  Met  Gly  Ile  Asn  His  Arg  Phe  Cys  Cys  Leu
                       20                       25                      30
```

( 2 ) INFORMATION FOR SEQ ID NO:20:

( i ) SEQUENCE CHARACTERISTICS:
        ( A ) LENGTH: 103 amino acids
        ( B ) TYPE: amino acid
        ( D ) TOPOLOGY: linear ( x i ) SEQUENCE DESCRIPTION: SEQ ID NO:20:

```
        Met  Lys  Thr  Leu  Val  Leu  Leu  Ser  Ala  Leu  Val  Leu  Leu  Ala  Phe  Gln
        1              5                        10                           15

Val  Gln  Ala  Asp  Pro  Ile  Gln  Glu  Ala  Glu  Glu  Thr  Lys  Thr  Glu
                       20                       25                      30

Glu  Gln  Pro  Ala  Asp  Glu  Asp  Gln  Asp  Val  Ser  Val  Ser  Phe  Glu  Gly
                  35                      40                      45

Pro  Glu  Pro  Ser  Ala  Leu  Gln  Asn  Leu  Glu  Ile  Gly  Trp  Pro  Leu  Lys
             50                      55                      60

Gln  Cys  His  Cys  Arg  Lys  Phe  Cys  Arg  Pro  Tyr  Glu  Lys  Ala  Glu  Gly
        65                      70                      75                           80

Ser  Cys  Arg  Pro  Gly  Leu  Phe  Ile  Lys  Arg  Lys  Ile  Cys  Cys  Ile  Gln
                       85                       90                           95

Gln  Trp  Thr  Pro  Gly  Arg  Thr
                       100
```

( 2 ) INFORMATION FOR SEQ ID NO:21:

( i ) SEQUENCE CHARACTERISTICS:

(A) LENGTH: 96 amino acids
(B) TYPE: amino acid
(D) TOPOLOGY: linear (xi) SEQUENCE DESCRIPTION: SEQ ID NO:21:

| Met | Lys | Thr | Leu | Val | Leu | Leu | Ser | Ala | Leu | Val | Leu | Val | Ala | Tyr | Gln |
|---|---|---|---|---|---|---|---|---|---|---|---|---|---|---|---|
| 1 | | | | 5 | | | | | 10 | | | | | 15 | |
| Val | Gln | Ala | Asp | Pro | Ile | Gln | Gly | Ala | Glu | Glu | Thr | Lys | Thr | Glu | |
| | | | 20 | | | | 25 | | | | | 30 | | | |
| Glu | Gln | Pro | Ser | Asp | Glu | Asp | Gln | Asp | Val | Ser | Val | Ser | Phe | Glu | Gly |
| | | 35 | | | | 40 | | | | | 45 | | | | |
| Pro | Glu | Ala | Ser | Ala | Leu | Gln | Asp | Phe | Glu | Ile | Gly | Arg | Pro | Val | Arg |
| | 50 | | | | | 55 | | | | | 60 | | | | |
| Arg | Cys | Arg | Cys | Arg | Ala | Asn | Cys | Gly | Pro | Lys | Glu | Tyr | Ala | Thr | Ala |
| 65 | | | | | 70 | | | | | 75 | | | | | 80 |
| Phe | Cys | Ala | Gln | Gly | Pro | Phe | Lys | Gln | Phe | Lys | Arg | Phe | Cys | Cys | Thr |
| | | | | 85 | | | | | 90 | | | | | 95 | |

(2) INFORMATION FOR SEQ ID NO:22:

(i) SEQUENCE CHARACTERISTICS:
(A) LENGTH: 103 amino acids
(B) TYPE: amino acid
(D) TOPOLOGY: linear (xi) SEQUENCE DESCRIPTION: SEQ ID NO:22:

| Met | Lys | Thr | Leu | Val | Leu | Leu | Ser | Ala | Leu | Val | Leu | Leu | Ala | Phe | Gln |
|---|---|---|---|---|---|---|---|---|---|---|---|---|---|---|---|
| 1 | | | | 5 | | | | | 10 | | | | | 15 | |
| Ile | Gln | Ala | Asp | Pro | Ile | Gln | Glu | Ala | Glu | Glu | Thr | Lys | Thr | Glu | |
| | | | 20 | | | | 25 | | | | | 30 | | | |
| Glu | Gln | Pro | Ala | Asp | Glu | Asp | Gln | Asp | Val | Ser | Val | Ser | Phe | Glu | Gly |
| | | 35 | | | | 40 | | | | | 45 | | | | |
| Pro | Glu | Pro | Ser | Ala | Leu | Gln | Asn | Leu | Glu | Ile | Arg | Trp | Pro | Trp | Lys |
| | 50 | | | | | 55 | | | | | 60 | | | | |
| Arg | Cys | His | Cys | Arg | Ser | Phe | Cys | Arg | Pro | Tyr | Glu | Asn | Ala | Thr | Ser |
| 65 | | | | | 70 | | | | | 75 | | | | | 80 |
| Phe | Cys | Ala | Gln | Gly | Leu | Phe | Lys | Gln | His | Lys | Phe | Cys | Cys | Leu | Asp |
| | | | | 85 | | | | | 90 | | | | | 95 | |
| Thr | Trp | Pro | Pro | Arg | Met | Lys | | | | | | | | | |
| | | | 100 | | | | | | | | | | | | |

(2) INFORMATION FOR SEQ ID NO:23:

(i) SEQUENCE CHARACTERISTICS:
(A) LENGTH: 93 amino acids
(B) TYPE: amino acid
(D) TOPOLOGY: linear (xi) SEQUENCE DESCRIPTION: SEQ ID NO:23:

| Met | Lys | Thr | Leu | Val | Leu | Leu | Ser | Ala | Leu | Val | Leu | Leu | Ala | Phe | Gln |
|---|---|---|---|---|---|---|---|---|---|---|---|---|---|---|---|
| 1 | | | | 5 | | | | | 10 | | | | | 15 | |
| Val | Gln | Ala | Asp | Pro | Ile | Gln | Asn | Thr | Asp | Glu | Glu | Thr | Lys | Thr | Glu |
| | | | 20 | | | | 25 | | | | | 30 | | | |
| Glu | Gln | Pro | Gly | Glu | Asp | Asp | Gln | Ala | Val | Ser | Val | Ser | Phe | Gly | Asp |
| | | 35 | | | | 40 | | | | | 45 | | | | |
| Pro | Glu | Gly | Thr | Ser | Leu | Gln | Glu | Glu | Ser | Leu | Arg | Asp | Leu | Val | Cys |
| | 50 | | | | | 55 | | | | | 60 | | | | |
| Tyr | Cys | Arg | Ser | Arg | Gly | Cys | Lys | Gly | Arg | Glu | Arg | Met | Asn | Gly | Thr |
| 65 | | | | | 70 | | | | | 75 | | | | | 80 |

Cys Arg Lys Gly His Leu Leu Tyr Thr Leu Cys Cys Arg
                    85                      90

(2) INFORMATION FOR SEQ ID NO:24:

(i) SEQUENCE CHARACTERISTICS:
        (A) LENGTH: 93 amino acids
        (B) TYPE: amino acid
        (D) TOPOLOGY: linear (xi) SEQUENCE DESCRIPTION: SEQ ID NO:24:

Met Lys Thr Leu Ile Leu Leu Ser Ala Leu Val Leu Leu Ala Phe Gln
1                5                  10                      15

Val Gln Ala Asp Pro Ile Gln Asn Thr Asp Glu Glu Thr Lys Thr Glu
             20              25                  30

Lys Gln Pro Gly Glu Glu Asp Gln Ala Val Ser Val Ser Phe Gly Asp
         35                  40              45

Pro Glu Gly Ser Ser Leu Gln Glu Glu Ser Leu Arg Asp Leu Val Cys
     50              55                  60

Tyr Cys Arg Thr Arg Gly Cys Lys Arg Arg Glu Arg Met Asn Gly Thr
65              70                  75                      80

Cys Arg Lys Gly His Leu Met Tyr Thr Leu Cys Cys Arg
                    85                      90

(2) INFORMATION FOR SEQ ID NO:25:

(i) SEQUENCE CHARACTERISTICS:
        (A) LENGTH: 93 amino acids
        (B) TYPE: amino acid
        (D) TOPOLOGY: linear (xi) SEQUENCE DESCRIPTION: SEQ ID NO:25:

Met Lys Thr Leu Val Leu Leu Ser Ala Leu Val Leu Leu Ala Phe Gln
1                5                  10                      15

Val Gln Ala Asp Pro Ile Gln Asn Thr Asp Glu Glu Thr Lys Thr Glu
             20              25                  30

Glu Gln Pro Gly Glu Asp Asp Gln Ala Val Ser Val Ser Phe Gly Asp
         35                  40              45

Pro Glu Gly Ser Ser Leu Gln Glu Glu Ser Leu Arg Asp Leu Val Cys
     50              55                  60

Tyr Cys Arg Lys Arg Gly Cys Lys Arg Arg Glu Arg Met Asn Gly Thr
65              70                  75                      80

Cys Arg Lys Gly His Leu Met Tyr Thr Leu Cys Cys Arg
                    85                      90

(2) INFORMATION FOR SEQ ID NO:26:

(i) SEQUENCE CHARACTERISTICS:
        (A) LENGTH: 92 amino acids
        (B) TYPE: amino acid
        (D) TOPOLOGY: linear (ix) FEATURE:
        (A) NAME/KEY: Peptide
        (B) LOCATION: 79
        (D) OTHER INFORMATION: /note= "Xaa = Amino acid is
            independently L or M."

(ix) FEATURE:
        (A) NAME/KEY: Peptide
        (B) LOCATION: 80
        (D) OTHER INFORMATION: /note= "Xaa = Amino acid is
            independently L or M."

(ix) FEATURE:

(A) NAME/KEY: Peptide
(B) LOCATION: 82
(D) OTHER INFORMATION: /note= "Xaa = Amino acid is independently L or M."

(xi) SEQUENCE DESCRIPTION: SEQ ID NO:26:

| Leu | Val | Leu | Leu | Ser | Ala | Leu | Val | Leu | Leu | Ala | Phe | Gln | Val | Gln | Ala |
|---|---|---|---|---|---|---|---|---|---|---|---|---|---|---|---|
| 1 | | | | 5 | | | | | 10 | | | | | 15 | |
| Asp | Pro | Ile | Gln | Asn | Thr | Asp | Glu | Glu | Thr | Lys | Thr | Glu | Glu | Gln | Pro |
| | | | 20 | | | | | 25 | | | | | 30 | | |
| Gly | Glu | Glu | Asp | Gln | Ala | Val | Ser | Ile | Ser | Phe | Gly | Gly | Gln | Glu | Gly |
| | | 35 | | | | | 40 | | | | | 45 | | | |
| Ser | Ala | Leu | His | Glu | Lys | Ser | Leu | Arg | Gly | Leu | Leu | Cys | Tyr | Cys | Arg |
| | 50 | | | | | 55 | | | | | 60 | | | | |
| Lys | Gly | His | Cys | Lys | Arg | Gly | Glu | Arg | Val | Arg | Gly | Thr | Cys | Xaa | Xaa |
| 65 | | | | | 70 | | | | | 75 | | | | | 80 |
| Gly | Xaa | Ile | Arg | Phe | Leu | Tyr | Cys | Cys | Pro | Arg | Arg | | | | |
| | | | | 85 | | | | | 90 | | | | | | |

(2) INFORMATION FOR SEQ ID NO:27:

(i) SEQUENCE CHARACTERISTICS:
 (A) LENGTH: 93 amino acids
 (B) TYPE: amino acid
 (D) TOPOLOGY: linear (xi) SEQUENCE DESCRIPTION: SEQ ID NO:27:

| Met | Lys | Thr | Phe | Val | Leu | Leu | Ser | Ala | Leu | Val | Leu | Leu | Ala | Phe | Gln |
|---|---|---|---|---|---|---|---|---|---|---|---|---|---|---|---|
| 1 | | | | 5 | | | | | 10 | | | | | 15 | |
| Val | Gln | Ala | Asp | Pro | Ile | His | Lys | Thr | Asp | Glu | Glu | Thr | Asn | Thr | Glu |
| | | | 20 | | | | | 25 | | | | | 30 | | |
| Glu | Gln | Pro | Gly | Glu | Glu | Asp | Gln | Ala | Val | Ser | Ile | Ser | Phe | Gly | Gly |
| | | 35 | | | | | 40 | | | | | 45 | | | |
| Gln | Glu | Gly | Ser | Ala | Leu | His | Glu | Glu | Leu | Ser | Lys | Lys | Leu | Ile | Cys |
| | 50 | | | | | 55 | | | | | 60 | | | | |
| Tyr | Cys | Arg | Ile | Arg | Gly | Cys | Lys | Arg | Arg | Glu | Arg | Val | Phe | Gly | Thr |
| 65 | | | | | 70 | | | | | 75 | | | | | 80 |
| Cys | Arg | Asn | Leu | Phe | Leu | Thr | Phe | Val | Phe | Cys | Cys | Ser | | | |
| | | | | 85 | | | | | 90 | | | | | | |

(2) INFORMATION FOR SEQ ID NO:28:

(i) SEQUENCE CHARACTERISTICS:
 (A) LENGTH: 93 amino acids
 (B) TYPE: amino acid
 (D) TOPOLOGY: linear (xi) SEQUENCE DESCRIPTION: SEQ ID NO:28:

| Met | Lys | Thr | Leu | Val | Leu | Leu | Ser | Ala | Leu | Val | Leu | Leu | Ala | Phe | Gln |
|---|---|---|---|---|---|---|---|---|---|---|---|---|---|---|---|
| 1 | | | | 5 | | | | | 10 | | | | | 15 | |
| Val | Gln | Ala | Asp | Pro | Ile | Gln | Asn | Thr | Asp | Glu | Glu | Thr | Lys | Thr | Glu |
| | | | 20 | | | | | 25 | | | | | 30 | | |
| Glu | Gln | Pro | Gly | Glu | Glu | Asp | Gln | Ala | Val | Ser | Val | Ser | Phe | Gly | Asp |
| | | 35 | | | | | 40 | | | | | 45 | | | |
| Pro | Glu | Gly | Thr | Ser | Leu | Gln | Glu | Glu | Ser | Leu | Arg | Asp | Leu | Val | Cys |
| | 50 | | | | | 55 | | | | | 60 | | | | |
| Tyr | Cys | Arg | Ala | Arg | Gly | Cys | Lys | Gly | Arg | Glu | Arg | Met | Asn | Gly | Thr |
| 65 | | | | | 70 | | | | | 75 | | | | | 80 |
| Cys | Arg | Lys | Gly | His | Leu | Leu | Tyr | Met | Leu | Cys | Cys | Arg | | | |
| | | | | 85 | | | | | 90 | | | | | | |

( 2 ) INFORMATION FOR SEQ ID NO:29:

( i ) SEQUENCE CHARACTERISTICS:
        ( A ) LENGTH: 93 amino acids
        ( B ) TYPE: amino acid
        ( D ) TOPOLOGY: linear ( x i ) SEQUENCE DESCRIPTION: SEQ ID NO:29:

```
Met Lys Thr Leu Ile Leu Leu Ser Ala Leu Val Leu Leu Ala Phe Gln
 1               5                   10                  15

Val Gln Ala Asp Pro Ile Gln Asn Thr Asp Glu Glu Thr Lys Thr Glu
            20                  25                  30

Glu Gln Pro Gly Glu Asp Asp Gln Ala Val Ser Val Ser Phe Gly Asp
        35                  40                  45

Pro Glu Gly Ser Ser Leu Gln Glu Glu Ser Leu Arg Asp Leu Val Cys
    50                  55                  60

Tyr Cys Arg Thr Arg Gly Cys Lys Arg Arg Glu His Met Asn Gly Thr
65                  70                  75                  80

Cys Arg Lys Gly His Leu Met Tyr Thr Leu Cys Cys Arg
                85                  90
```

( 2 ) INFORMATION FOR SEQ ID NO:30:

( i ) SEQUENCE CHARACTERISTICS:
        ( A ) LENGTH: 93 amino acids
        ( B ) TYPE: amino acid
        ( D ) TOPOLOGY: linear ( x i ) SEQUENCE DESCRIPTION: SEQ ID NO:30:

```
Met Lys Thr Leu Val Leu Leu Ser Ala Leu Val Leu Leu Ala Phe Gln
 1               5                   10                  15

Val Gln Ala Asp Pro Ile Gln Asn Thr Asp Glu Glu Thr Lys Thr Glu
            20                  25                  30

Glu Gln Pro Gly Glu Glu Asp Gln Ala Val Ser Val Ser Phe Gly Asp
        35                  40                  45

Pro Glu Gly Ser Ser Leu Gln Glu Glu Ser Leu Arg Asp Leu Val Cys
    50                  55                  60

Tyr Cys Arg Lys Arg Gly Cys Lys Arg Arg Glu His Met Asn Gly Thr
65                  70                  75                  80

Cys Arg Lys Gly His Leu Leu Tyr Met Leu Cys Cys Arg
                85                  90
```

( 2 ) INFORMATION FOR SEQ ID NO:31:

( i ) SEQUENCE CHARACTERISTICS:
        ( A ) LENGTH: 81 amino acids
        ( B ) TYPE: amino acid
        ( D ) TOPOLOGY: linear ( x i ) SEQUENCE DESCRIPTION: SEQ ID NO:31:

```
Leu Ala Phe Gln Val Gln Ala Asp Pro Ile Gln Asn Thr Asp Glu Glu
 1               5                   10                  15

Thr Lys Thr Glu Glu Gln Pro Gly Glu Asp Asp Gln Ala Val Ser Val
            20                  25                  30

Ser Phe Gly Asp Pro Glu Gly Ser Ser Leu Gln Glu Glu Ser Leu Arg
        35                  40                  45

Asp Leu Val Cys Tyr Cys Arg Lys Arg Gly Cys Lys Arg Arg Glu His
    50                  55                  60

Met Asn Gly Thr Cys Arg Lys Gly His Leu Met Tyr Thr Leu Cys Cys
65                  70                  75                  80
```

Arg
65

(2) INFORMATION FOR SEQ ID NO:32:

(i) SEQUENCE CHARACTERISTICS:
        (A) LENGTH: 92 amino acids
        (B) TYPE: amino acid
        (D) TOPOLOGY: linear (xi) SEQUENCE DESCRIPTION: SEQ ID NO:32:

```
Lys Thr Leu Val Leu Leu Ser Ala Leu Val Leu Leu Ala Phe Gln Val
  1               5                  10                  15
Gln Ala Asp Pro Ile Gln Asn Thr Asp Glu Glu Thr Lys Thr Glu Glu
             20                  25                  30
Gln Pro Gly Glu Asp Asp Gln Ala Val Ser Val Ser Phe Gly Asp Pro
         35                  40                  45
Glu Gly Ser Ser Leu Gln Glu Ser Leu Arg Asp Leu Val Cys Tyr
     50                  55                  60
Cys Arg Lys Arg Gly Cys Lys Gly Arg Glu Arg Met Asn Gly Thr Cys
 65                  70                  75                  80
Arg Lys Gly His Leu Leu Tyr Thr Leu Cys Cys Arg
                 85                  90
```

(2) INFORMATION FOR SEQ ID NO:33:

(i) SEQUENCE CHARACTERISTICS:
        (A) LENGTH: 85 amino acids
        (B) TYPE: amino acid
        (D) TOPOLOGY: linear (xi) SEQUENCE DESCRIPTION: SEQ ID NO:33:

```
Ala Leu Val Leu Leu Ala Phe Gln Val Gln Ala Asp Pro Ile Gln Asn
  1               5                  10                  15
Thr Asp Glu Glu Thr Lys Thr Glu Glu Gln Pro Gly Glu Glu Asp Gln
             20                  25                  30
Ala Val Ser Val Ser Phe Gly Asp Pro Glu Gly Thr Ser Leu Gln Glu
         35                  40                  45
Glu Ser Leu Arg Asp Leu Val Cys Tyr Cys Arg Ser Arg Gly Cys Lys
     50                  55                  60
Gly Arg Glu Arg Met Asn Gly Thr Cys Arg Lys Gly His Leu Leu Tyr
 65                  70                  75                  80
Met Leu Cys Cys Arg
             85
```

(2) INFORMATION FOR SEQ ID NO:34:

(i) SEQUENCE CHARACTERISTICS:
        (A) LENGTH: 93 amino acids
        (B) TYPE: amino acid
        (D) TOPOLOGY: linear (xi) SEQUENCE DESCRIPTION: SEQ ID NO:34:

```
Met Lys Thr Leu Ile Leu Leu Ser Ala Leu Val Leu Leu Ala Phe Gln
  1               5                  10                  15
Val Gln Ala Asp Pro Ile Gln Asn Thr Asp Glu Glu Thr Lys Thr Glu
             20                  25                  30
Glu Gln Pro Gly Glu Glu Asp Gln Ala Val Ser Val Ser Phe Gly Asp
         35                  40                  45
Pro Glu Gly Thr Ser Leu Gln Glu Glu Ser Leu Arg Asp Leu Val Cys
```

|   | 50 |   |   |   | 55 |   |   |   | 60 |   |   |   |
|---|----|---|---|---|----|---|---|---|----|---|---|---|

Tyr Cys Arg Ala Arg Gly Cys Lys Gly Arg Glu Arg Met Asn Gly Thr
65                              70                          75                          80

Cys Arg Lys Gly His Leu Met Tyr Thr Leu Cys Cys Arg
                       85                          90

( 2 ) INFORMATION FOR SEQ ID NO:35:

( i ) SEQUENCE CHARACTERISTICS:
        ( A ) LENGTH: 93 amino acids
        ( B ) TYPE: amino acid
        ( D ) TOPOLOGY: linear ( x i ) SEQUENCE DESCRIPTION: SEQ ID NO:35:

Met Lys Thr Leu Val Leu Leu Ser Ala Leu Val Leu Leu Ala Phe Gln
1                       5                          10                          15

Val Gln Ala Asp Pro Ile Gln Asn Thr Asp Glu Glu Thr Lys Thr Glu
                       20                          25                          30

Glu Gln Pro Gly Glu Glu Asp Gln Ala Val Ser Val Ser Phe Gly Asp
                       35                          40                          45

Pro Glu Gly Thr Ser Leu Gln Glu Glu Ser Leu Arg Asp Leu Val Cys
           50                          55                          60

Tyr Cys Arg Lys Arg Gly Cys Lys Arg Arg Glu His Met Asn Gly Thr
65                            70                          75                          80

Cys Arg Arg Gly His Leu Met Tyr Thr Leu Cys Cys Arg
                       85                          90

( 2 ) INFORMATION FOR SEQ ID NO:36:

( i ) SEQUENCE CHARACTERISTICS:
        ( A ) LENGTH: 85 amino acids
        ( B ) TYPE: amino acid
        ( D ) TOPOLOGY: linear ( x i ) SEQUENCE DESCRIPTION: SEQ ID NO:36:

Ala Leu Val Leu Leu Ala Phe Gln Val Gln Ala Asp Pro Ile Gln Asn
1                       5                          10                          15

Thr Asp Glu Glu Thr Lys Thr Glu Glu Gln Pro Gly Glu Glu Asp Gln
                       20                          25                          30

Ala Val Ser Val Ser Phe Gly Asp Pro Glu Gly Ser Ser Leu Gln Glu
                       35                          40                          45

Glu Ser Leu Arg Asp Leu Val Cys Tyr Cys Arg Thr Arg Gly Cys Lys
           50                          55                          60

Arg Arg Glu Arg Met Asn Gly Thr Cys Arg Lys Gly His Leu Met His
65                            70                          75                          80

Thr Leu Cys Cys Arg
               85

( 2 ) INFORMATION FOR SEQ ID NO:37:

( i ) SEQUENCE CHARACTERISTICS:
        ( A ) LENGTH: 93 amino acids
        ( B ) TYPE: amino acid
        ( D ) TOPOLOGY: linear ( x i ) SEQUENCE DESCRIPTION: SEQ ID NO:37:

Met Lys Thr Leu Val Leu Leu Ser Ala Leu Val Leu Leu Ala Phe Gln
1                       5                          10                          15

Val Gln Ala Asp Pro Ile Gln Asn Thr Asp Glu Glu Thr Lys Thr Glu
                       20                          25                          30

```
Glu  Gln  Pro  Gly  Glu  Asp  Asp  Gln  Ala  Val  Ser  Val  Ser  Phe  Gly  Asp
          35                      40                      45

Pro  Glu  Gly  Ser  Ser  Leu  Gln  Glu  Glu  Ser  Leu  Arg  Asp  Leu  Val  Cys
          50                      55                      60

Tyr  Cys  Arg  Lys  Arg  Gly  Cys  Lys  Arg  Arg  Glu  His  Ile  Asn  Gly  Thr
65                            70                      75                      80

Cys  Arg  Lys  Gly  His  Leu  Leu  Tyr  Met  Leu  Cys  Cys  Arg
                    85                      90
```

( 2 ) INFORMATION FOR SEQ ID NO:38:

( i ) SEQUENCE CHARACTERISTICS:
        ( A ) LENGTH: 93 amino acids
        ( B ) TYPE: amino acid
        ( D ) TOPOLOGY: linear ( x i ) SEQUENCE DESCRIPTION: SEQ ID NO:38:

```
Met  Lys  Thr  Leu  Ile  Leu  Leu  Ser  Ala  Leu  Val  Leu  Leu  Ala  Phe  Gln
1                        5                       10                      15

Val  Gln  Ala  Asp  Pro  Ile  Gln  Asn  Thr  Asp  Glu  Glu  Thr  Lys  Thr  Glu
          20                      25                      30

Glu  Gln  Pro  Gly  Glu  Glu  Asp  Gln  Ala  Val  Ser  Val  Ser  Phe  Gly  Asp
          35                      40                      45

Pro  Glu  Gly  Thr  Ser  Leu  Gln  Glu  Glu  Ser  Leu  Arg  Asp  Leu  Val  Cys
          50                      55                      60

Tyr  Cys  Arg  Ser  Arg  Gly  Cys  Lys  Gly  Arg  Glu  Arg  Met  Asn  Gly  Thr
65                            70                      75                      80

Cys  Arg  Lys  Gly  His  Leu  Met  Tyr  Thr  Leu  Cys  Cys  Arg
                    85                      90
```

( 2 ) INFORMATION FOR SEQ ID NO:39:

( i ) SEQUENCE CHARACTERISTICS:
        ( A ) LENGTH: 82 amino acids
        ( B ) TYPE: amino acid
        ( D ) TOPOLOGY: linear ( x i ) SEQUENCE DESCRIPTION: SEQ ID NO:39:

```
Leu  Leu  Ala  Phe  Gln  Val  Gln  Ala  Asp  Pro  Ile  Gln  Asn  Thr  Asp  Glu
1                        5                       10                      15

Glu  Thr  Lys  Thr  Glu  Glu  Gln  Pro  Gly  Glu  Glu  Asp  Gln  Ala  Val  Ser
          20                      25                      30

Val  Ser  Phe  Gly  Asp  Pro  Glu  Gly  Thr  Ser  Leu  Gln  Glu  Glu  Ser  Leu
          35                      40                      45

Arg  Asp  Leu  Val  Cys  Tyr  Cys  Arg  Lys  Arg  Gly  Cys  Lys  Arg  Arg  Glu
          50                      55                      60

His  Met  Asn  Gly  Thr  Cys  Arg  Lys  Gly  His  Leu  Leu  Tyr  Thr  Leu  Cys
65                            70                      75                      80

Cys  Arg
```

( 2 ) INFORMATION FOR SEQ ID NO:40:

( i ) SEQUENCE CHARACTERISTICS:
        ( A ) LENGTH: 422 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:40:

```
ACACATTGAG  CTCCTGCTCA  CCAATCCTCC  AGGTGACTCC  CAGCCATGAA  GACACTAGTC        60
```

-continued

| | | | | | |
|---|---|---|---|---|---|
| CTCCTCTCTG | CCCTTGTCCT | GCTGGCCTTC | CAGGTCCAGG | CTGATCCTAT | CCAAAACACA | 120
| GATGAAGAGA | CTAAAACTGA | GGAGCAGCCA | GGGGAAGACG | ACCAGGCCGT | ATCTGTCTCC | 180
| TTTGGAGACC | CAGAAGGCAC | TTCTCTTCAA | GAGGAATCGT | TGAGAGATCT | GGTATGCTAT | 240
| TGTAGATCAA | GAGGCTGCAA | AGGAAGAGAA | CGCATGAATG | GGACCTGCAG | AAAGGGTCAT | 300
| TTATTGTACA | CGCTCTGCTG | TCGCTGAACA | TGGAGACCAC | AGAGGACAAG | ACGAACATGA | 360
| GTACTGAGGC | CACTGATGCT | GGTGCCTGAT | GACCACTTCG | CAATAAATTG | TTCGCAATAT | 420
| GC | | | | | | 422

( 2 ) INFORMATION FOR SEQ ID NO:41:

( i ) SEQUENCE CHARACTERISTICS:
    ( A ) LENGTH: 422 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:41:

| | | | | | |
|---|---|---|---|---|---|
| ACACACTGAG | CCGCTACTCA | CCAATCCTCC | AGGTGACTCC | CAGCCATGAA | GACACTAATC | 60
| CTCCTCTCTG | CCCTCGTCCT | GCTGGCCTTC | CAGGTCCAGG | CTGATCCTAT | CCAAAATACA | 120
| GATGAAGAGA | CTAAAACTGA | GAAGCAGCCA | GGGGAAGAGG | ACCAGGCCGT | ATCTGTCTCC | 180
| TTTGGAGACC | CAGAAGGCTC | TTCTCTTCAA | GAGGAATCGT | TGAGAGATCT | GGTATGCTAT | 240
| TGTAGAACAA | GAGGCTGCAA | AAGAAGAGAA | CGCATGAATG | GGACCTGCAG | AAAGGGTCAT | 300
| TTAATGTACA | CGCTCTGCTG | TCGCTGAACA | TGGAGACCAC | AGAGGACAAG | ATGACCATGA | 360
| GTACTGAGGC | CACTGATGCT | GGTGCCTGAT | GACCACTTCG | CAATAAATTG | CTTGCAATAT | 420
| GC | | | | | | 422

( 2 ) INFORMATION FOR SEQ ID NO:42:

( i ) SEQUENCE CHARACTERISTICS:
    ( A ) LENGTH: 422 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:42:

| | | | | | |
|---|---|---|---|---|---|
| ACACATTGGG | CTCCTGCTCA | CCAATCCTCC | AGGTGACTCC | CAGCCATGAA | GACACTAGTC | 60
| CTCCTCTCTG | CCCTCGTCCT | GCTGGCCTTC | CAGGTCCAGG | CTGATCCTAT | CCAAAACACA | 120
| GATGAAGAGA | CTAAAACTGA | GGAGCAGCCA | GGGGAAGACG | ACCAGGCCGT | ATCTGTCTCC | 180
| TTTGGAGACC | CAGAAGGCTC | TTCTCTTCAA | GAGGAATCGT | TGAGAGATCT | GGTATGCTAT | 240
| TGTAGAAAAA | GAGGCTGCAA | AAGAAGAGAA | CGCATGAATG | GGACCTGCAG | AAAGGGTCAT | 300
| TTAATGTACA | CACTCTGCTG | TCGCTGAACA | TGGAGACCAC | AGAGGACAAG | ACGAACATGA | 360
| GTACTGAGGC | CACTGATGCT | GGTGCCTGAT | GACCACTTCG | CAATAAATTG | TTCGCAATAT | 420
| GC | | | | | | 422

( 2 ) INFORMATION FOR SEQ ID NO:43:

( i ) SEQUENCE CHARACTERISTICS:
    ( A ) LENGTH: 365 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:43:

| | | | | | |
|---|---|---|---|---|---|
| ACTAGTCCTC | CTCTCTGCCC | TCGTCCTGCT | GGCCTTCCAG | GTCCAGGCTG | ATCCTATCCA | 60

| | | | | | |
|---|---|---|---|---|---|
| AAATACAGAT | GAAGAGACTA | AAACTGAGGA | GCAGCCAGGG | GAAGAGGACC | AGGCCGTATC | 120
| TGTCTCCTTT | GGAGACCCAG | AAGGCTCTGC | TCTTCATGAA | AAATCTTTGA | GAGGTTTGTT | 180
| ATGCTATTGT | AGAAAAGGAC | ACTGCAAAAG | AGGAGAACGA | GTTCGTGGGA | CTTGTGGAAT | 240
| ACGATTTTTG | TACTGCTGCC | CCCGCCGCTG | AACATGCAGA | TGACAAAGAT | ATGACAACCA | 300
| TTGTCTCTGA | GGCCGCTGAT | GCCGGGGCCT | GATGACCACT | TCTCAAGAAA | TGTTTGCAAT | 360
| ATGCA | | | | | | 365

( 2 ) INFORMATION FOR SEQ ID NO:44:

( i ) SEQUENCE CHARACTERISTICS:
            ( A ) LENGTH: 421 base pairs
            ( B ) TYPE: nucleic acid
            ( C ) STRANDEDNESS: double
            ( D ) TOPOLOGY: linear ( x i ) SEQUENCE DESCRIPTION: SEQ ID NO:44:

| | | | | | |
|---|---|---|---|---|---|
| ACACATTGGG | CTCCTGCTCA | CCAATTCTCC | AGGTGACCCC | CAGCCATGAA | GACATTTGTC | 60
| CTCCTCTCTG | CCCTTGTCCT | GCTGGCCTTC | CAGGTCCAGG | CTGATCCTAT | CCACAAAACA | 120
| GATGAAGAGA | CTAATACTGA | GGAGCAGCCA | GGGGAAGAGG | ACCAGGCCGT | ATCTATCTCC | 180
| TTTGGAGGCC | AAGAAGGGTC | TGCTCTTCAT | GAGGAATTGT | CAAAAAAGCT | GATATGCTAT | 240
| TGTAGAATAA | GAGGCTGCAA | AAGAAGAGAA | CGCGTTTTTG | GGACCTGCAG | AAATCTTTTT | 300
| TTAACTTTCG | TATTCTGCTG | CAGCTGAATA | TGCAGATGAC | AAAGATATGA | CAACCATCAG | 360
| CACTGAGGCC | ACTGATGCTG | GGGTCTGATG | ATCACCTCGC | AATAAATTGT | TCGCAATATG | 420
| C | | | | | | 421

( 2 ) INFORMATION FOR SEQ ID NO:45:

( i ) SEQUENCE CHARACTERISTICS:
            ( A ) LENGTH: 422 base pairs
            ( B ) TYPE: nucleic acid
            ( C ) STRANDEDNESS: double
            ( D ) TOPOLOGY: linear ( x i ) SEQUENCE DESCRIPTION: SEQ ID NO:45:

| | | | | | |
|---|---|---|---|---|---|
| ACACACTGAG | CTGCTACTCA | CCAATCCTCC | AGGTGACTCC | CAGCCATGAA | GACACTAATC | 60
| CTCCTCTCTG | CCCTCGTCCT | GCTGGCCTTC | CAGGTCCAGG | CTGATCCTAT | CCAAAATACA | 120
| GATGAAGAGA | CTAAAACTGA | GGAGCAGCCA | GGGGAAGAGG | ACCAGGCCGT | ATCTGTCTCC | 180
| TTTGGAGACC | CAGAAGGCAC | TTCTCTTCAA | GAGGAATCAT | TGAGATATCT | GGTATGCTAT | 240
| TGTAGAGCAA | GAGGCTGCAA | AGGAAGAGAA | CGCATGAATG | GGACCTGCAG | AAAGGGTCAT | 300
| TTATTGTACA | TGCTCTGCTG | TCGCTGAACA | TGGAGACCTC | AGAGAACAAG | ACGACCATGA | 360
| GTACTGAGGC | CACTGATGCT | GGTGCCTGAT | GACCACTTCG | CAATACATTG | TTCGCAATAT | 420
| GC | | | | | | 422

( 2 ) INFORMATION FOR SEQ ID NO:46:

( i ) SEQUENCE CHARACTERISTICS:
            ( A ) LENGTH: 420 base pairs
            ( B ) TYPE: nucleic acid
            ( C ) STRANDEDNESS: double
            ( D ) TOPOLOGY: linear ( x i ) SEQUENCE DESCRIPTION: SEQ ID NO:46:

| | | | | | |
|---|---|---|---|---|---|
| ACACTGAGCT | GCTACTCACC | AATCCTCCAG | GTGACTCCCA | GCCATGAAGA | CACTAATCCT | 60

-continued

| CCTCTCTGCC | CTCGTCCTGC | TGGCCTTCCA | GGTCCAGGCT | GATCCTATCC | AAAACACAGA | 120 |
| TGAAGAGACT | AAAACTGAGG | AGCAGCCAGG | GGAAGACGAC | CAGGCCGTAT | CTGTCTCCTT | 180 |
| TGGAGACCCA | GAAGGCTCTT | CTCTTCAAGA | GGAATCGTTG | AGAGATCTGG | TATGCTATTG | 240 |
| TAGAACAAGA | GGCTGCAAAA | GAAGAGAACA | CATGAATGGG | ACCTGCAGAA | AGGGTCATTT | 300 |
| AATGTACACG | CTCTGCTGTC | GCTGAACATG | GAGACCTCAG | AGAACAAGAC | GACCATGAGT | 360 |
| ACTGAGGCCA | CTGATGCTGG | TGCCTGATGA | CCACTTCGCA | ATAAATTGTT | CGCAATATGC | 420 |

(2) INFORMATION FOR SEQ ID NO:47:

(i) SEQUENCE CHARACTERISTICS:
        (A) LENGTH: 342 base pairs
        (B) TYPE: nucleic acid
        (C) STRANDEDNESS: double
        (D) TOPOLOGY: linear (xi) SEQUENCE DESCRIPTION: SEQ ID NO:47:

| GCTGGCCTTC | CAGGTCCAGG | CTGATCCTAT | CCAAAACACA | GATGAAGAGA | CTAAAACTGA | 60 |
| GGAGCAGCCA | GGGGAAGACG | ACCAGGCCGT | ATCTGTCTCC | TTTGGAGACC | CAGAAGGCTC | 120 |
| TTCTCTTCAA | GAGGAATCGT | TGAGAGATCT | GGTATGCTAT | TGTAGAAAAA | GAGGCTGCAA | 180 |
| AAGAAGAGAA | CACATGAATG | GGACCTGCAG | AAAGGGTCAT | TTAATGTACA | CGCTCTGCTG | 240 |
| TCGCTGAACA | TGGAGACCAC | AGAGGACAAG | ACAAGCATGA | GTACTGAGGC | CACTGATGCT | 300 |
| GGTGCCTGAT | GACCACTTCG | CAATAAATTG | TTCGCAATAT | GC | | 342 |

(2) INFORMATION FOR SEQ ID NO:48:

(i) SEQUENCE CHARACTERISTICS:
        (A) LENGTH: 377 base pairs
        (B) TYPE: nucleic acid
        (C) STRANDEDNESS: double
        (D) TOPOLOGY: linear (xi) SEQUENCE DESCRIPTION: SEQ ID NO:48:

| ATGAAGACAC | TAGTCCTCCT | CTCTGCCCTC | GTCCTGCTGG | CCTTCCAGGT | CCAGGCTGAT | 60 |
| CCTATCCAAA | ACACAGATGA | AGAGACTAAA | ACTGAGGAGC | AGCCAGGGGA | AGAGGACCAG | 120 |
| GCCGTATCTG | TCTCCTTTGG | AGACCCAGAA | GGCTCTTCTC | TTCAAGAGGA | ATCGTTGAGA | 180 |
| GATCTGGTAT | GCTATTGTAG | AAAAGAGGC | TGCAAAAGAA | GAGAACACAT | GAATGGGACC | 240 |
| TGCAGAAAGG | GTCATTTATT | GTACATGCTC | TGCTGTCGCT | GAACATGGAG | ACCACAGAGG | 300 |
| ACAAGATGAA | CATGAGTACT | GAGGCCACTG | ATGCTGGTGC | CTGATGACCA | CTTCGCAATA | 360 |
| AATTGTTCGC | AATATGC | | | | | 377 |

(2) INFORMATION FOR SEQ ID NO:49:

(i) SEQUENCE CHARACTERISTICS:
        (A) LENGTH: 375 base pairs
        (B) TYPE: nucleic acid
        (C) STRANDEDNESS: double
        (D) TOPOLOGY: linear (xi) SEQUENCE DESCRIPTION: SEQ ID NO:49:

| GAAGACACTA | GTCCTCCTCT | CTGCCCTCGT | CCTGCTGGCC | TTCCAGGTCC | AGGCTGATCC | 60 |
| TATCCAAAAC | ACAGATGAAG | AGACTAAAAC | TGAGGAGCAG | CCAGGGGAAG | ACGACCAGGC | 120 |
| CGTATCTGTC | TCCTTTGGAG | ACCCAGAAGG | CTCTTCTCTT | CAAGAGGAAT | CGTTGAGAGA | 180 |
| TCTGGTATGC | TATTGTAGAA | AAAGAGGCTG | CAAAGGAAGA | GAACGCATGA | ATGGAACCTG | 240 |
| CAGAAAGGGT | CATTTATTGT | ACACGCTCTG | CTGTCGCTGA | ACATGGAGAC | CACAGAGGAC | 300 |

( 2 ) INFORMATION FOR SEQ ID NO:50:

( i ) SEQUENCE CHARACTERISTICS:
        ( A ) LENGTH: 352 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:50:

```
AAGACGAACA TGAGTACTGA GGCCACTGAT GCTGGTGCCT GATGACCACT TCGCAATAAA    360
TTGTTCGCAA TATGC                                                     375
```

( 2 ) INFORMATION FOR SEQ ID NO:50:

( i ) SEQUENCE CHARACTERISTICS:
        ( A ) LENGTH: 352 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:50:

```
CCCTCGTCCT GCTGGCCTTC CAGGTCCAGG CTGATCCTAT CCAAAACACA GATGAAGAGA     60
CTAAAACTGA GGAGCAGCCA GGGGAAGAGG ACCAGGCCGT ATCTGTCTCC TTTGGAGACC    120
CAGAAGGCAC TTCTCTTCAA GAGGAATCGT TGAGAGATCT GGTATGCTAT TGTAGATCAA    180
GAGGCTGCAA AGGAAGAGAA CGCATGAATG GAACCTGCAG AAAGGGTCAT TTATTGTACA    240
TGCTCTGCTG TCGCTGAACA TGGAGACCAC AGAGAACAAG ACGACCATGA GTACTGAGGC    300
CACTGATGCT GGTGCCTGAT GACCACTTCG CAATACATTG TTCGCAATAT GC            352
```

( 2 ) INFORMATION FOR SEQ ID NO:51:

( i ) SEQUENCE CHARACTERISTICS:
        ( A ) LENGTH: 422 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:51:

```
ACACATTGGG CTCCTGCTCA CCAATCCTCC AGGTGACTCC CAGCCATGAA GACACTAGTC     60
CTCCTCTCTG CCCTCGTCCT GCTGGCCTTC CAGGTCCAGG CTGATCCTAT CCAAAACACA    120
GATGAAGAGA CTAAAACTGA GGAGCAGCCA GGGGAAGAGG ACCAGGCCGT ATCTGTCTCC    180
TTTGGAGACC CAGAAGGCAC TTCTCTCCAA GAGGAATAGT TGAGAGATCT GGTATGCTAT    240
TGTAGAGCAA GAGGCTGCAA AGGAAGAGAA CGCATGAATG GGACCTGCAG AAAGGGTCAT    300
TTAATGTACA CGCTCTGCTG TCGCTGAACA TGGAGACCTC AGAGAACAAG ACGACCATGA    360
GTACTGAGGC CACTGATGCT GGTGCCTGAT GACCACTTCG CAATAAATTG TTCGCAATAT    420
GC                                                                   422
```

( 2 ) INFORMATION FOR SEQ ID NO:52:

( i ) SEQUENCE CHARACTERISTICS:
        ( A ) LENGTH: 388 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:52:

```
GACTCCCAGC CATGAAGACA CTAGTCCTCC TCTCTGCCCT TGTCCTGCTG GCCTTCCAGG     60
TCCAGGCTGA TCCTATCCAA AACACAGATG AAGAGACTAA AACTGAGGAG CAGCCAGGAG    120
AAGAGGACCA GGCCGTATCT GTCTCCTTTG GAGACCCAGA AGGCACTTCT CTTCAAGAGG    180
AATCGTTGAG AGATCTGGTA TGCTATTGTA GAAAAGAGG CTGCAAAAGA AGAGAACACA    240
TGAATGGGAC CTGCAGAAGG GGTCATTTAA TGTACACACT CTGCTGTCGC TGAACATGGA    300
GACCACAGAG GACAAGACGA ACATGAGTAC TGAGGCCACT GATGCTGGTG CCTGATGACC    360
ACCTCGCAAT AAATTGTTCG CAATATGC                                       388
```

( 2 ) INFORMATION FOR SEQ ID NO:53:

( i ) SEQUENCE CHARACTERISTICS:
        ( A ) LENGTH: 352 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:53:

| | | | | | | |
|---|---|---|---|---|---|---|
| CCCTCGTCCT | GCTGGCCTTC | CAGGTCCAGG | CTGATCCTAT | CCAAAACACA | GATGAAGAGA | 60 |
| CTAAAACTGA | GGAGCAGCCA | GGGGAAGAGG | ACCAGGCCGT | ATCTGTCTCC | TTTGGAGACC | 120 |
| CAGAAGGCTC | TTCTCTTCAA | GAGGAATCGT | TGAGAGATCT | GGTATGCTAT | TGTAGAACAA | 180 |
| GAGGCTGCAA | AAGAAGAGAA | CGCATGAATG | GGACCTGCAG | AAAGGGTCAT | TTAATGCACA | 240 |
| CGCTCTGCTG | TCGCTGAACA | TGGAGACCAC | AGAGGACAAG | ACGAGCATGA | GTACTGAGGC | 300 |
| CACTGATGCT | GGTGCCTGAT | GACCACTTCG | CAATAAATTG | TTCGCAAAAT | GC | 352 |

( 2 ) INFORMATION FOR SEQ ID NO:54:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:54:

| | | | | | | |
|---|---|---|---|---|---|---|
| CCAATCCTCC | CAGTGACTCC | CAGCCATGAA | GACACTAGTC | CTCCTCTCTG | CCCTTGTCCT | 60 |
| GCTGGCCTTC | CAGGTCCAGG | CTGATCCTAT | CCAAAACACA | GATGAAGAGA | CTAAAACTGA | 120 |
| GGAGCAGCCA | GGGGAAGACG | ACCAGGCCGT | ATCTGTCTCC | TTTGGAGACC | CAGAAGGCTC | 180 |
| TTCTCTTCAA | GAGGAATCGT | TGAGAGATCT | GGTATGCTAT | TGTAGAAAAA | GAGGCTGCAA | 240 |
| AAGAAGAGAA | CACATAAATG | GGACCTGCAG | AAAGGGTCAT | TTATTGTACA | CTCTCTGCTG | 300 |
| TCGCTGAACA | TGGAGACCAC | AGAGGACAAG | ATGACCATGA | GTACTGAGGC | CACTGATGCT | 360 |
| GGTGCCTGAT | GACCACTCGC | AATAAATTGT | TCGCAATATG | C | | 401 |

( 2 ) INFORMATION FOR SEQ ID NO:55:

( i ) SEQUENCE CHARACTERISTICS:
        ( A ) LENGTH: 391 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:55:

| | | | | | | |
|---|---|---|---|---|---|---|
| GGTGACTCCC | AGCCATGAAG | ACACTAATCC | TCCTCTCTGC | CCTCGTCCTG | CTGGCCTTCC | 60 |
| AGGTCCAGGC | TGATCCTATC | CAAAACACAG | ATGAAGAGAC | TAAAACTGAG | GAGCAGCCAG | 120 |
| GAGAAGAGGA | CCAGGCCGTA | TCTGTCTCCT | TTGGAGACCC | AGAAGGCACT | TCTCTTCAAG | 180 |
| AGGAATCGTT | GAGAGATCTG | GTATGCTATT | GTAGATCAAG | AGGCTGCAAA | GGAAGAGAAC | 240 |
| GCATGAATGG | GACCTGCAGA | AAGGGTCATT | TAATGTACAC | GCTCTGCTGT | CGCTGAACAT | 300 |
| GGAGACCTCA | GAGAACAAGA | CGACCATGAG | TACTGAGGCC | ACTGATGCTG | GTGCCTGATG | 360 |
| ACCACTTCGC | AATAAATTGT | TCGCAATATG | C | | | 391 |

( 2 ) INFORMATION FOR SEQ ID NO:56:

( i ) SEQUENCE CHARACTERISTICS:
        ( A ) LENGTH: 342 base pairs
        ( B ) TYPE: nucleic acid
        ( C ) STRANDEDNESS: double ( D ) TOPOLOGY: linear ( x i ) SEQUENCE DESCRIPTION: SEQ ID NO:56:

| | | | | | | |
|---|---|---|---|---|---|---|
| GCTGGCCTTC | CAGGTCCAGG | CTGATCCTAT | CCAAAATACA | GATGAAGAGA | CTAAAACTGA | 60 |
| GGAGCAGCCA | GGAGAAGAGG | ACCAGGCCGT | ATCTGTCTCC | TTTGGAGACC | CAGAAGGCAC | 120 |
| TTCTCTTCAA | GAGGAATCGT | TGAGAGATCT | GGTATGCTAT | TGTAGAAAAA | GAGGCTGCAA | 180 |
| AAGAAGAGAA | CACATGAATG | GGACCTGCAG | AAAGGGTCAT | TTATTGTACA | CGCTCTGCTG | 240 |
| TCGCTGAACA | TGGAGACCAC | AGAGGACAAG | ATGACCATGA | GTACTGAGGC | CACTGATGCT | 300 |
| GGTGCCTGAT | GACCACCTCG | CAATAAATTG | CTTGCAATAT | GC | | 342 |

( 2 ) INFORMATION FOR SEQ ID NO:57:

( i ) SEQUENCE CHARACTERISTICS:
        ( A ) LENGTH: 403 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:57:

| | | | | | | |
|---|---|---|---|---|---|---|
| ACACATGGCT | CTCTCACCAA | TCCTCCAGGT | GACTCCCAGC | CATGAAGACA | CTAGTCCTCC | 60 |
| TCTCTGCCTG | TCCTGCTGGC | CTTCCAGGTC | CAGGCTGATC | CTATCCAAAA | CACAGATGAA | 120 |
| GAGACTAAAA | CTGAGGAGCA | GCCAGGGGAA | GAGACCAGGC | TGTGTCTGTC | TCTTTTGGAG | 180 |
| ACCCAGAAGG | CCTTCTCTTC | AAGAGGAATC | GTTGAGAGAT | CTGGTATGCT | ATTGTAGAAA | 240 |
| GAGGCTGCAA | AGAAGAGAAC | CATGAATGGG | ACCTGCAGAA | AGGGTCATTT | ATGTACAGCT | 300 |
| CTGCTGTCGC | TGAACATGGA | GACCCAGAGA | CAAGAACATG | AGTACTGAGG | CCACTGATGC | 360 |
| TGGTGCCTGA | TGACCACTTC | TCAATAAATT | GTTCGCAATA | TGC | | 403 |

( 2 ) INFORMATION FOR SEQ ID NO:58:

( i ) SEQUENCE CHARACTERISTICS:
        ( A ) LENGTH: 419 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 279..286
        ( D ) OTHER INFORMATION: /note= "N represents DNA that was
                not sequenced."

( x i ) SEQUENCE DESCRIPTION: SEQ ID NO:58:

| | | | | | | |
|---|---|---|---|---|---|---|
| TATAAATGCA | GGCTGGATAT | TCACTGTCCA | CACATTGAGC | TCCTGCTCAC | CAATCCTCCA | 60 |
| GGTGACTCCC | AGCCATGAAG | ACACTAGTCC | TCCTCTCTGC | CCTTGTCCTG | CTGGCCTTCC | 120 |
| AGGTCCAGGC | TGATCCTATC | CAAAACACAG | ATGAAGAGAC | TAAAACTGAG | GAGCAGCCAG | 180 |
| GAGAAGAGGA | CCAGGCCGTA | TCTGTCTCCT | TTGGAGACCC | AGAAGGCACT | TCTCTTCAAG | 240 |
| AGGAATGTGA | GTACTGGTGT | CCAGAGTGAT | GGATGCTTNN | NNNNNTTTT | GTATCTCCAG | 300 |
| CGTTGAGAGA | TCTGGTATGC | TATTGTAGAT | CAAGAGGCTG | CAAAGGAAGA | GAACGCATGA | 360 |
| ATGGAACCTG | CAGAAAGGGT | CATTTATTGT | ACACGCTCTG | CTGTCGCTGA | ACATGGAGA | 419 |

( 2 ) INFORMATION FOR SEQ ID NO:59:

( i ) SEQUENCE CHARACTERISTICS:
        ( A ) LENGTH: 419 base pairs
        ( B ) TYPE: nucleic acid
        ( C ) STRANDEDNESS: single
        ( D ) TOPOLOGY: linear ( i x ) FEATURE:
  ( A ) NAME/KEY: misc_feature
  ( B ) LOCATION: 279..286
  ( D ) OTHER INFORMATION: /note= "N represents DNA that was
    not sequenced."

( x i ) SEQUENCE DESCRIPTION: SEQ ID NO:59:

| | | | | | | |
|---|---|---|---|---|---|---|
| TATAAATGCA | GACTGGCTCC | TCACTCTCCA | CACATTGGGC | TCCTGCTCAC | CAATCCTCCC | 60 |
| AGTGACTCCC | AGCCATGAAG | CCACTTGTCC | TCCTTTCTGC | CCTTGTCCTA | CTGTCCTTTC | 120 |
| AGGTCCAGGC | TGATCCTATC | CAAAACACAG | ATGAAGAGAC | TAAAACTGAG | GAGCAGTCAG | 180 |
| GTGAAGAGGA | CCAGGCTGTG | TCTGTCTCCT | TTGGAGACCG | AGAAGGCGCT | TCTCTTCAAG | 240 |
| AAGAATGTGA | GTACTGGTGC | CCAGTGTGAT | GGATGCTTNN | NNNNNTTTT | GTGTCTCCAG | 300 |
| CGTTGAGAGA | TCTGGTATGC | TATTGTAGAA | CAAGAGGTTG | CAAAAGAAGA | GAACGCATGA | 360 |
| ATGGGACCTG | CAGAAAGGGT | CATTTAATGT | ACACGCTCTG | CTGCCGCTGA | ACATGGAGA | 419 |

( 2 ) INFORMATION FOR SEQ ID NO:60:

( i ) SEQUENCE CHARACTERISTICS:
    ( A ) LENGTH: 419 base pairs
    ( B ) TYPE: nucleic acid
    ( C ) STRANDEDNESS: single
    ( D ) TOPOLOGY: linear ( i x ) FEATURE:
    ( A ) NAME/KEY: misc_feature
    ( B ) LOCATION: 279..286
    ( D ) OTHER INFORMATION: /note= "N represents DNA that was
      not sequenced."

( x i ) SEQUENCE DESCRIPTION: SEQ ID NO:60:

| | | | | | | |
|---|---|---|---|---|---|---|
| TATAAATGCA | GGCTGGATAT | TCACTCTCCA | CACATTGGGC | TCCTGCTCAC | CAATCCTCCA | 60 |
| GGTGACTCCC | AGCCATGAAG | ACACTAGTCC | TCCTCTCTGC | CCTCGTCCTG | CTGGCCTTCC | 120 |
| AGGTCCAGGC | TGATCCTATC | CAAAACACAG | ATGAAGAGAC | TAAAACTGAG | GAGCAGCCAG | 180 |
| GGGAAGACGA | CCAGGCTGTG | TCTGTCTCTT | TTGGAGACCC | AGAAGGCTCT | TCTCTTCAAG | 240 |
| AGGAATGTGA | GTATTGGTGT | CCTGTGTGAT | GGATGCTTNN | NNNNNTTTT | GTGTCTCCAG | 300 |
| CGTTGAGAGA | TCTGGTATGC | TATTGTAGAA | AAAGAGGCTG | CAAAAGAAGA | GAACGCATGA | 360 |
| ATGGGACCTG | CAGAAAGGGT | CATTTAATGT | ACACACTCTG | CTGTCGCTGA | ACATGGAGA | 419 |

( 2 ) INFORMATION FOR SEQ ID NO:61:

( i ) SEQUENCE CHARACTERISTICS:
    ( A ) LENGTH: 419 base pairs
    ( B ) TYPE: nucleic acid
    ( C ) STRANDEDNESS: single
    ( D ) TOPOLOGY: linear ( i x ) FEATURE:
    ( A ) NAME/KEY: misc_feature
    ( B ) LOCATION: 279..286
    ( D ) OTHER INFORMATION: /note= "N represents DNA that was
      not sequenced."

( x i ) SEQUENCE DESCRIPTION: SEQ ID NO:61:

| | | | | | | |
|---|---|---|---|---|---|---|
| TATAAATGCA | AGTTGGCTAC | TCACTCTCCA | CACATTGGGC | TCCTGCTCAC | CAATTCTCCA | 60 |
| GGTGACCCCC | AGCCATGAAG | ACATTTGTCC | TCCTCTCTGC | CCTTGTCCTG | CTGGCCTTCC | 120 |
| AGGTCCAGGC | TGATCCTATC | CACAAACAG | ATGAAGAGAC | TAATACTGAG | GAGCAGCCAG | 180 |
| GGGAAGAGGA | CCAGGCTGTG | TCAGTCTCCT | TTGGAGGCCA | AGAAGGGTCT | GCTCTTCATG | 240 |
| AAGAATGTGA | GTAGTGGTAC | GCAGTGTGAT | GGATGCTTNN | NNNNNTTTT | GTGTCTCCAG | 300 |

```
TGTCAAAAAA  GCTGATATGC  TATTGTAGAA  TAAGAGGCTG  CAAAAGAAGA  GAACGCGTTT        360

TTGGGACCTG  CAGAAATCTT  TTTTTAACTT  TCGTATTCTG  CTGTAGCTGA  ATATGCAGA         419
```

( 2 ) INFORMATION FOR SEQ ID NO:62:

( i ) SEQUENCE CHARACTERISTICS:
        ( A ) LENGTH: 419 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 279..286
        ( D ) OTHER INFORMATION: /note= "N represents DNA that was
            not sequenced."

( x i ) SEQUENCE DESCRIPTION: SEQ ID NO:62:

```
TATAAATGCA  GGCTGGATAT  TCACTCTCCA  CACACTGAGC  TGCTACTCAC  CAATCCTCCA         60

GGTGACTCCC  AGCCATGAAG  ACACTAATCC  TCCTCTCTGC  CCTCGTCCTG  CTGGCCTTCC        120

AGGTCCAGGC  TGATCCTATC  CAAAATACAG  ATGAAGAGAC  TAAAACTGAG  GAGCAGCCAG        180

GGGAAGAGGA  CCAGGCTGTG  TCTGTCTCTT  TTGGAGACCC  AGAAGGCACT  TCTCTTCAAG        240

AGGAATGTGA  GTACTGGTGT  CCAGTGTGAT  GGATGCTTNN  NNNNNTTTT   GTGTCTCCAG        300

CATTGAGAGA  TCTGGTATGC  TATTGTAGAG  CAAGAGGCTG  CAAAGGAAGA  GAACGCATGA        360

ATGGGACCTG  CAGAAAGGGT  CATTTATTGT  ACATGCTCTG  CTGTCGCTGA  ACATGGAGA         419
```

( 2 ) INFORMATION FOR SEQ ID NO:63:

( i ) SEQUENCE CHARACTERISTICS:
        ( A ) LENGTH: 419 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 279..286
        ( D ) OTHER INFORMATION: /note= "N represents DNA that was
            not sequenced."

( x i ) SEQUENCE DESCRIPTION: SEQ ID NO:63:

```
ACTTGAGGGT  AACAGCCTCT  CCCAATTCCA  CACATTGAGC  TCCTGCTCAC  CAATCCTCCA         60

GGTGACTCCC  AGCCATGAAG  ACACTAGTCC  TCCTCTCTGC  CCTTGCCCTG  CTGGCCTTCC        120

AAGTCCAGGC  TGATCCTATC  CAAAACACAG  ATGAAGAGAC  TAAAACTGAG  GAGCAGCCAG        180

GGAAAGAAGA  CCAAGCTGTT  TCTGTCTCCT  TTGGAGACCC  AGAAGGCTCT  TCTCTTCAAG        240

AGGAATGTGA  GTACTGGTGC  CCAGTGTGAT  GGATGCTTNN  NNNNNTTTT   GTGTCTCCAG        300

CGTTGAGAGA  TCTGATATGA  TATTGTAGAA  CAAGAGGCTG  CAAAAGAAGA  GAACGCCTGA        360

ATGGGACCTG  AAGAAAGGGT  CATTTATTGT  ACATGCTCTG  CTGCTGCTGA  ACATGGAGA         419
```

( 2 ) INFORMATION FOR SEQ ID NO:64:

( i ) SEQUENCE CHARACTERISTICS:
        ( A ) LENGTH: 411 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:64:

```
TATAAATGCA  RRCTGGMTMY  TCACTNTCCA  CACATTGRGC  TCCTGCTCAC  CAATCCTCCA         60
```

| | | | | | |
|---|---|---|---|---|---|
| GGTGACTCCC | AGCCATGAAG | ACACTWGTCC | TCCTCTCTGC | CCTYGTCCTG | CTGGCCTTCC | 120 |
| AGGTCCAGGC | TGATCCTATC | CAAAAHACAG | ATGAAGAGAC | TAAAACTGAG | GAGCAGCCAG | 180 |
| GDGAAGARGA | CCAGGCTGTD | TCTGTCTCYT | TTGGAGACCV | AGAAGGCDCT | TCTCTTCAAG | 240 |
| ARGAATGTGA | GTABTGGTGY | CCAGTGTGAT | GGATGCTTTT | TTGTGTCTCC | AGCGTTGAGA | 300 |
| GATCTGRTAT | GCTATTGTAG | ADHAAGAGGC | TGCAAARGAA | GAGAACGCVT | GAATGGGACC | 360 |
| TGCAGAAAGG | GTCATTTAWT | GTACANNCTC | TGCTGYRGCT | GAACATGGAG | A | 411 |

(2) INFORMATION FOR SEQ ID NO:65:

(i) SEQUENCE CHARACTERISTICS:
        (A) LENGTH: 445 base pairs
        (B) TYPE: nucleic acid
        (C) STRANDEDNESS: double
        (D) TOPOLOGY: linear (xi) SEQUENCE DESCRIPTION: SEQ ID NO:65:

| | | | | | |
|---|---|---|---|---|---|
| ACACTGGTCT | CCAGCTCACC | AATCCTCCAG | GTGACTTCCA | GCCATGAAGA | CTCTTGTCCT | 60 |
| CCTCTCTGCC | CTTGTCCTGC | TGGCATTCCA | GGTCCAGGCT | GATCCCATTC | AAGAGGCAGA | 120 |
| AGAAGAGACT | AAAACTGAGG | AGCAGCCAGC | AGATGAGGAC | CAGGATGTGT | CTGTCTCCTT | 180 |
| TGAAGGCCCA | GAACCCTCTG | CTCTTCAAAA | TTTAGAGATA | GGATGGCCAT | TAAAGCAGTG | 240 |
| CCATTGCCGA | AAGTTCTGCA | GACCTTATGA | AAAGGCCGAG | GGGTCCTGTC | GTCCAGGTCT | 300 |
| ATTTATAAAA | CGCAAAATCT | GCTGCATACA | ACAATGGACA | CCAGGGAGGA | CATAACCACG | 360 |
| TGAACTGGGA | CCTCACAATC | TGTCATTCTT | GGGCTTCAAC | TCGACTGCTT | TTCCTTCTCC | 420 |
| AATAAACCCC | TTGCAGACAA | AAAAA | | | | 445 |

(2) INFORMATION FOR SEQ ID NO:66:

(i) SEQUENCE CHARACTERISTICS:
        (A) LENGTH: 445 base pairs
        (B) TYPE: nucleic acid
        (C) STRANDEDNESS: double
        (D) TOPOLOGY: linear (xi) SEQUENCE DESCRIPTION: SEQ ID NO:66:

| | | | | | |
|---|---|---|---|---|---|
| ACACTGGTCT | CCAGCTCACC | AATCCTCCAG | GTGACTTCCA | GCCATGAAGA | CTCTTGTCCT | 60 |
| CCTCTCTGCC | CTTGTCCTGG | TGGCCTACCA | GGTCCAGGCT | GATCCCATTC | AAGGGGCAGA | 120 |
| AGAAGAGACT | AAAACTGAAG | AGCAACCATC | AGATGAGGAC | CAGGATGTGT | CTGTCTCCTT | 180 |
| TGAAGGCCCA | GAAGCCTCTG | CTCTTCAAGA | TTTTGAGATA | GGAAGGCCAG | TGAGGAGGTG | 240 |
| CCGTTGCAGA | GCAAACTGCG | GACCTAAAGA | ATATGCCACT | GCGTTCTGTG | CTCAAGGTCC | 300 |
| ATTTAAACAG | TTCAAATTCT | GCTGCACATG | AACATGGATC | CCAAGTCTGA | GATAACCACG | 360 |
| TGCTCTGGGA | CCTCACAATC | TGTCATTATT | GTGCTTGACC | TCAACTGCTT | TTCCTTCTCC | 420 |
| AATAAACTCC | TGGCAGACAA | AAAAA | | | | 445 |

(2) INFORMATION FOR SEQ ID NO:67:

(i) SEQUENCE CHARACTERISTICS:
        (A) LENGTH: 445 base pairs
        (B) TYPE: nucleic acid
        (C) STRANDEDNESS: double
        (D) TOPOLOGY: linear (xi) SEQUENCE DESCRIPTION: SEQ ID NO:67:

| | | | | | |
|---|---|---|---|---|---|
| ACACTGGTCT | CCAGCTCACC | AATCCTCCAG | GTGACTTCCA | GCCATGAAGA | CTCTTGTCCT | 60 |
| CCTCTCTGCC | CTTGTCCTGC | TGGCATTCCA | GATCCAGGCT | GATCCCATTC | AAGAGGCAGA | 120 |

```
AGAAGAGACT  AAAACTGAGG  AGCAGCCAGC  AGATGAGGAC  CAGGATGTGT  CTGTCTCCTT      180

TGAAGGCCCA  GAACCCTCTG  CTCTTCAAAA  TTTAGAGATC  AGATGGCCAT  GGAAGAGGTG      240

CCATTGCAGA  AGTTTCTGCA  GACCTTATGA  AAATGCCACT  TCGTTCTGTG  CTCAAGGTCT      300

ATTTAAACAA  CACAAATTCT  GCTGCCTAGA  AACATGGCCC  CCAAGGATGA  AATAACCACG      360

TGCTCTGGGA  CCTCACAATC  TGTCATCATT  GTGCTTGGCC  TCAACTTCTT  TTCCTTCTCC      420

AATAAACTCC  TTGCAGACAA  AAAAA                                               445

( 2 ) INFORMATION FOR SEQ ID NO:68:

( i ) SEQUENCE CHARACTERISTICS:
                ( A ) LENGTH: 2457 base pairs
                ( B ) TYPE: nucleic acid
                ( C ) STRANDEDNESS: double
                ( D ) TOPOLOGY: linear ( x i ) SEQUENCE DESCRIPTION: SEQ ID NO:68:

CCTGAGACCA  ACTCTGTGAT  AATCAGAAAA  GTCAATAATG  TGTCTGAAAT  GTAAGGTGTG       60

CTTCTTGACT  GATAGTTCTA  AGCCTACAGA  GAGATTCATG  TGGTCATATC  CCATTTAACA      120

ATGATATATA  TGTTAAATAT  ATAAAGATAT  ATGTATGTTC  AGTATGTATG  TTCAATATGT      180

ATGTAAATAA  TATTCTTGCT  GCTTCACTAG  CTTTTACACA  GAGCTGTAAG  TAAAAACATT      240

GTAGCCAATG  AATAGTATTT  ATTAACATGT  AAATAGGAGC  TGGCACCTGT  GACAGTGGGA      300

CTCCATACAC  TGACTGTAAA  CAACAGGATG  CTCTGGACCT  TTTGCTGTGT  GTGTGGTGAG      360

AGACATGGGA  TAAACACAGA  CTGAAGAGTG  TTCCTGAATG  ACATGGCGGC  ACTTCTCGAG      420

ACCGGGTAGC  AGCTTCTGAG  CCTCTCTACA  TTGTGGATGT  CCTTTCCTGT  AGGTCAGGTC      480

TCATTGTCTA  AAAGTAAAAG  CATTGCAGCA  TCTCAGACCT  GGGAAACACC  CCATGGCTTG      540

AGGGTCCTGA  GCATGAAGAG  CCACCTGGAG  CTCACTCTTG  GCAGATGTGT  TCCATGACTT      600

TGGCTTCTTC  AGAACAACCC  ACTACAGCTT  CACTCTGACA  AATCCTAGAA  ACTTGAACTC      660

AATTCACTAG  AGGGCACCAT  AAAGCCATCA  TACCTTATAA  TGGCCCCAAA  GGAGGTGATT      720

CACAAAGTTT  GCCTTGATGA  GGACAATTGC  TAATACACAA  AAACTTGCAA  AAAAAAATTG      780

AGTGTCCAGT  CCACCTGGTC  AAGGACTGGT  CCCGGATCCA  CAGTTTCTGA  GAATAGCAGG      840

CTCTAACTTG  AAAACACAAA  AATTGTTTGT  TCTATGAGCT  CATTAAATTA  GGCAGTGTTC      900

AGCTATTTTC  TTTCCTGACC  ACTGAGAGGT  AAATACTCAA  GCAGATGGGA  AACAGGGGAG      960

GACAGTAAAG  CCTGTTCATC  ATTATCAGTG  GGAGTGTGCA  TGAGGGGAGG  GGTGTCAGTG     1020

AACACACAGA  GCATCAGGAA  GGAAGCCTTG  AGGACAGAGG  AACATCAAAG  GGATCCTGAG     1080

GACAACAGCT  GGGAGCAGTT  GCCATCAATG  AGTGCCTTCT  CTAAGTATGG  GGCATGTTCT     1140

TTGCCCTATA  AATGCAGGCT  GGCTTCTCTC  TCCACACACT  GGTCTCCAGC  TCACCAATCC     1200

TCCAGGTGAC  TTCCAGCCAT  GAAGACTCTT  GTCCTCCTCT  CTGCCCTTGT  CCTGCTGGCA     1260

TTCCAGGTCC  AGGCTGATCC  CATTCAAGAG  GCAGAAGAAG  AGACTAAAAC  TGAGGAGCAG     1320

CCAGCAGATG  AGGACCAGGA  TGTGTCTGTC  TCCTTTGAAG  GCCCAGAACC  CTCTGCTCTT     1380

CAAAATTTAG  GTGCGTGCTT  GTGCACAGAA  TGATGGAGGC  TTGGAGTCTC  CTGATGGAGG     1440

GTTGTAGATT  AGCCCTGGAG  TCCTGTCAAG  GACAGTCTGG  TTCAGGTAGC  TGTCTACTGA     1500

TCCTTTCAGA  ACTTCCCTGT  CTTATTCATA  GAAATAACAG  TGAGAGACAA  GCCATTGGGC     1560

TTGACTTTTT  CCTTTTAAGA  TTTCGGTCTA  ACAATTTATC  TGTGAAAAAC  CTTTAAAATA     1620

TAAAACATAT  TGATTAGTTC  TTTAAACCTG  AGTGATAATT  TTCTTACAGG  AAGAAATATC     1680
```

| | | | | | | |
|---|---|---|---|---|---|---|
| CGTTTTACCC | TAAAAATTAG | ATTGGTACCC | AAATGCCAGT | GTATGAAGGT | GTTGGGTCAA | 1740 |
| GAAAACACAA | AAAAACTGTT | AGAATATGGT | GTAGATGAAA | ATTCCTATAT | GTGATTAACA | 1800 |
| CTTGTTAAAC | ATCTTATCTC | CATGTGTTTG | GGGTTGATCA | CTGTGCTGGC | TGTGATGTCA | 1860 |
| CCCACACAGC | AAACCTACTC | TCTACCATGC | ACAGGACATC | TTCATGGGGT | AGTTCACTGT | 1920 |
| TACACACTAC | TGGCCTCCTT | ACTTCATGCC | TGATGCTTTC | TTGTTTCCTC | AGAGATAGGA | 1980 |
| TGGCCATTAA | AGCAGTGCCA | TTGCCGAAAG | TTCTGCAGAC | CTTATGAAAA | GGCCGAGGGG | 2040 |
| TCCTGTCGTC | CAGGTCTATT | TATAAACGC | AAAATCTGCT | GCATACAACA | ATGGACACCA | 2100 |
| GGGAGGACAT | AACCACGTGA | ACTGGGACCT | CACAATCTGT | CATTCTTGGG | CTTCAACTCG | 2160 |
| ACTGCTTTC | CTTCTCCAAT | AAACCCCTTG | CAGACAAATA | ACCTGTTTAT | GTTTTTTGA | 2220 |
| TGCTTTCTAT | GTGGCGTAGA | CAGGACTCTC | CTGAGCCATG | TAGCAAAATC | TTCAGTGAAT | 2280 |
| CCTTTGTAAA | AGAAGTCTTG | GTCACATTTC | AGCAGTCATA | TCAAGGATGA | GCAGGAGGTT | 2340 |
| AGATCCAAAG | AGACAAGATG | GTCTGCGCCA | GCTGCTTCTG | TGTCTATCAA | GTCTTCTGTC | 2400 |
| CTTTAGATTA | GAGTCACCCT | CAAAAATTAG | TTCCAGATTT | TCATGTTCTA | TTTTTTC | 2457 |

(2) INFORMATION FOR SEQ ID NO:69:

(i) SEQUENCE CHARACTERISTICS:
        (A) LENGTH: 2408 base pairs
        (B) TYPE: nucleic acid
        (C) STRANDEDNESS: single
        (D) TOPOLOGY: linear (xi) SEQUENCE DESCRIPTION: SEQ ID NO:69:

| | | | | | | |
|---|---|---|---|---|---|---|
| TATTACGAAT | TCGAGCTCGG | TACCGGTATA | TGAAGAGCGA | CCACTGCCAG | GACGAAAGTG | 60 |
| CAATGCGGCA | TACCTCAGTG | GCGTGGAGTG | CAGGTATACA | GATTAATCCG | GCAGCGTCCG | 120 |
| TCGTTGTTGA | TATTGCTTAT | GAAGGCTCCG | GCAGTGGCGA | CTGGCGTACT | GACGGATTCA | 180 |
| TCGTTGGGGT | CGGTTATAAA | TTCTGATTAG | CCAGGTAACA | CAGTGTTATG | ACAGCCGCC | 240 |
| GGAACCGGTG | GGCTTTTTTG | TGGGGTGAAT | ATGGCAGTAA | AGATTTCAGG | AGTCCTGAAA | 300 |
| GACGGCACAG | GAAAACCGGT | ACAGAACTGC | ACCATTCAGC | TGAAAGCCAG | ACGTAACAGC | 360 |
| ACCACGGTGG | TGGTGAACAC | GGTGGGCTCA | GAGAATCCGG | ATGAAGCCTG | CTTTTTTATA | 420 |
| CTAAGTTGGC | ATTATAAAAA | AGCATTGCTT | ATCAATTTGT | TGCAACGAAC | AGGTCACTAT | 480 |
| CAGTCAAAAT | AAAATCATTA | TTTGATTTCA | ATTTGTCCC | ACTCCTGCC | TCTGTCATCA | 540 |
| CGATACTGTG | ATGCCATGGT | GTCCGACTTA | TGCCCGAGAA | GATGTTGAGC | AAACTTATCG | 600 |
| CTTATCTGCT | TCTCATAGAG | TCTTGCAGAC | AAACTGCGCA | ACTCGTGAAA | GGTAGGCGGA | 660 |
| TCTGGGTCGA | CTCTAGGCCT | CACTGGCCTA | ATACGACTCA | CTATAGGGAG | CTCGAGGATC | 720 |
| ATTGCTAATA | CCATGAAACT | TGACCACCTG | GTCAAGGACT | GGTCCAGGGT | CCACAGTTTC | 780 |
| TGAGAAGAGC | AGGCTCCAAC | TTCTAACCAC | AAAAACTATT | TTTTCCATGC | GCTCCTTAAA | 840 |
| TTAGGCAGCG | CCCAGCTATT | TTCTTTCCTG | ACCACTGAGA | GGTAAATACT | CAAGCAGATG | 900 |
| GGAAACAGGG | GAAGATAGCA | AGGCCTCTTC | ATCATTATCA | CTGGGTGTGT | GCGTGAGGGG | 960 |
| AGGGGTGTCA | TTGCATACAC | AGGGCAACAT | CAGGATGGAA | GCCTTGAGGA | CAGAGGAACA | 1020 |
| TCAAAGGGAT | CCTGAGGACA | ACAGCTGGGA | GCAGTTGCCA | TCAGTGAGTG | CCTTCTCTAA | 1080 |
| GTGTGGGGCC | TTTCTCTGCC | ACATAAATGC | AGGCTGCCTC | CTCTCTCCAC | ACACTGGTCT | 1140 |
| CCAGCTCACC | AATCCTCCAG | GTGACTTCCA | GCCATGAAGA | CTCTTGTCCT | CCTCTCTGCC | 1200 |
| CTTGTCCTGG | TGGCCTACCA | GGTCCAGGCT | GATCCCATTC | AAGGGGCAGA | AGAAGAGACT | 1260 |
| AAAACTGAAG | AGCAACCATC | AGATGAGGAC | CAGGATGTGT | CTGTCTCCTT | TGAAGGCCCA | 1320 |

-continued

| | | | | | |
|---|---|---|---|---|---|
| GAAGCCTCTG | CTCTTCAAGA | TTTTGGTGAG | TGCTTATGCA | CAGAATGATG | GAGGCTTGGA | 1380
| GTCTCCTGAT | GGAGGGTTGT | AGATTAGACC | TGGAATCCTG | TCAAGAACTG | TCTGGTTCAG | 1440
| GTAGCTGTCT | CTTGGTCCCT | TTACATTCCT | TGTCTTCTTC | ATAGAAGTAA | CGGAGAGAGA | 1500
| TTAACCATTG | GGCTTGACTT | TTTTCCTTTT | AAAATTTTTG | ATCTAACAAT | TTATCTGTGG | 1560
| AAAACCTTTA | AAATATAAAA | CATATTGATT | AGTTCTTTTA | GACCTGATTG | ATAATTTTGT | 1620
| TATAAGAAGA | AATATTCGTT | CTACTTTAAA | AATTAGATTT | GGGACCCAAA | TGCCAGTGTA | 1680
| TGAAGCTGTT | GGGTAAGGAA | AAACCAAAAA | TGGTGATAGA | ATGTTGTGTA | GATGACAATT | 1740
| CCTTTATGCG | ATTAACACTT | TTTAAAATGT | CTTATCTCCA | TGTGTTTGGG | GTTGATCATG | 1800
| GTGCTGACTG | TGATGTCACC | CACAGAGCAA | ACCTACTCTC | TACCATGCAC | AGGACATCTT | 1860
| CATAGGGTAG | TTCACTGTCA | CACACTGCTG | GCCTCGTTAC | TTCATGCCTG | ATGCTTTCTT | 1920
| GTTTCCTCAG | AGATAGGAAG | GCCAGTGAGG | AGGTGCCGTT | GCAGAGCAAA | CTGCGGACCT | 1980
| AAAGAATATG | CCACTGCGTT | CTGTGCTCAA | GGTCCATTTA | AACAGTTCAA | ATTCTGCTGC | 2040
| ACATGAACAT | GGATCCCAAG | TCTGAGATAA | CCACGTGCTC | TGGGACCTCA | CAATCTGTCA | 2100
| TTATTGTGCT | TGACCTCAAC | TGCTTTTCCT | TCTCCAATAA | ACTCCTGGCA | GACAAATAAT | 2160
| CGGTATATGT | TTATTTGATG | CTTTCTATTT | GGCTTAGACA | GAACTCTCCT | GAGCCATGTA | 2220
| GCTGAATCTT | CAGTGAATCC | TTTGTAAAGG | TCACATTTCA | GCAGTCATAT | CAAGGATGAG | 2280
| CAGGAGGTTA | GATACAAAGA | GACAAGATGG | TCTGCGCCAG | CTGCTTCTTT | GTCTATCAAG | 2340
| TCTGCTTTCC | TTTAGATTAG | AGTCACCATC | AAAAATTATT | CCCACATTTT | CATGTTCTAT | 2400
| ATTTTTTT | | | | | | 2408

( 2 ) INFORMATION FOR SEQ ID NO:70:

( i ) SEQUENCE CHARACTERISTICS:
        ( A ) LENGTH: 2551 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:70:

| | | | | | |
|---|---|---|---|---|---|
| CCTGAGACCA | ACTCTGTGAT | AATCAGAAAA | GACAATTATG | TGTCTTAAAT | GTAAGGTTTG | 60
| CTTCTTGACT | GATAGATCTA | ACCCTACAGA | GAGATTCAAG | TGGTCTTGTC | CCATTGAACA | 120
| ATAGTATATA | TGTTTTATAT | ATATATATAT | ATATATGTAT | ATGTATATAT | ATATGTGTGT | 180
| GTGTGTGTGT | GTGTGTCTGT | GTCTGTGTGT | CTGTGTGTCT | GTGTGTCTGT | GTGTCTGTGT | 240
| GTGTATGTGT | GTGTATGTGT | ACATATGTTC | AATATGTCTG | TAAAATAGTA | TTCTTGTAGC | 300
| TTCACTTACT | TTTGCACAGA | GCTGTAAATA | AGAACATTGT | AGCCAATGAA | TAGTATTTAT | 360
| TAACATGTAA | ATAGGAGCTG | GCACCTCTGA | CAGTGGGACT | CCATACAGTG | ACTGTAAACA | 420
| ACAGGATGCT | CTAGACCTTT | TGCTGTGTGT | GTGGTGAGAG | ACATGGATA | AACACAGACT | 480
| GAAGTGTATG | ACATGGCGGC | ACTTCTCGAG | ACCGGGTAGC | AGCTTCTGAG | CCTCTCTACA | 540
| TTGTGGATGT | CCTTTCCTGT | AGGTCAGGTC | TCATTGTCTA | AAAGTAAAAG | CATTGCAGCA | 600
| TCTCAGACCT | GGGAAACACC | CCATGGCTTG | AGGGTCCCGC | AGGTGAAGAG | CCACCTGGAG | 660
| CTCACTCTTG | GCAGATGTGT | TCCATGACTT | TGGCTTCTTC | AGAACCACCC | ACTACAGCTT | 720
| CACTCTGACA | AATCTTAGAA | ACTTGAACTC | AATTCACTGG | AGGGCACAAT | AAAGCCATCT | 780
| TACTTTCTCT | AAAATGGCCC | CAAAGGAGGG | GATTCACAAA | GTTTGCCTTG | ATGAGGACCA | 840
| TTGCTAATAC | CCCAAAACTT | GCAAAAAAAA | TTGAGTGTCC | AGTCAACCTG | GTCAAGGACT | 900

| | | | | | |
|---|---|---|---|---|---|
| GGTCCTGGAT | CCACAGTTTC | TGAGAAAAGA | AGGCTCCAAC | TTCAAAACAC | AAACCACTCC 960 |
| TGTTCTATGC | GCTCATTAAA | TTAGGCAGTG | TTAAGCTATT | TTCTTTCCTG | ACCACTGAGA 1020 |
| GGTAAATACT | CAAGCAGATG | GGAAACAGGG | GAGGACAGCA | AAGCCTGTTC | ATCATTATCA 1080 |
| GTGGGAGTGT | GCGTGAGGGG | AGGGGTGTCA | GTGAACACAC | AGAGCATCAG | GAAGGAAGCC 1140 |
| TTGAGGACAG | AGGAACATCA | AAGGGATCCT | GAGGACAACA | GCTGGGAGCA | GTTGGCATCA 1200 |
| CTGAGTGCCG | TCTCTAAGTG | TGGGGCCTTT | CTCTGCCACA | TAAATGCAGG | CTGGCTCCTC 1260 |
| TCTCCACACA | CTGGTCTCCA | GCTCACCAAT | CCTCCAGGTG | ACTTCCAGCC | ATGAAGACTC 1320 |
| TTGTCCTCCT | CTCTGCCCTT | GTCCTGCTGG | CATTCCAGAT | CCAGGCTGAT | CCCATTCAAG 1380 |
| AGGCAGAAGA | AGAGACTAAA | ACTGAGGAGC | AGCCAGCAGA | TGAGGACCAG | GATGTGTCTG 1440 |
| TCTCCTTTGA | AGGCCCAGAA | CCCTCTGCTC | TTCAAAATTT | AGGTGCGTGC | TTGTGCACAG 1500 |
| AATGATGGAG | GCTTGGAGTC | TCCTGATGGA | GGGTTGTAGA | TTAGCCCTGG | AGTCCTGTCA 1560 |
| AGGACAGTCT | GGTTCAGGTA | GCTGTCTATT | GATCCTTTCA | GAACTTCCCT | GTCTTATTCA 1620 |
| TAGAAATAAC | AGTGAGAGAC | AAGCCATTGG | GCTTGACTTT | TTCCTTTTAA | GATTTTGGTC 1680 |
| TAACAATTTA | TCTGTGAAAA | ACCTTTAAAA | TATAAAACAT | ATTGATTAGT | TCTTTTAAAC 1740 |
| CTGATTGATA | ATTTTGTTAT | AGGAAGAAAT | AACTGTTCTA | CTTTAAAAAT | TAGATTTGGT 1800 |
| ACCTAAATGC | CAGTGTATTA | AGGTGTTGGG | TCAGGAAAAC | ACAATAATGC | TGATAGAATG 1860 |
| TGGTGTAGAT | GACAATTCCT | ATATGCGATT | AACACTTGTT | AAATTGTCCT | ATCTCCATGT 1920 |
| GTTTGGGGTT | GATCATGGTG | CTGGCTGTGA | TGTCACCCAC | ACAGCAAACC | TACTTTCTAC 1980 |
| CATGCACAGG | ACATCTTCAT | AGGGTAGTTC | ACTGTCACAC | ACTGCTGGCC | TCCTTACTTC 2040 |
| ATGCCTGATG | CTTTCTCGTT | TCCTCAGAGA | TCAGATGGCC | ATGGAAGAGG | TGCCATTGCA 2100 |
| GAAGTTTCTG | CAGACCTTAT | GAAAATGCCA | CTTCGTTCTG | TGCTCAAGGT | CTATTTAAAC 2160 |
| AACACAAATT | CTGCTGCCTA | GAAACATGGC | CCCCAAGGAT | GAAATAACCA | CGTGCTCTGG 2220 |
| GACCTCACAA | TCTGTCATCA | TTGTGCTTGG | CCTCAACTTC | TTTTCCTTCT | CCAATAAACT 2280 |
| CCTTGCAGAC | AAATAACCTG | TTTATGTTTT | TTTGATGCTT | TCTATGTGGC | TTAGACAGGG 2340 |
| CTCTCCTGAG | CCATGTAGCA | GAATCTTCAG | TGAATCCTTT | GTAAAGAAG | TCTTGGTCAC 2400 |
| ATTTCAACAG | TCATATCAAG | GATGAGCAGG | AGGTTAGATC | CAAAGAGACA | AGATGCTCTG 2460 |
| CTCCAGCTGC | TTCTTGACTA | TCAAGTCTTC | TGTCCTTCAG | ATTAGAGTCA | CCCTCAAAAA 2520 |
| TTAGTCCCAC | CTTTTCATGT | TCTATTTTTT | T | | 2551 |

ANTIBIOTIC CRYPTDIN PEPTIDES AND METHODS OF THEIR USE

This application is a continuation of U.S. Ser. No. 08/342,268, filed Nov. 18, 1994, now pending, which is a continuation-in-part of U.S. Ser. No. 07/930,649, filed Aug. 14, 1992, now U.S. Pat. No. 5,422,424, issued Jun. 6, 1995, which is a continuation-in-part of U.S. Ser. No. 07/889,020, filed May 26, 1992, now abandoned, each of which is incorporated herein by reference.

This invention was made with government support under grant numbers AI22931, AI31696, DK08851, DK44632 and DK33506, awarded by National Institutes of Health. The Government has certain rights in the invention.

BACKGROUND OF THE INVENTION

1. Field of the Invention

This invention relates generally to antimicrobial peptides and more specifically to cryptdin peptides, nucleic acid molecules encoding cryptdins, and their uses.

2. Background Information

Survival in a world teaming with microorganisms depends on a network of host defense mechanisms. Among these mechanisms are phagocytosis by cells are resident in tissues or that circulate in the blood system and ingest, kill and digest potentially harmful microbes. Although pathogenic microbes may vary considerably, phagocytes are able to destroy the vast majority by sequestering them in intracytoplasmic vacuoles and exposing them to a lethal mixture of organic and inorganic toxins.

Perhaps the most remarkable ultrastructural feature of phagocytes are their several thousand cytoplasmic granules, which are membrane-bound organelles typically about 0.3 $\mu$m in diameter. During phagocytosis, some of these granules fuse to phagocytic vesicles thus enabling the contents of the granule to enter the lumen of the vesicle. Early observers surmised correctly that the granules contained factors which were responsible for intraphagosomal killing in digestion of microbes. These granules contain a mixture of antimicrobial molecules including various peptides such as the so-called defensins.

Defensins are abundant antimicrobial peptide components of vertebrate neutrophil and macrophage granules. Members of the defensin family have been identified previously in human, rabbit, guinea pig and rat phagocytes, primarily those phagocytes termed phagocytic granulocytes. Defensins are cationic peptides that have molecular weights between about 3 and 4 kiloDaltons (kDa) and that exhibit broad-range antimicrobial activities against gram negative and gram positive bacteria, many fungi and some enveloped viruses. The peptides are characterized by eight invariant amino acids, including six invariant cysteine residues that constitute a unique disulfide motif. The three disulfide bonds stabilize a tertiary conformation consisting predominantly of β-sheet. The highly ordered structure and the absence of a helix make defensins unique among known antimicrobial peptides. It appears that defensins exert their antibacterial effect by permeabilizing the cytoplasmic membrane of the target microorganism by a mechanism that may involve the formation of ion channels or transmembrane pores.

Until recently, defensins had been identified only in circulating or tissue phagocytes of myeloid origin. However, based on the presence of a particular mRNA, it has been surmised that similar peptides might be present in the epithelial cells of the small intestine. Such intestinal peptides may prevent access of microorganisms through the small intestine into the systemic circulation and, therefore, can be useful as a therapeutic or prophylactic agent. Thus, a need exists to identify peptides that have antimicrobial activity within the mucosal epithelium or in the intestinal lumen. The present invention satisfies this need and provides additional benefits as well.

SUMMARY OF THE INVENTION

The present invention provides a substantially purified cryptdin peptide having a consensus amino acid sequence:

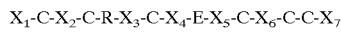
$X_1$-C-$X_2$-C-R-$X_3$-C-$X_4$-E-$X_5$-C-$X_6$-C-C-$X_7$ wherein $X_1$ is 3 to 9 amino acids; $X_2$ is 1 amino acid, preferably Y, H or R; $X_3$ is 2 or 3 amino acids; $X_4$ is 3 amino acids; $X_5$ is 5 amino acids; $X_6$ is 6 to 10 amino acids; and $X_7$ is 0 to 9 amino acids.

The invention also provides a substantially purified mouse cryptdin having a consensus amino acid sequence:

$X_1$-L-$X_2$-C-Y-C-R-$X_3$-C-K-$X_4$-E-$X_5$-G-T-C-$X_6$-C-C-$X_7$ wherein $X_1$ is 3 or 4 amino acids, preferably LRD, LSKK (SEQ ID NO: 1) or LRG;

$X_2$ is 1 amino acid, preferably V, L or I;

$X_3$ is 3 amino acids, preferably KGH or *RG, where * is S, T, K, I or A;

$X_4$ is 2 amino acids, preferably GR, RR or RG;

$X_5$ is 3 amino acids, preferably RMN, RVR, RVF HMN or HIN;

$X_6$ is 6 to 9 amino acids, preferably GIRFLY (SEQ NO: 2) or RNLFLTFVF (SEQ ID NO: 3), RRGHLMYTL (SEQ ID NO: 4) or RKGHL*YT* (SEQ ID NO: 5), where * independently is L or M; and $X_7$ is 0 to 3 amino acids, preferably R, S or PRR.

For example, the invention provides various mouse, rat or human cryptdins having the sequence:

1) LRDLVCYCRSRGCKGRERMNGTCRKGHL-LYTLCCR (SEQ ID NO: 6);
2) LRDLVCYCRTRGCKRRERMNGT-CRKGHLMYTLCCR (SEQ ID NO: 7);
3) LRDLVCYCRKRGCKRRERMNGT-CRKGHLMYTLCCR (SEQ ID NO: 8);
4) GLLCYCRKGHCKRGERVRGTCGIRFLYCCPR (SEQ ID NO: 9);
5) LSKKLICYCRIRGCKRRERVFGTCRN-LFLTFVFCC (SEQ ID NO: 10);
6) LKQCHCRKFCRPYEKAEGSCR-PGLFIKRKICCIQQWTPG (SEQ ID NO: 11);
7) GLLCYCRKGHCKRGERVRGTCGIRFLYCCPRR (SEQ ID NO: 12);
8) LSKKLICYCRIRGCKRRERVFGTCRN-LFLTFVFCCS (SEQ ID NO: 13);
9) LRDLVCYCRARGCKGRERMNGTCRKGHL-LYMLCCR (SEQ ID NO: 14);
10) LKQCHCRKFCRPYEKAEGSCR-PGLFIKRKICCIQQWTPGRT (SEQ ID NO: 15);
11) IGRPVRRCRCRANCGPKEYATAFCAQG-PFKQFKFCCT (SEQ ID NO: 16);
12) IRWPWKRCHCRSFCRPYENATSF-CAQGLFKQHKFCCLDTWPPRMK (SEQ ID NO: 17);
13) TSGSQARATCYCRTGRCATRESLSGV-CEISGRLYRLCCR (SEQ ID NO: 18); and

14) AFTCHCRRSCYSTEYSYGTCTVMGINHRFCCL (SEQ ID NO: 19).

Cryptdins are typically characterized by being naturally found in the epithelial cells of the small intestine, being cationic, being about 30 to about 45 amino acids in length, having at least three and, preferably, three to nine, amino acids to the N-terminal of the first cysteine residue, exhibiting specific antimicrobial activity against intestinal pathogens and opportunistic pathogens and being relatively nontoxic to cells of the host organism. However, there may be diversity in these structural and functional characteristics. The invention also provides cryptdin analogs, which are devoid of one or more amino acids N-terminal to the first cysteine. In addition, the invention also provides nucleic acid molecules encoding cryptdin peptides. For example, the invention provides genomic DNA sequences and CDNA sequences encoding mouse and rat cryptdins.

The invention further provides a method for detecting an inflammatory pathology in a subject by determining the amount of cryptdin in a biological sample from the subject and comparing that amount to the amount present in a normal subject. Such a method can be used to determine the presence of an inflammatory pathology such as inflammatory bowel disease, pancreatitis, malignancy, infection or ileitis.

The invention also provides a method for treating an inflammatory pathology in a subject by administering a cryptdin to the subject. Such treatment is particularly advantageous in patients who are immunocompromised due, for example, to malnutrition, radiation burns, immunosuppressive infections, autoimmune disease, neonatality, bone marrow transplantation or chemotherapy. A cryptdin can be administered orally, by nasogastric intubation, by transabdominal catheter, intravenously or by aerosol inhalation. When administered orally, it is preferably in a delayed release formulation designed to permit release in the small intestine. The cryptdin can be administered as a composition with a physiologically acceptable medium, and more than one cryptdin can be administered simultaneously or sequentially.

BRIEF DESCRIPTION OF THE DRAWINGS

FIG. 4(A) Lyophilized luminal lavage of small intestine from 12 mice and 20 µg protein was fractionated by P-60 gel filtration and electrophoresed on an acid-urea acrylamide gel (lane 2) along side a similarly prepared sample of bowel tissue (lane 1). The positions of cryptdins 1–5 (SEQ ID NOS: 6 to 10, respectively) are indicated.

FIG. 4(B) Partially purified luminal peptides (20 µg; as for FIG. 4.A., lane 2) were electrophoresed in a second acid-urea gel (lane 3) along with an identical sample previously treated with performic acid (lane 4). In lane 4, rapidly migrating, cyst(e)ine-containing peptides are absent due to the increased net negative charge resulting from the conversion of cyst(e)ines to cysteic acid residues.

FIGS. 6.A. and 6.B., 40X; FIGS. 6.C. and 6.D., 250X; FIGS. 6.E. and 6.F., 640X.

FIG. 8 shows the amino acid sequences for rat cryptdins 1–3 (SEQ ID NOS: 15–17, respectively), human cryptdins 5 and 6 (SEQ ID NOS: 18 and 19; HD-5 and HD-6) and a consensus sequence (Def consensus). Also shown are the amino acids sequences for rat prepro-cryptdins 1–3 (SEQ ID NOS: 20–22) as deduced from cDNA or genomic DNA sequences as indicated.

FIGS. 9(A–B) show the amino acid sequences of mouse cryptdins 1–17 (SEQ ID NOS: 23 to 39, respectively) as determined from the cDNA sequences encoding the specific cryptdin.

FIG. 9(A) shows the entire amino acid sequence of the mouse cryptdins. The amino acid sequences of cryptdins 1–6 (SEQ ID NOS: 23 to 28) were determined by sequencing the purified peptides. The amino acid sequences of cryptdins 7–17 (SEQ ID NOS: 29 to 39) were deduced from the cDNA sequences (see FIG. 10). The amino acids encoded by Exon 1, which encodes the signal peptide and propiece, and Exon 2, which encodes the mature cryptdin peptide, are indicated.

Figure 1:
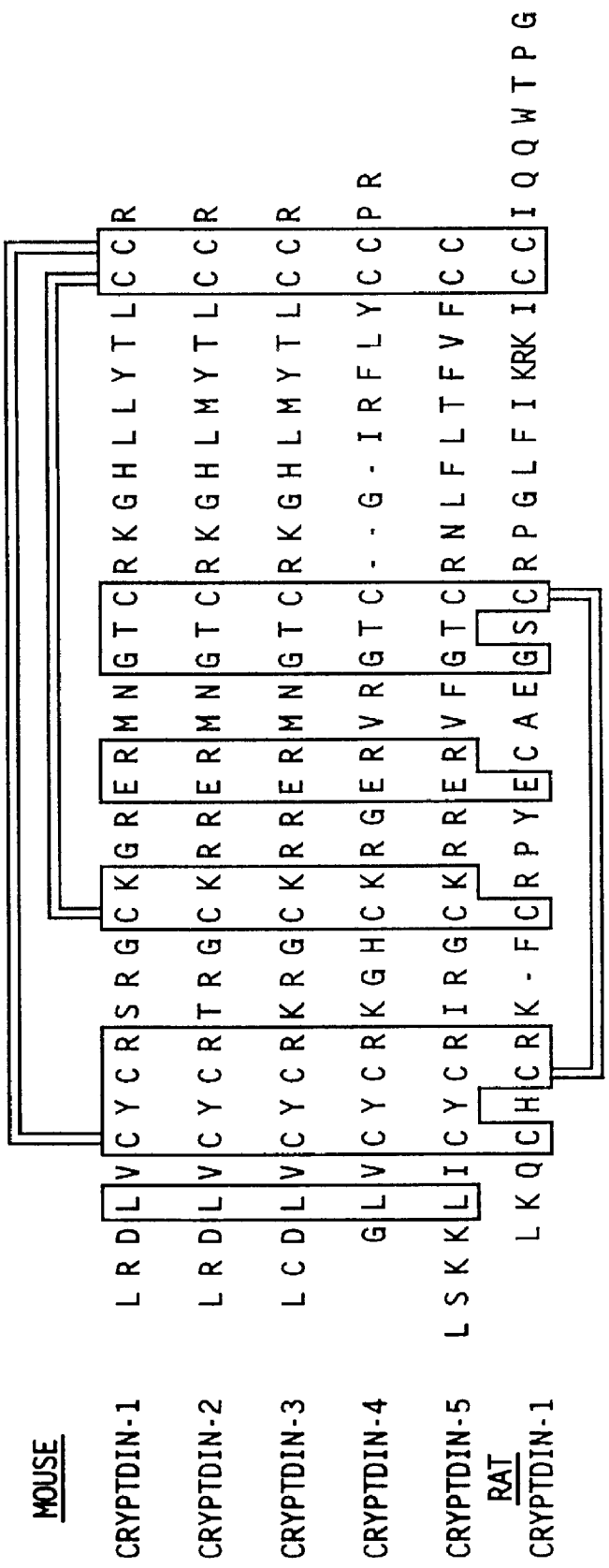
FIG. 1 provides the structures of mouse cryptdins 1–5 (SEQ ID NOS: 6 to 10, respectively) and rat cryptdin 1 (SEQ ID NO: 11). Amino acid residues are indicated by single letter code. Dashed lines are included in mouse cryptdin 4 (SEQ ID NO: 9) and rat cryptdin 1 (SEQ ID NO: 11) in order to preserve the consensus sequence where these peptides are shorter than other cryptdins. Invariant residues in the enteric cryptdin peptides are boxed. Disulfide bonding motifs are depicted by connecting double lines.

A dot indicates the sequence was not encoded by the cDNA clone. "*" indicates a space, which preserves the homology of the sequences.

FIG. 9(B) indicates the degree of relatedness of the mouse cryptdins. Amino acids that are identical to the amino acid shown for cryptdin 1 (SEQ ID NO: 23) are indicated by a dot.

Figure 10C:
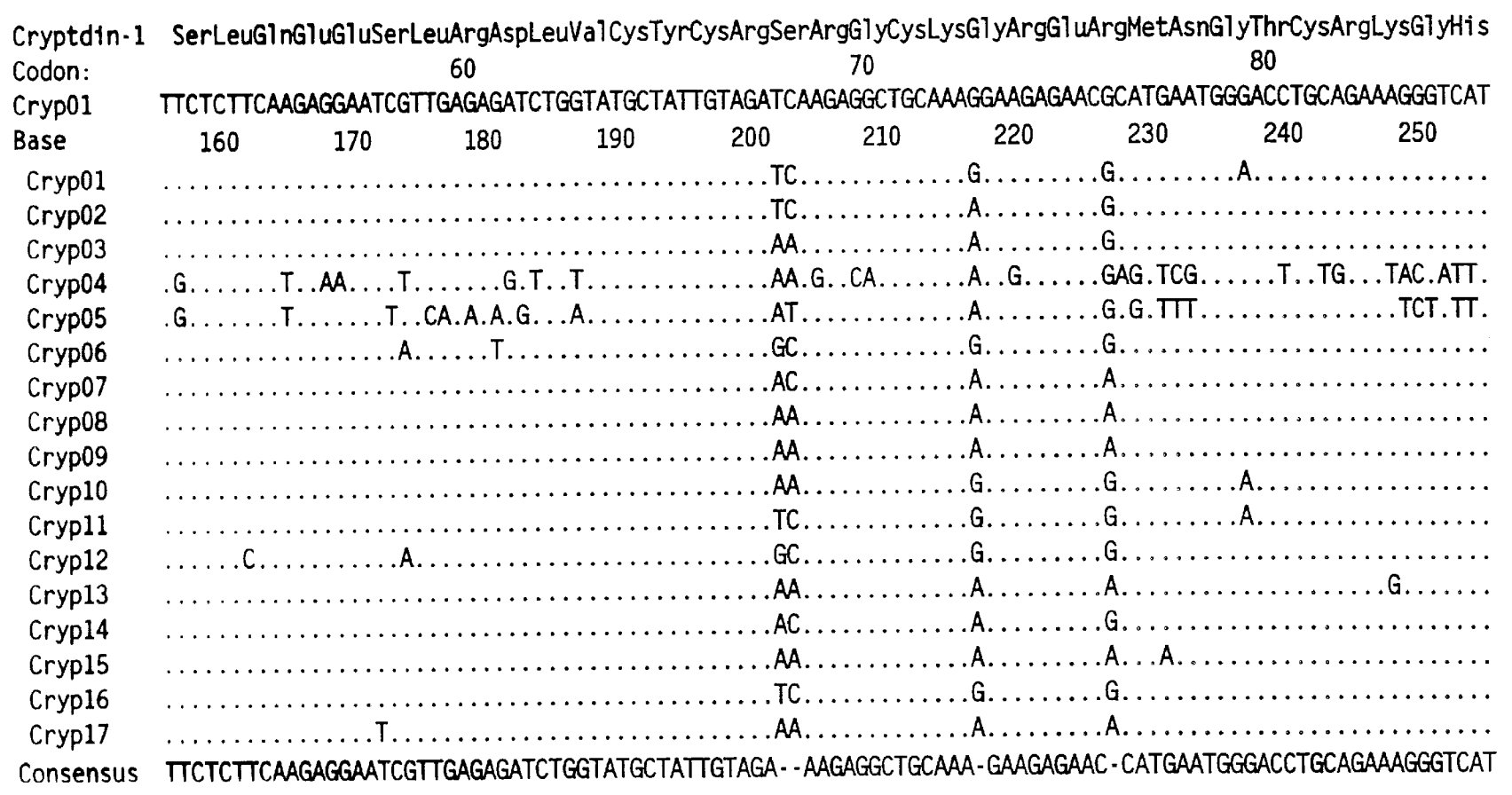

FIG. 10 shows the nucleic acid sequences for the cDNA sequences encoding mouse cryptdins 1–17 (SEQ ID NOS: 40 to 56, respectively). A consensus nucleotide sequence also is shown (SEQ ID NO: 57). A dot indicates the nucleotide is the same as shown for cryptdin 1. The amino acid sequence for cryptdin 1 (SEQ ID NO: 23) is shown above the nucleic acid sequence. Numbers below the nucleotide sequence indicate the nucleotide position relative to the methionine start codon (+1). Numbers above the amino acid sequence indicate the amino acid position. Italics indicate the mature cryptdin peptide sequence. Nucleotides in lower case letters indicate non-coding sequences. "***" indicates a stop codon. "(A)$_n$" indicates poly-A tail. "*" indicates a space and "–" indicates the particular nucleotide could not be determined unambiguously.

Figure 11A:
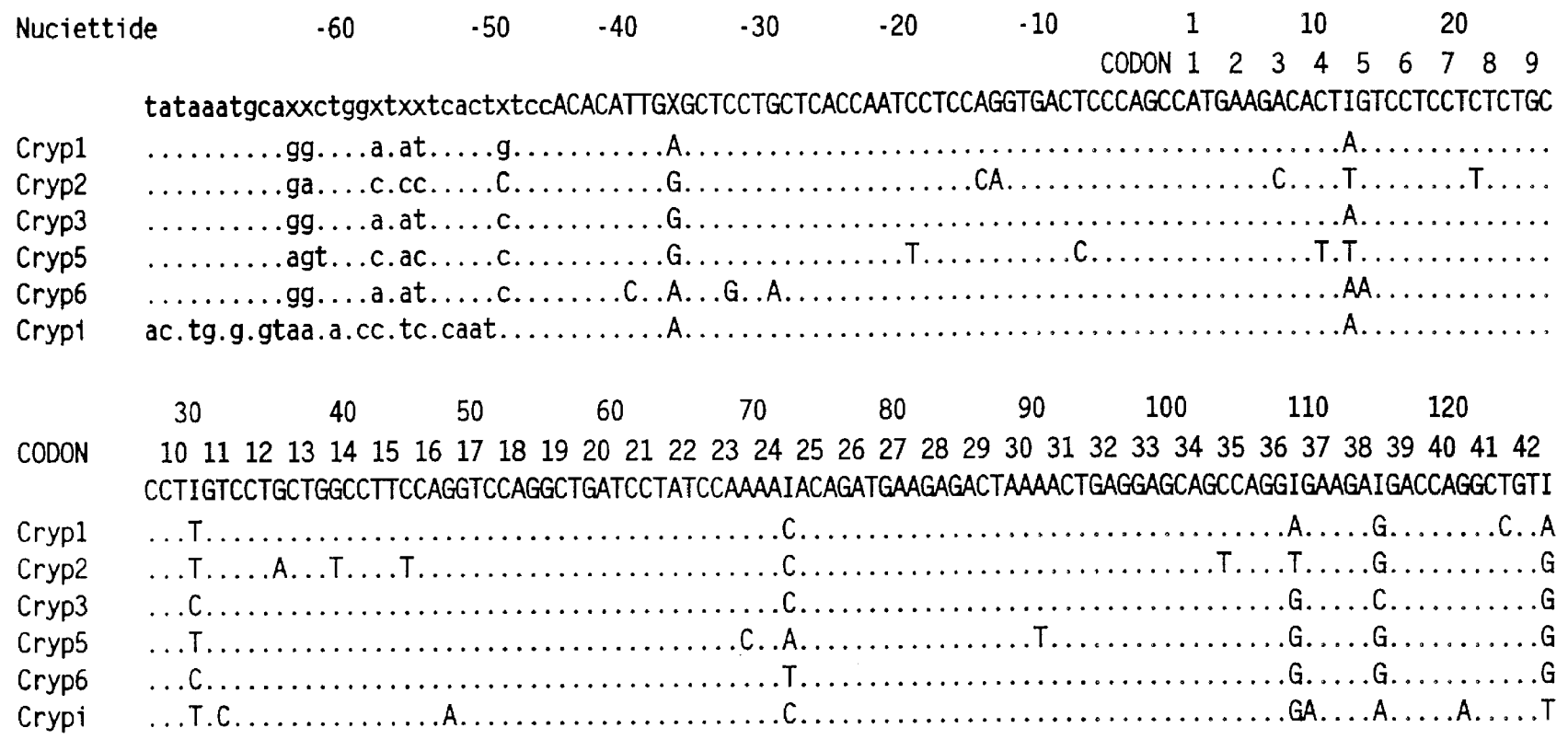
Figure 11B:
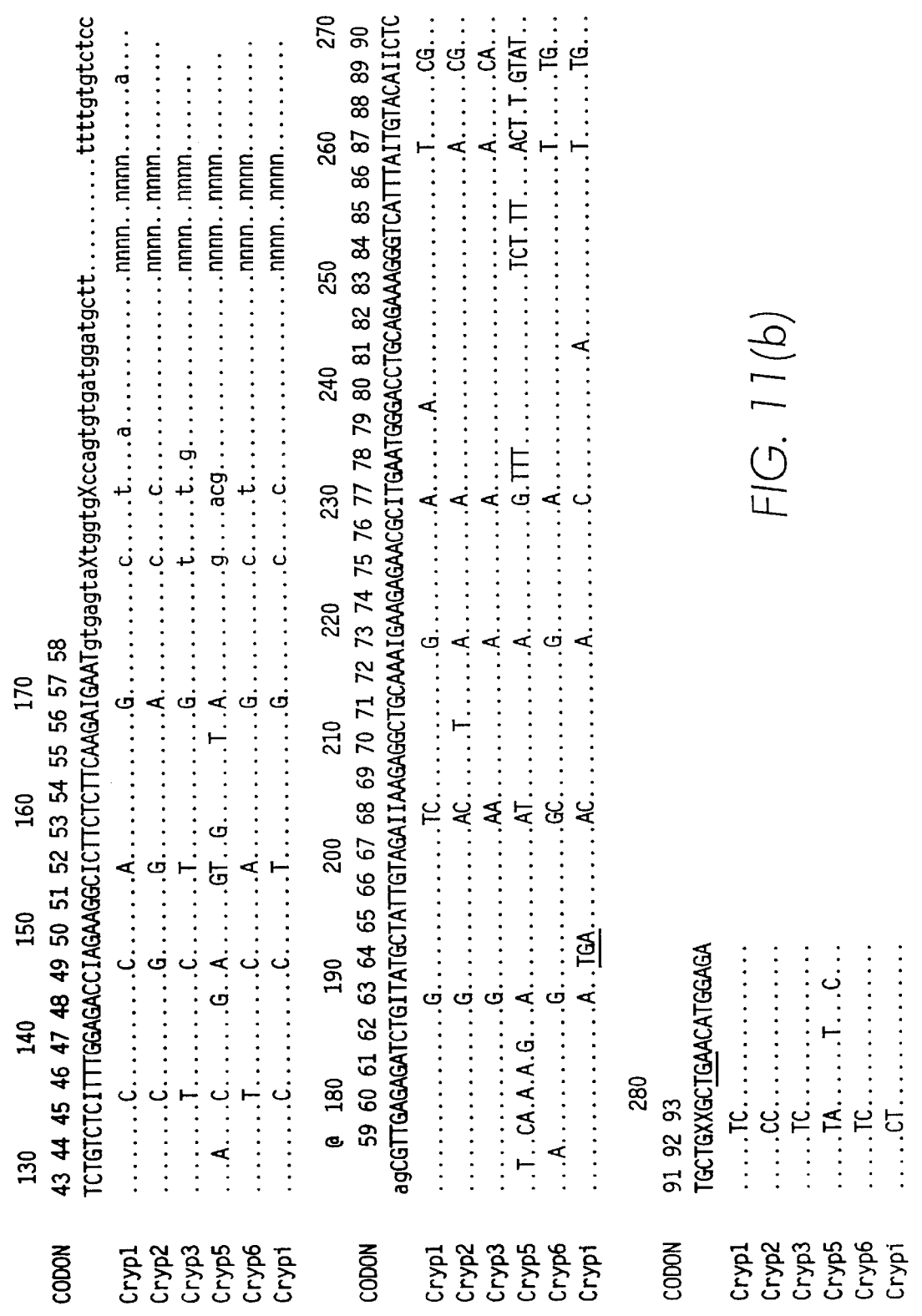

FIG. 11 shows the genomic DNA sequences for mouse cryptdins 1, 2, 3, 5 and 6 (SEQ ID NOS: 58 to 62, respectively) and the genomic sequence for the apparently inactivated mouse cryptdin i gene (Crypi; SEQ ID NO: 63), in which a stop codon (TGA) is substituted for a cysteine residue. Numbering is as described in the legend to FIG. 11. The upper sequence represents a consensus cryptdin gene sequence (SEQ ID NO: 64). "X" indicates positions at which at least two sequences containing nucleotide changes. The TATAAA box is shown in lowercase italics; exons are shown in capital letters; "**" indicates intron DNA; "n" represents approximately 500 base pairs that were not sequenced. "@" indicates the start of the cryptdin peptide coding region at codon 59. Coding sequences are indicated in bold print. Prepro-regions are coded by nucleotides 1–172; cryptdin peptides are coded by nucleotidase 173–279. The stop codon is underlined.

GenBank accession numbers for these sequences are 002994 (cryptdin 1, exon 1); 002995 (cryptdin 1, exon 2); 002996 (cryptdin 2, exon 1); 002997 (cryptdin 2, exon 2); 002998 (cryptdin 3, exon 1); 002999 (cryptdin 3, exon 2); 003000 (cryptdin 5, exon 1); 003001 (cryptdin 5, exon 2); 003002 (cryptdin 6, exon 1); 003003 (cryptdin 6, exon 2); 003004 (cryptdin i, exon 1); and 003005 (cryptdin i, exon 2).

Figure 12A:
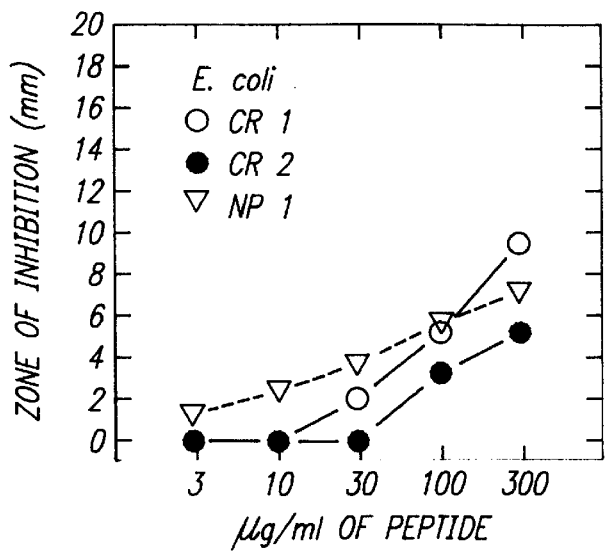
Figure 12B:
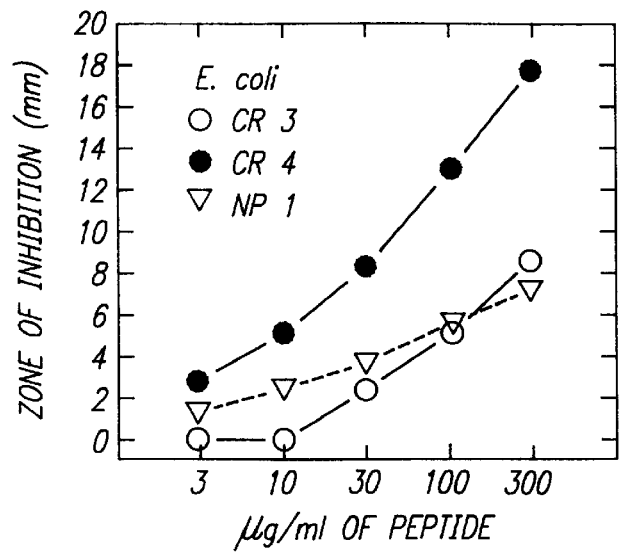
Figure 12C:
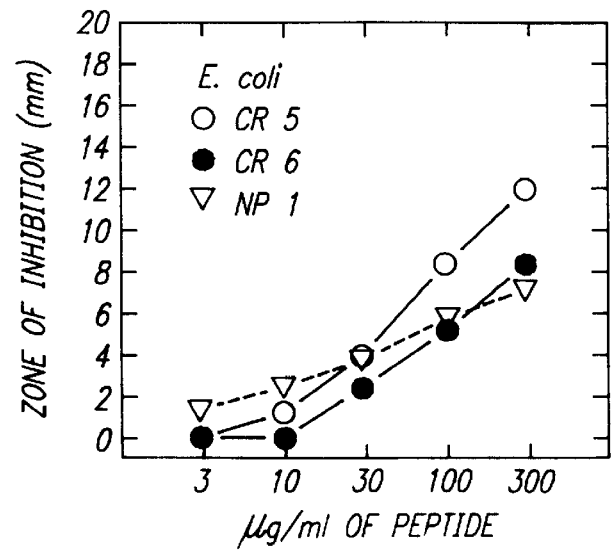

FIGS. 12.A. to 12.C. demonstrate the effectiveness of mouse cryptdins (as indicated) in inhibiting the growth of *E. coli* ML35 cells in an agar diffusion assay.

Figure 13A:
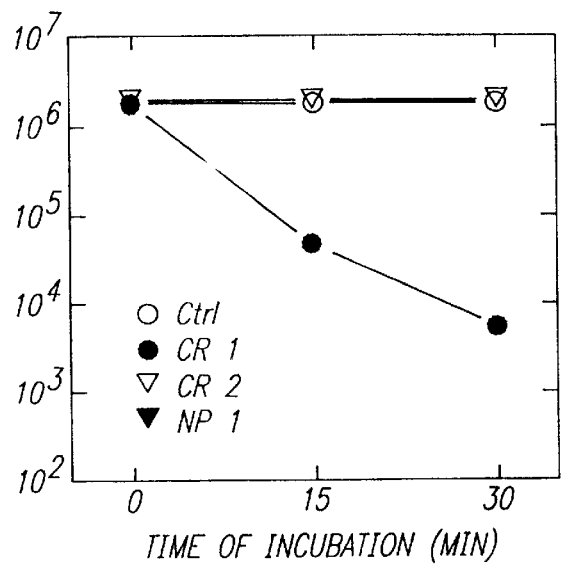
Figure 13B:
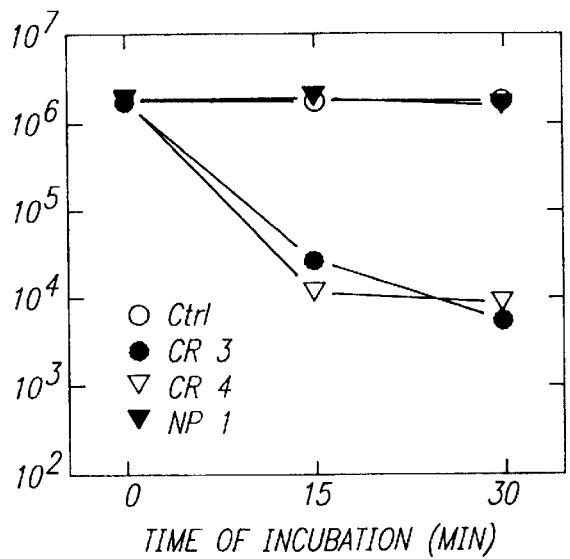
Figure 13C:
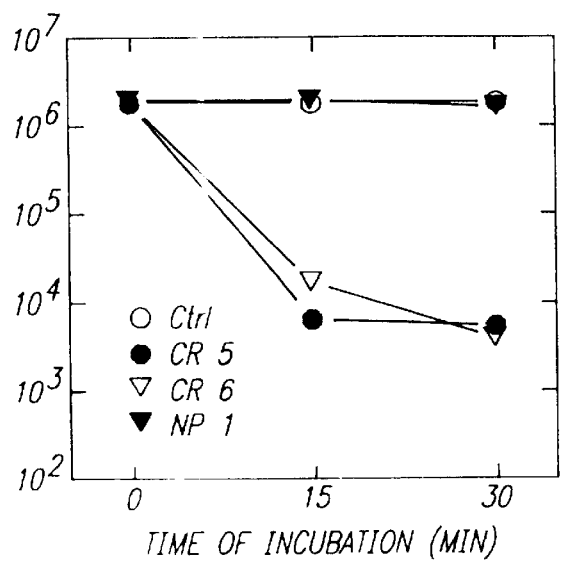

FIGS. 13.A. to 13.C. demonstrate the effectiveness of mouse cryptdins (as indicated) in killing *E. coli* cells in suspension.

FIGS. 14.A. to 14.C. show the cDNA sequences encoding rat cryptdin 1 (FIG. 14.A.), rat cryptdin 2 (FIG. 14.B.) and rat cryptdin 3 (FIG. 14.C.). Nucleotide numbers are indicated.

FIGS. 15.A. to 15.C. show the genomic DNA sequences encoding rat cryptdin 1 (FIG. 15.A.), rat cryptdin 2 (FIG. 15.B.) and rat cryptdin 3 (FIG. 15.C.). Nucleotide numbers are indicated.

DETAILED DESCRIPTION OF THE INVENTION

The invention provides small peptide molecules, termed cryptdins, which express a broad range of antimicrobial activity, particularly against intestinal pathogens, and for this reason are useful antimicrobial agents. For example, cryptdins have antimicrobial activity against gram negative and gram positive bacteria and against protozoan pathogens (see Example III). Cryptdin peptides and nucleic acid sequences encoding cryptdins were isolated from the small intestine and are active within the epithelial lining of the small intestine and within the lumen of the intestine. Because it is indicative of inflammatory processes, the presence of cryptdins can be utilized in the diagnosis of a wide range of inflammatory conditions.

As used herein, the term "cryptdin" or "enteric defensins" refers to peptides having generally between about 30 and 45 amino acids. Cryptdins are characterized, in part, by a consensus sequence containing six cysteine residues. Illustrative sequences are provided in FIG. 1, which shows invariant residues and the disulfide bonding motif. In addition, those residues which are preferably invariant are identified (see, also, FIGS. 8 and 9).

Cryptdins are further characterized by their cationic charge and their broad range of antimicrobial activity. While related to leukocyte-derived defensins, cryptdins are distinguished from these other molecules by the presence of 3 to 9 amino acids N-terminal to the first cysteine molecule. Cryptdins may have C-terminal extensions as well. In addition, they exhibit antimicrobial activity against enteric microorganisms, which can become blood-borne pathogens if the intestinal barrier is breached. Since cryptdins are associated with the secretory granules of Paneth cells in the small intestine, they can be secreted from the cells in which they are produced (Satoh, *Cell Tiss. Res.* 251:87–93 (1988); Satoh et al., *Acta Histochem.* 83:185–188 (1988)). Unlike leukocyte-derived defensins, cryptdins are not toxic to mammalian cells.

It should be appreciated that various modifications can be made to the cryptdin amino acid sequence without diminishing the antimicrobial activity of the peptide. It is intended that peptides exhibiting such modifications, including amino acid additions, deletions or substitutions are within the meaning of the term "cryptdin" and, therefore, within the scope of the invention. For example, cryptdin analogs, which are devoid of one or more amino acids N-terminal to the first cysteine residue, are within the present invention. Such cryptdin analogs can be synthesized using well known methods (see Example VI) or can be purified from the intestine where they may occur naturally due, for example, to partial proteolysis of a cryptdin peptide in the intestinal lumen.

Use of the phrase "substantially pure" in the present specification and claims as a modifier of peptide, protein or nucleic acid means that the peptide, protein or nucleic acid so designated has been separated from its in vivo cellular environment. As a result of the separation and purification, the substantially pure peptides, proteins and nucleic acids are useful in ways that the non-separated impure peptides, proteins and nucleic acids are not.

The cryptdin peptides of the present invention preferably contain between about 30 and 45 amino acids (see FIGS. 1, 8 and 9). Cryptdins can be synthesized by methods well known in the art, such as through the use of automatic peptide synthesizers or by well-known manual methods of peptide synthesis (see Example VI). In addition, they can be purified from natural sources such as small intestinal epithelium of vertebrate, preferably mammalian, origin (see Example I). Such epithelium can be obtained, for example, from rats, mice or humans using means well known to those skilled in the art.

As disclosed herein, various cryptdin peptides were isolated from intestinal epithelium, purified by chromatographic methods and characterized by electrophoresis and amino acid sequencing. Cryptdins were identified by their rapid migration on acid-urea PAGE and by their apparent molecular weight of about 4 kDa (see Examples I and II).

Anti-cryptdin antibodies were made using methods conventional in the art. For example, polyclonal antiserum can raised in appropriate animals, such as rabbits, mice or rats. Cryptdin peptides, either synthetic or obtained from natural sources, can be used to immunize the animal. As described in Example IV, a cryptdin analog, cryptdin C, which corresponds to residues 4–35 of mouse cryptdin 1 (SEQ ID NO: 6) as shown in FIG. 1, was used to immunize rabbits using well known methods. Serum samples were collected until the anti-cryptdin titer was appropriate. Various fractions of the antiserum, such as IgG, can be isolated by means well known in the art. Cryptdin immunogens also can be used to obtain monoclonal antibodies using methods well known in the art (see, for example, Harlow and Lane, *Antibodies: A Laboratory Manual* (Cold Spring Harbor Laboratory Press 1988), which is incorporated herein by reference).

The antimicrobial activity of a cryptdin can be measured against various pathogens. As disclosed in Example III, various microorganisms were grown to an appropriate concentration, mixed with an appropriate medium such as an agarose-trypticase soy medium and contacted with a cryptdin. Antimicrobial activity was apparent, for example, from the clear zones that surrounded the cryptdins in an agar diffusion assay. The area of the clear zones was concentration dependent (see FIG. 12).

Anti-cryptdin antibodies can be used to determine the presence of cryptdin in a biological sample such as a histological sample. For example, sections of small intestine are fixed by means well known to those skilled in the art and incubated with anti-cryptdin antibodies such as an IgG fraction of antiserum. If desired, the anti-cryptdin antibody can be detectably labelled or an appropriate detectable second antibody can be used to identify the presence of the primary antibody attached to the cryptdin. Means of detection include the use of radioactive protein A or enzyme substrates such as peroxidase (see Harlow and Lane, supra, 1988).

Alternative methods of determining the presence of cryptdin in a biological sample obtained, for example, by intestinal lavage or by disrupting cells or tissues can be useful to determine the presence of inflammatory processes. In the presence of inflammatory processes, the concentration of cryptdins is significantly altered from that found in the normal cell. In particular, a deviation from the normal level of cryptdins by one to two standard deviations is indicative of an inflammatory process. Such an inflammatory process can include, for example, inflammatory bowel disease, pancreatitis, malignancy, infection or ileitis.

Because of their broad range of antimicrobial activity and their ability to function within the intestinal epithelium or lumen, cryptdins are potent therapeutic agents for infections of the intestine. In particular, cryptdins are useful where the subject is immunocompromised due, for example, to malignancy, malnutrition, chemotherapy, radiation, immunosuppressive viruses, autoimmune disease or neonatality. In addition, cryptdins are useful in surgical prophylaxis, for example, by functioning to help sterilize the small bowel. Thus, cryptdins can be useful as medicaments for treating a subject having a pathology characterized, in part, by an inflammatory process.

A cryptdin, either purified from natural sources or synthetic, can be administered to a subject in need of such therapy by various means, including orally, preferably in a slow-release type formulation, which will avoid release within the stomach. Alternatively, cryptdins can be administered through nasogastric intubation, transabdominal catheter, intravenously or aerosol administration. Individual species of cryptdin can be administered alone or in combination. Cryptdins administered in combination can be administered simultaneously or sequentially and can be repeated as necessary.

Prior to the characterization of a mouse intestinal defensin cDNA, expression of defensins was thought to be limited to professional phagocytes, i.e., neutrophils and macrophages. The presence of high levels of cryptdin mRNA in Paneth cells led to the hypothesis that defensins synthesized in intestinal epithelium may contribute to antimicrobial barrier function in the small bowel (Ouellette et al., *J. Cell Biol.* 108:1687–1695 (1989a), which is incorporated herein by reference). Isolation and characterization of six mouse cryptdin peptides, two rat cryptdin peptides and 2 human cryptdin peptides, and the demonstration of antimicrobial activity of various cryptdin peptides indicates that the cryptdins have an antimicrobial role in the small intestine. The immunohistochemical localization of cryptdin(s) to Paneth cells is consistent with previous in situ hybridization analysis and suggests that defensins produced by these cells may contribute to restricting the colonization and invasion of the small bowel by bacteria.

Figure 2A:
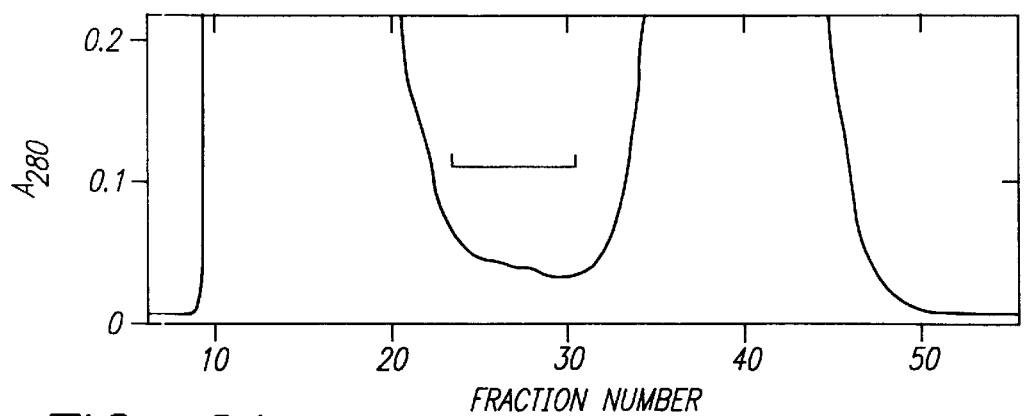
FIGS. 2.A. to 2.C. show chromatograms representing the purification of enteric cryptdins. Acid extract of jejunum and ileum was chromatographed in 30% acetic acid on a P-60 column. Fractions indicated by the bracket (FIG. 2.A.) were pooled and rechromatographed on the P-60 column (FIG. 2.B.). Cryptdin containing fractions (bracket, panel B) were pooled and further purified by reversed-phase high performance liquid chromatography (RP-HPLC) on 0.46×25 cm Vydac C-18 column. Water-acetonitrile gradient elution (--) using 0.13% (vol/vol) HFBA as modifier was used to purify cryptdins 1–5 (SEQ ID NOS: 6 to 10, respectively). The brackets in FIG. 2.C. indicate the peptide contained in each peak, and the portion of each which was subjected to a second round of RP-HPLC.
Figure 2B:
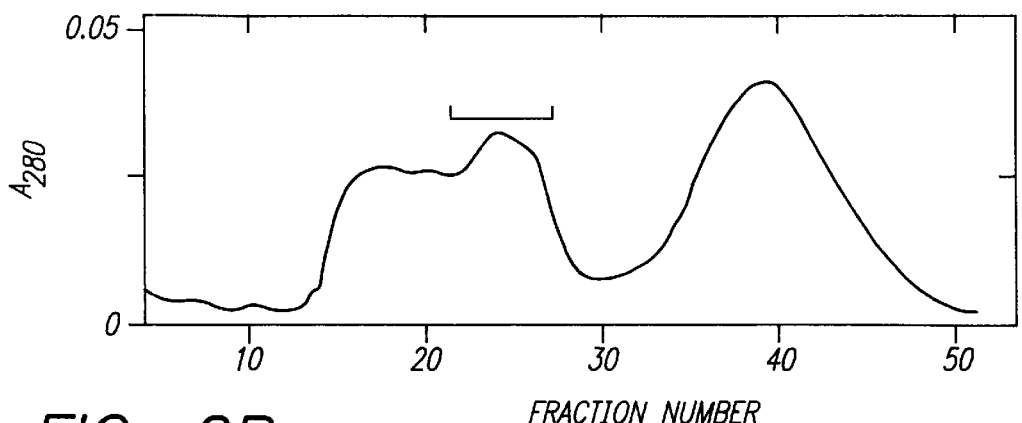
Figure 2C:
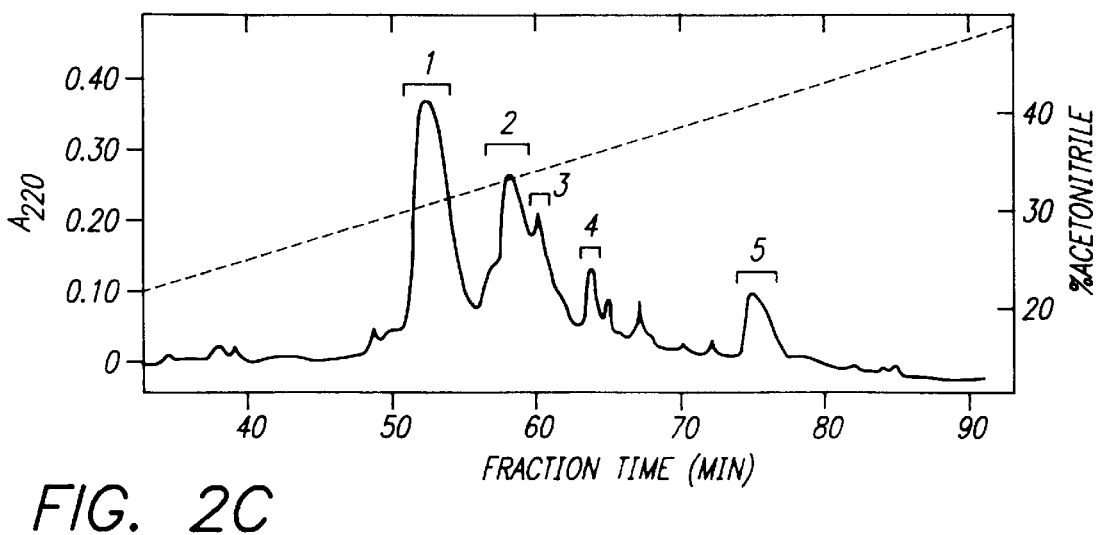
Figure 3:
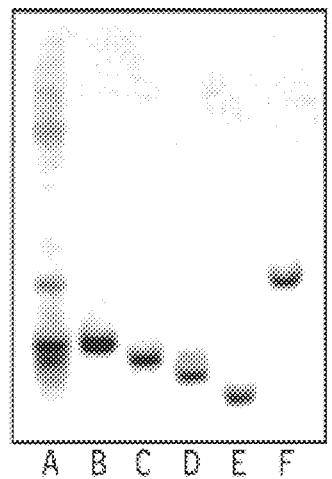
FIG. 3 shows acid-urea PAGE of purified enteric cryptdins. Samples of low molecular weight enteric peptides obtained by P-60 gel filtration (FIG. 2, panel B) and purified cryptdins were electrophoresed on a 12.5% acid-urea gel and stained with formalin-containing Coomassie Blue. Lane A: approximately 20 µg P-60 low molecular weight peptide fractions; lanes B–F: 1 µg each of cryptdins 1–5 (SEQ ID NOS: 6 to 10), respectively.

Initial efforts to purify intestinal defensins focused on the isolation of mouse cryptdin 1 (SEQ ID NO: 6), the peptide predicted from the cryptdin cDNA sequence. Since the deduced structure of the peptide is highly cationic, intestinal peptides were solubilized by homogenizing intact mouse jejunum and ileum in 30% formic acid. Acid-urea PAGE of the crude extract revealed several bands with $R_f$ values similar to those of rabbit defensin NP-1 and cryptdin C, a folded synthetic defensin congener corresponding to residues 4 to 35 in cryptdin 1 (SEQ ID NO: 6). Peptides corresponding to these bands were purified approximately 200-fold by sequential gel filtration chromatography on Bio-Gel P-60 (FIGS. 2.A. and 2.B.). Electrophoresis of P-60 column fractions on acid-urea gels showed that five fractions eluting between two prominent peaks (FIGS. 2.A. and 2.B., brackets) contained putative cryptdin peptides (FIG. 3, lane a). Peptides in these P-60 fractions migrated with an apparent molecular mass of approximately 4 kDa on SDS-PAGE (not shown), consistent 10 with the molecular weight of defensins. Furthermore, treatment of P-60 fraction samples with performic acid reduced the electrophoretic mobility of the five putative mouse cryptdins in acid-urea gels, behavior that is characteristic of defensins and polypeptides that contain multiple cysteine residues.

Defensins in pooled P-60 fractions were purified further using sequential rounds of RP-HPLC utilizing different ion-pair agents. Initial HPLC fractionation utilized water-acetonitrile gradients containing 0.13% heptafluorobutyric acid (HFBA) as the ion-pairing agent, whereby each of the five peptides contained in the pooled P-60 fractions was resolved to near purity in a single run (FIG. 2.C.). Complete purification of five peptides, mouse cryptdins 1–5 (SEQ ID NOS: 6 to 10, respectively), was achieved by subsequent RP-HPLC using 0.1% trifluoroacetic acid (TFA) (FIG. 3, lanes B–F). Assuming extraction of individual peptides is equally efficient, both acid-urea gel electrophoresis and RP-HPLC of the P-60 fractions containing putative cryptdins showed that the relative abundance of the peptides is cryptdin 1>cryptdin 2>cryptdin 5>cryptdin 3>cryptdin 4. The relative amounts of cryptdins 1–5 (SEQ ID NO: 6 to 10, respectively) have been qualitatively reproducible in every preparation of acid-extracted protein from mouse small intestine.

Using a modification of the method described above, mouse cryptdin 6, rat cryptdins 2, human cryptdins 5 and 6 also were isolated (see Examples I and II; see, also, FIGS. 8 and 9). In addition, longer forms of mouse cryptdins 4 and 5 (compare SEQ ID NOS: 9 and 12; 10 and 13) and rat cryptdin 1 (compare SEQ ID NOS: 11 and 15) were obtained. This result suggests that the initial method of purifying cryptdin peptides resulted in partial degradation of the C-termini of some peptides. Significantly, both forms of the purified cryptdin peptides have antimicrobial activity.

Biochemical characterization of the isolated cryptdins demonstrated that these peptides are defensins. Amino acid analysis of each peptide showed their compositions (cationic peptides of about 30 to 45 amino acid residues, including 6 half-cysteines) are compatible with defensin-like molecules. The complete sequences of mouse cryptdins 1–6 (SEQ ID NOS: 23 to 28), rat cryptdins 1 and 2 (SEQ ID NOS: 11, 15 and 16) and human cryptdins 5 and 6 (SEQ ID NOS: 18 and 19) were determined by automated Edman degradation and, in some cases, by amino acid analysis of carboxyl terminal chymotryptic peptides (see FIGS. 1, 8 and 9). The primary structures of the cryptdins contain the distinctive structural features of human, rabbit, rat and guinea pig neutrophil defensins (Lehrer et al., *Cell* 64:229–230 (1991a), which is incorporated herein by reference), i.e., the six invariant cysteine residues and the glycine and glutamic acid in positions that are highly conserved in myeloid defensins.

The cryptdin peptides disclosed herein contain features that are unique and distinct from defensins of myeloid origin. For example, mouse cryptdins 1, 2, 3 and 6 (SEQ ID NOS: 23 to 25 and 28, respectively) are almost identical, differing only at two or three positions (see FIG. 9.A.). Analysis of codons from which these amino acid differences could arise shows that the conversion, for example, of $Ser^{10}$ to $Lys^{10}$ in cryptdin 1 (SEQ ID NO: 23) and cryptdin 3 (SEQ ID NO: 25), respectively, requires two nucleotide substitutions. On the other hand, single nucleotide changes in the codon encoding $Thr^{10}$ in cryptdin 2 (SEQ ID NO: 24) could give rise to cryptdins 1, 3 and 6, suggesting that the cryptdin 2 gene may be an intermediate or progenitor of the cryptdin 1, 3 and 6 genes. Similarly, a single nucleotide change in the codon for $Thr^{10}$ of cryptdin 2 can account for the deduced amino acid at position 10 in cryptdins 7–17 (see FIG. 10, nucleotides 203–205; SEQ ID NOS: 46 to 56).

By homology with the structures of known myeloid defensins, the cryptdin 1 N-terminus was predicted to begin at $Leu^4$ or $Val^5$, which is 1–2 residues prior to the first conserved cysteine. However, compared to myeloid defensins, cryptdins have variably extended N-termini that contain from three (mouse cryptdin 4, SEQ ID NO: 26; rat cryptdin 1, SEQ ID NO: 11) to nine (human cryptdin 5, SEQ ID NO: 18) amino acids preceding the first cysteine. In mouse cryptdins 1–3 and 6–17 (SEQ ID NOS: 23 to 25 and 28 to 39, respectively), the N-peptidyl extensions consist of two charged internal residues flanked by amino acids with hydrophobic sidechains. Since natural variation in defensin amino termini correlates with relative antimicrobial potency in vitro (Ganz et al., *J. Clin. Invest.* 76:1427–1435 (1985), which is incorporated herein by reference), the extended N-termini of enteric defensins may have evolved for a unique role in the bowel.

Mouse cryptdin 4 (SEQ ID NO: 9), the most cathodal and, apparently, least abundant mouse enteric defensin, was the first defensin found to contain a chain length variation between the fourth and fifth cysteine residues. Unlike the majority of previously known defensins, in which nine amino acids separate the fourth and fifth cysteines (Lehrer et al., supra, 1991a), mouse cryptdin 4 (SEQ ID NO: 9) contains only six residues between the same two amino acids (FIG. 1). In addition, rat cryptdins 1–3 (SEQ ID NOS: 11 and 15–17) contain ten amino acid residues between the fourth and fifth cysteines. These findings indicate the defensin fold involving this stretch of the peptide chain can accommodate significant variability in the size of the loop, as compared to the invariant loop size defined by crystal and NMR structures, respectively, of human and rabbit neutrophil defensins. Also, rat cryptdins 1–3 (SEQ ID NOS: 11 and 15–17) are the only cryptdins containing three, instead of four, amino acid residues between the second and third cysteine residues.

Since cryptdin mRNA levels increase during postnatal development of mouse small bowel (Ouellette et al., supra, 1989a), it was investigated whether accumulation of enteric defensins was regulated similarly. Analysis of intestinal acid extracts from male and female mice showed that mouse cryptdins 1–3 and 5 (SEQ ID NOS: 6 to 8 and 10, respectively) are present in adult mice, regardless of gender. On the other hand, extracts from 9 day-old mice lack the peptides, consistent with postnatal accumulation of cryptdin MRNA.

Figure 5:
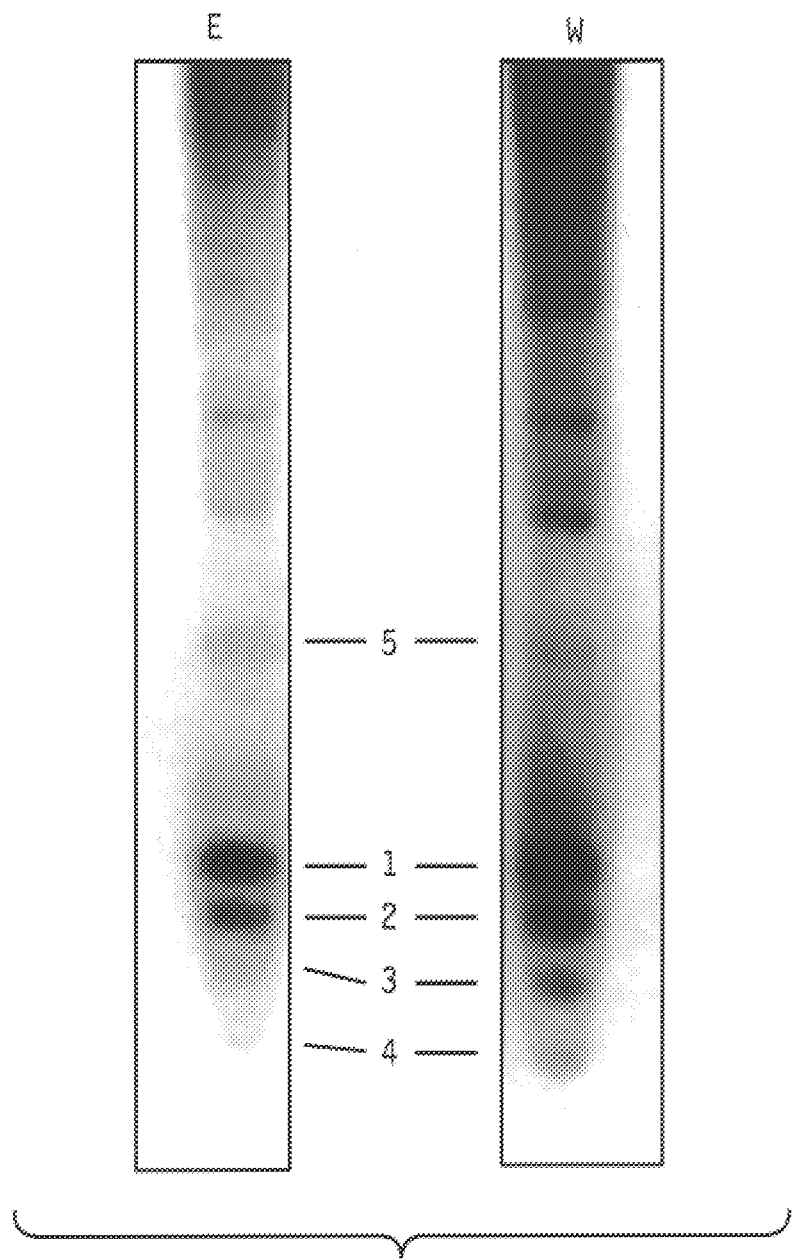
FIG. 5 shows the identification of mouse cryptdins 1–5 (SEQ ID NOS: 6 to 10, respectively) in small intestine epithelium. Acid extracts of intact, whole small intestine (W) or epithelial sheets (E) were lyophilized, dissolved in sample solution and resolved on a 12.5% acid-urea acrylamide gel. Cryptdins 1–5 (SEQ ID NOS: 6 to 10) are identified numerically.
Figure 6A:
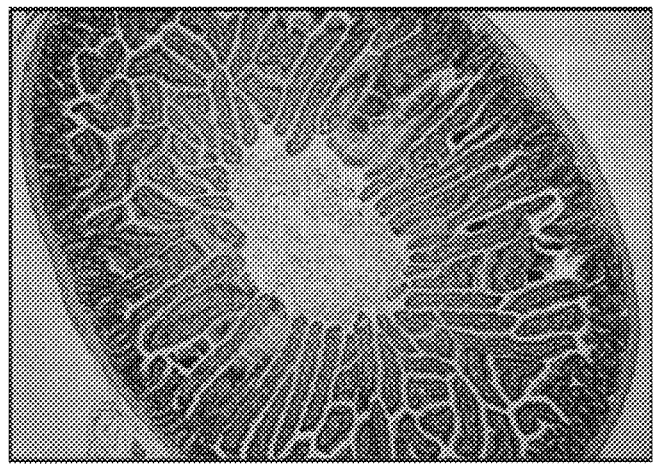
FIGS. 6.A. to 6.F. show the immunohistochemical localization of cryptdin 1 (SEQ ID NO: 6) in small intestine. Full thickness sections of adult mouse jejunem were incubated with preimmune (FIGS. 6.A., 6.C. and 6.E.) or anti-cryptdin C rabbit IgG (FIGS. 6.B., 6.D. and 6.F.) and developed using peroxidase anti-peroxidase secondary antibody magnifications.
Figure 6B:
Figure 6C:
Figure 6D:
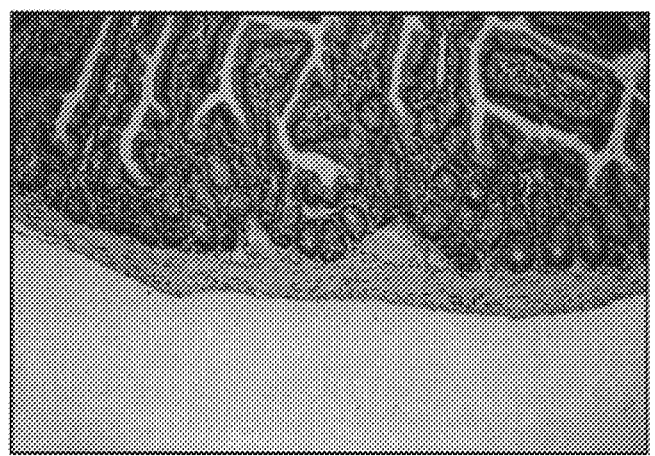
Figure 6E:
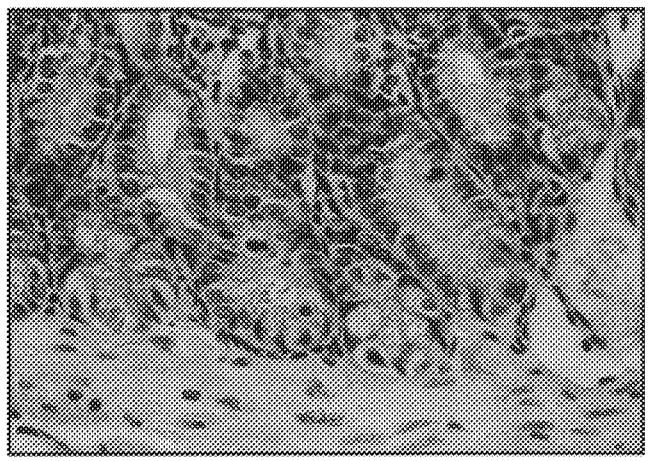
Figure 6F:
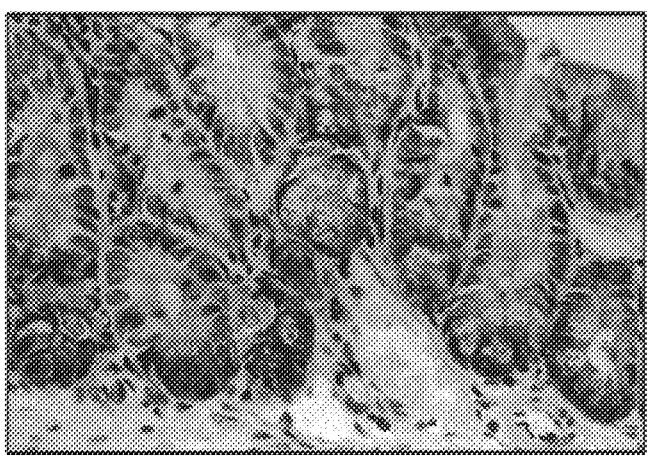

Mouse cryptdins 1–5 (SEQ ID NOS: 6 to 10) were purified from intestinal epithelial cells. In the presence of EDTA, the intestinal epithelium no longer adheres to the underlying basement membrane and floats free of the lamina propria upon gentle agitation (Bjerknes and Cheng, *Am. J. Anat.* 160:51–63 (1981), which is incorporated herein by reference). Preparations of epithelial sheets isolated in this manner were concentrated by low speed centrifugation 35 and extracted with 30% formic acid. Peptides extracted from isolated epithelial sheets comigrate with cryptdins 1–5 (SEQ ID NOS: 6 to 10) when analyzed by acid-urea PAGE (FIG. 5), demonstrating their epithelial origin.

Immunoperoxidase staining of full-thickness sections of small intestine with an anti-cryptdin antibody demonstrate cryptdin antigen in Paneth cells, consistent with localization of cryptdin mRNA by in situ hybridization (Ouellette et al., supra, (1989a)). Incubation of sections of adult mouse jejunum and ileum with a polyclonal anti-cryptdin IgG produced by rabbits immunized with the synthetic congener cryptdin C localized the immunoperoxidase reaction to granulated cells, morphologically defined as Paneth cells, at the base of every crypt (FIG. 6). The staining pattern accentuates the granular appearance of the cytoplasm in these cells and the immunoreactivity appears particularly strong over Paneth cell granules. The antibody is specific for mouse cryptdin(s), since it is negative both for rat and human Paneth cells (data not shown). Leukocytes in the lamina propria of the villi also were negative, suggesting that related enteric defensins are not expressed by phagocytes or lymphocytes. Because of the extensive similarity of mouse cryptdins 1–3 (FIG. 1; SEQ ID NOS: 6 to 8), the polyclonal antibody produced against cryptdin C probably recognizes the three peptides. Conversely, because mouse cryptdin 4 (SEQ ID NO: 9) and cryptdin 5 (SEQ ID NO: 10) differ markedly from the other mouse cryptdins, the anti-cryptdin C antibody is unlikely to react with cryptdin 4 (SEQ ID NO: 9) and cryptdin 5 (SEQ ID NO: 10), leaving their origin in Paneth cells somewhat unresolved.

Figure 4:
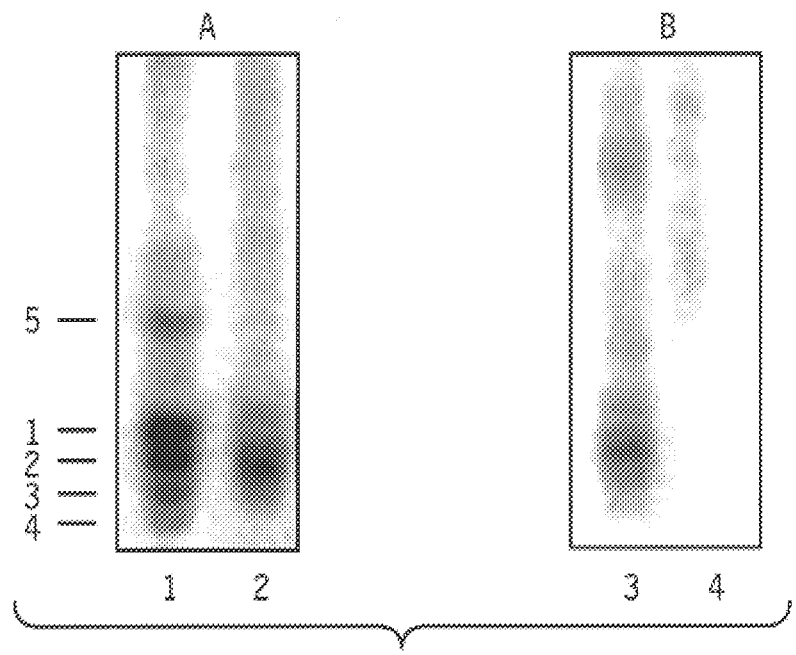
FIGS. 4(A–B) compares mouse cryptdins 1–5 (SEQ ID NOS: 6 to 10, respectively) and partially purified luminal peptides.

Immunohistochemical data suggest cryptdins are secreted into the intestinal lumen. Material in the small intestinal lumen is strongly positive for the antibody but negative for pre-immune sera or IgG (FIGS. 6.A. and 6.B.). Although the agonist for Paneth cell defensin secretion is unknown, lysozyme, another protein constituent of Paneth cell granules, is secreted into the lumen under cholinergic regulation. Consistent with immunochemical detection of anti-cryptdin C positive material in the intestinal lumen, acid-urea PAGE of saline washes of adult jejunum and ileum contain peptides with mobilities very similar to but distinct from the mobility of cryptdins (FIG. 4). Nevertheless, the peptides are not identical to cryptdins 1–5 (SEQ ID NOS: 6 to 10, respectively) by either migration in acid-urea PAGE or by HPLC analysis, suggesting they may correspond to cryptdins that have been processed further. Conceivably, luminal cryptdin or cryptdin-like material could derive from exfoliated Paneth cells in the lumen, but the low rate of Paneth cell turnover suggests this is unlikely. The release of cryptdins or processed variants into the small bowel by Paneth cells contrasts with the apparent lack of defensin secretion by leukocytes, and it is inferred that a secretory pathway may exist for the constitutive delivery of defensins into the intestinal lumen by Paneth cells.

The antibacterial activity of purified mouse cryptdins 1–5 (SEQ ID NOS: 6–10) was tested against wild type and phoP mutant *S. typhimurium* using a modified plate diffusion assay (Lehrer et al., *J. Immunol. Methods* 137:167–173 (1991b), which is incorporated herein by reference). phoP is a two-component regulatory locus that is essential to *S. typhimurium* virulence and survival within macrophages (Fields et al., *Science* 243:1059–1062 (1989); Miller et al., *Proc. Natl. Acad. Sci., USA* 86:5054–5058 (1989), each of which is incorporated herein by reference). Mutants in the phoP locus are particularly sensitive to rabbit defensins NP-1 and NP-2 when compared to wild type parent strains (Fields et al., supra, 1989; Miller et al., *Infect. Immun.* 58:3706–3710, (1990), which is incorporated herein by reference).

Figure 7A:
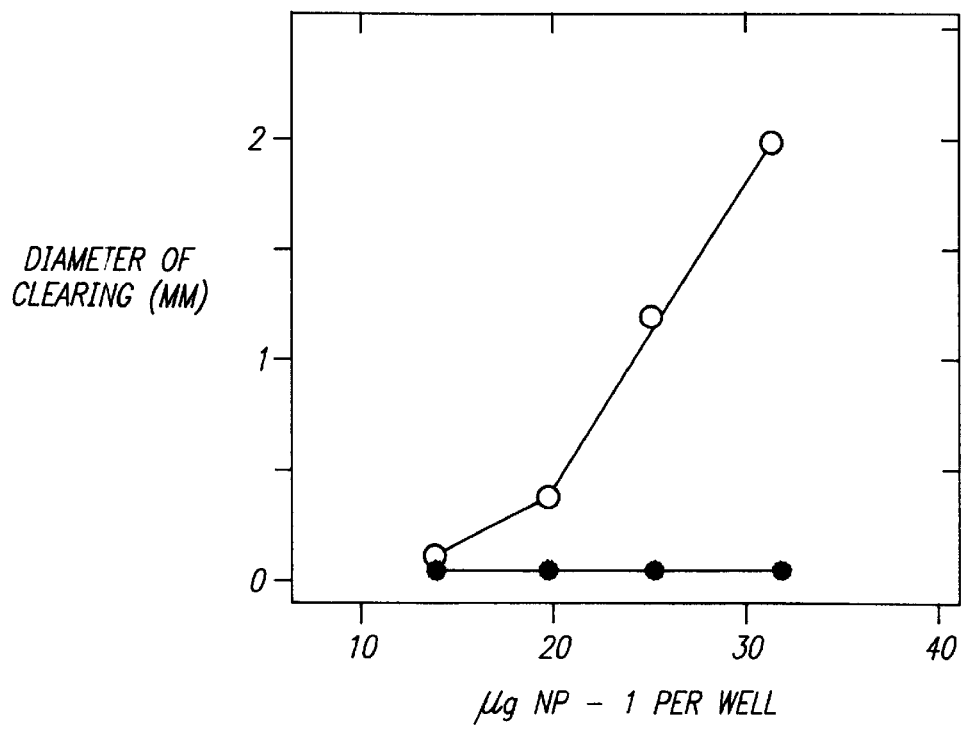
FIGS. 7.A. and 7.B. depict the antimicrobial activity of mouse cryptdin 1 (SEQ ID NO: 6). Samples of purified natural mouse cryptdin 1 (FIG. 7.A.) or rabbit NP-1 (FIG. 7.B.) were dissolved in 0.01% acetic acid and pipetted into wells produced in a 0.6% agarose/0.3% tryptone plate containing 1×10$^6$ log phase bacterial cells. After incubation at 37° C. for 18 hr, antimicrobial activity was evaluated by measuring the diameters of the clear zones. Closed circles denote wild type *S. typhimurium*; open circles denote the phoP⁻ mutant.
Figure 7B:
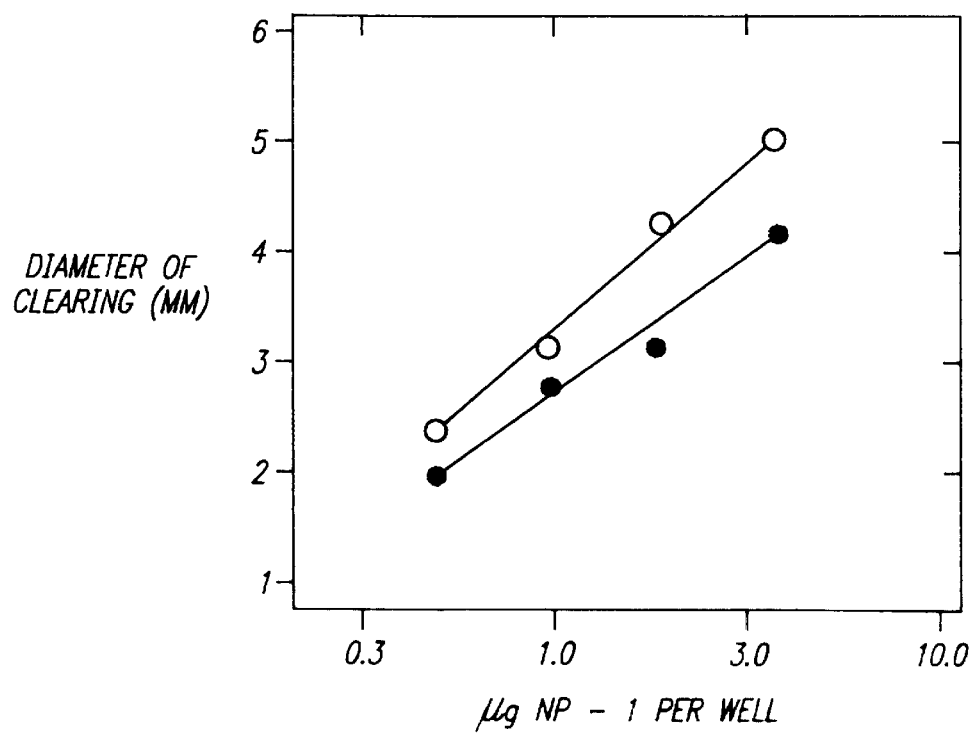

Under assay conditions using a phosphate buffer as described in Example III, the antimicrobial activity of rabbit defensin NP-1 against wild type and the phoP mutant organisms was quite similar (FIG. 7.B.). On the other hand, at concentrations of mouse cryptdin 1 (SEQ ID NO: 6) that are effective against the attenuated mutant, wild type *S. typhimurium* is completely resistant to the effects of the peptide (FIG. 7.A.).

The differential activity of cryptdin 1 (SEQ ID NO: 6) against avirulent *S. typhimurium* suggests that resistance to mucosal defensins may be important for the evolution of virulence in enteric pathogens. However, in experiments using HEPES or PIPES as buffers as described in Example III, concentrations of 100 μg/ml or 300 μg/ml cryptdin 1 were as effective as NP-1 in inhibiting the growth of wild type *S. typhimurium*. Furthermore, at these concentrations, cryptdins 4 and 5 were more effective than NP-1 in preventing the growth of mutant and wild type *S. typhimurium* (not shown).

The present invention also provides substantially purified nucleic acid sequences encoding cryptdins. For example, the cDNA sequences for mouse cryptdins 1–17 (SEQ ID NOS: 40–56) are shown in FIG. 10 and the cDNA sequences for rat cryptdins 1–3 (SEQ ID NOS: 65–67) are shown in FIGS. 14.A. to 14.C. In addition, the genomic DNA sequences for mouse cryptdins 1, 2, 3, 5 and 6 (SEQ ID NOS: 58–62) and for an apparently inactivated cryptdin gene, cryptdin i (SEQ ID NO: 63) are shown in FIG. 11 and the genomic DNA sequences for rat cryptdins 1–3 (SEQ ID NOS: 68–70) are shown in FIGS. 15.A. to 15.C.

The skilled artisan would recognize that various 35 nucleotide substitutions could be made in the nucleic acid sequences shown in FIGS. 10, 11 14 and 15 without altering the amino acid sequence of the encoded cryptdin peptide due to degeneracy of the genetic code. Such nucleotide sequences, which are equivalent to the sequences shown in FIGS. 10, 11, 14 and 15 are encompassed within the claimed invention.

The invention also provides nucleotide sequences that consist of a portion of a nucleic acid sequence as shown in FIGS. 10, 11, 14 and 15. Such a nucleotide sequence can be useful, for example, as a probe, which can hybridize under relatively stringent conditions to a nucleic acid molecule encoding a cryptdin peptide. For hybridization, such a nucleotide sequence should be at least about 10 nucleotides in length. One skilled in the art would know that appropriate conditions for hybridization can be determined empirically or can be calculated based, for example, on the G:C content of the nucleotide sequence, the length of the sequence and the number of mismatches, if any, between the probe and the target sequence (see, for example, Sambrook et al., *Molecular Cloning: A laboratory manual* (Cold Spring Harbor Laboratory Press 1989), which is incorporated herein by reference).

A nucleotide sequence as described above can be detectably labelled by attaching, for example, a radioactive label or biotin, or can be unlabelled. A labelled or unlabelled sequence also can be used as a primer for the polymerase chain reaction (PCR; see, for example, Erlich, *PCR Technology: Principles and applications for DNA amplification* (Stockton Press 1989), which is incorporated herein by reference). Such a sequence can be useful, for example, to identify a nucleic acid sequence encoding a cryptdin in a cell.

A nucleic acid molecule as shown in FIGS. 10, 11, 14 and 15 or a nucleotide sequence derived therefrom also can be useful, for example, for preparing a cryptdin peptide or a portion of a cryptdin peptide using well known methods of recombinant DNA technology. For example, the nucleic acid sequence can be cloned into an expression vector such as a baculovirus vector or a viral vector, which can infect a mammalian cell and express an encoded cryptdin peptide in the cell. Expression from such a vector can be useful for producing large amounts of a cryptdin, which can be used to treat a subject having an inflammatory pathology as described herein, or for producing a cryptdin directly in a subject. Thus, the invention provides vectors containing a nucleic acid molecule as shown in FIGS. 10, 11, 14 and 15 as well as specific host cells, in which the vector can propagate or can express a cryptdin.

The following examples are intended to illustrate but not limit the invention.

EXAMPLE I

Purification of Enteric Defensins

Outbred Swiss mice, (Crl:CD-1)(ICR)BR, 45 day old males (30–35 g) or timed-pregnant dams, were obtained from Charles River Breeding Laboratories, Inc. (North Wilmington Mass.). In studies of newborn mice, litters were culled to 8 pups within 12 hr of delivery. Mice were housed under 12 hr cycles of light and darkness and had free access to food and water.

Cryptdins were isolated by a modification of the method described by Selsted et al., *J. Cell. Biol.* 118:929–936 (1992); Ouellette et al., *Infect. Immun.* 62:5040–5057

(1994), each of which is incorporated herein by reference. Jejunal and ileal intestinal segments were excised from 60 mice immediately after carbon dioxide euthanasia. The tissue was washed and the lumen was flushed with ice cold water prior to homogenization in 500 ml ice cold 30% acetic acid. The homogenate was clarified by centrifugation, lyophilized, dissolved in 200 ml 30% acetic acid, clarified by filtration through Whatman 541 filter paper and applied to a 10×60 cm Bio-Gel P-60 column equilibrated with 30% acetic acid. The elution rate was 100 ml/hr. Fractions containing cryptdins were identified by electrophoresis in acid-urea polyacrylamide gels (Selsted and Harwig, Infect. Immun. 55:2281–2285 (1987), which is incorporated herein by reference).

Cryptdin-containing fractions were pooled and lyophilized, then purification was completed by RP-HPLC. Initial separation of mouse cryptdins 2–5 was achieved by HPLC on a 1×25 cm Vydac C-18 column using a gradient of water and acetonitrile containing 0.13% HFBA. Solvents were delivered at 3 ml/min to generate the following acetonitrile gradient: 0–28% (10 min); 28–34% (20 min); and 34–40% (60 min). Cryptdins 1 and 6, which coeluted under these conditions, were resolved by C-18 RP-HPLC using 0.1% TFA as the ion pair and a 16–21% acetonitrile gradient delivered in 35 min at 3 ml/min. To eliminate traces of residual HFBA, preparations of cryptdins 2–5 were subjected to an addition RP-HPLC step using 0.1% TFA. All peptides were lyophilized and quantitated by amino acid analysis prior to antimicrobial testing. Essentially identical methods were used to purify rat and human cryptdin peptides, except that rat cryptdins were isolated from the small intestine of adult Sprague-Dawley rats and human cryptdins were isolated from a surgically resected normal adult human male small intestine.

EXAMPLE II

Peptide Characterization

Amino acid analyses were performed on 6 N HCl hydrolysates (150° C., 2 hr) of unmodified or performic acid-oxidized peptides. Hydrolysates were derivatized with phenylisothiocyanate and the resulting phenylthiocarbamyl amino acids were quantitated as described previously (Selsted and Harwig, supra, 1987; Selsted et al., supra, 1992; Ouellette et al., FEBS Lett. 304:146–148 (1992), which is incorporated herein by reference). Peptide samples were reduced with dithiothreitol (DTT) and pyridylethylated with 4-vinyl pyridine for sequencing (Henschen, In Advanced Methods in Protein Microsequence Analysis (Wittmann-Liebold et al., pages 244–255 (1986), which is incorporated herein by reference). Sequence determinations were performed by automated Edman degradation on an ABI model 477 system (Applied Biosystems, Inc.; Foster City, Calif.) with on-line PTH amino acid analysis. In some cases, the C-terminus of a cryptdin peptide was confirmed by amino acid analysis of chymotryptic peptides. Cryptdins 4 and 5 also were analyzed by positive-ion fast atom bombardment mass spectrometry on a VG 7070E-HF instrument (Ouellette et al., supra, 1994).

EXAMPLE III

Antimicrobial Assays

Antibacterial activity was measured in an agar radial diffusion assay (Lehrer et al., supra, 1991b) using wild type S. typhimurium (ATCC 10428) or an isogenic phoP mutant of S. typhimurium (strain CS015 phoP102::Tn10d-Cam, Miller et al., supra, 1989). Cells were grown to log phase in trypticase soy broth at 37° C., harvested by centrifugation and resuspended to $1 \times 10^7$ colony forming units (CFU) per ml in 10 mM sodium phosphate buffer (pH 7.4).

A 100 μl aliquot of each organism was mixed with 10 ml 1% agarose in 0.03% (w/v) trypticase soy medium, 10 mM sodium phosphate (pH 7.4) at 42° C. Five μl samples of peptide solution were pipetted into 3 mm diameter wells formed in the agarose with a sterile punch. After 3 hr at 37° C., the inoculated agarose plate was overlayed with 1% agarose containing 6% trypticase soy medium. After 12–16 hr, antimicrobial activity was apparent as clear zones surrounding wells loaded with antibacterial samples; the sizes of the clear zones were concentration-dependent.

Cryptdin antimicrobial activity in vitro was substantially enhanced in piperazine-N,N'-bis (2-ethane sulfonic acid) (PIPES) or in N-2-hydroxyethylpiperazine-N'-2-ethanesulfonic acid (HEPES) as compared to the activity in sodium phosphate. Purified cryptdin peptides were dissolved at 3 to 300 μg/ml in 0.01% acetic acid and activity was examined against E. coli ML35 (ATCC). In the radial diffusion assay, 5 μl peptide solution was transferred into wells formed in plates of 1% agarose buffered with 10 mM PIPES (pH 7.4) and containing 1×106 log-phase bacteria grown in trypticase soy broth. After 3 hr at 37° C., the plates were overlayed with 0.8% agarose containing 2× trypticase soy broth and incubated overnight. The antibacterial activities of cryptdin peptides was compared with the activity of rabbit neutrophil defensin NP-1, which was purified from peritoneal exudates as described by Selsted et al. (J. Biol. Chem. 260:4579–4584 (1985), which is incorporated herein by reference). Antibacterial activity was determined by measuring the diameter of clearing around each well and plotted as a function of peptide concentration.

As shown in FIG. 12, each cryptdin peptide produced a dose-dependent zone of clearing, which indicates that E. coli growth was inhibited. The potencies of the cryptdins varied, with cryptdins 1, 3 and 6 showing similar activity, which was about 3–5× greater than the activity of cryptdin 2. Cryptdin 5 was approximately 5× more active than rabbit NP-1 at concentration above 100 μg/ml (FIG. 12.C.) and cryptdin 4 was at least 50x more active than NP-1 when compared at 100 μg/ml and 300 μg/ml (FIG. 12.B.). These higher concentrations of cryptdins 4 and 5 also were more effective than the same concentration of NP-1 at inhibiting the growth of S. aureus and of wild type and mutant strains of S. typhimurium (not shown). These results demonstrate that various cryptdin peptides can inhibit bacterial growth.

In order to determine whether the effect of the cryptdin peptides against E. coli is bacteriostatic or bacteriocidal, bacterial killing was quantitated as a function of time. Bactericidal assays were performed by incubating $1-2 \times 10^6$ log-phase bacteria in 10 mM PIPES containing 10 μg peptide/ml. After incubation for 15 or 30 min at 37° C., aliquots were removed, serially diluted and plated on trypticase soy agar. Bactericidal activity was quantitated by counting colonies after overnight incubation at 37° C.

As shown in FIG. 13, cryptdins 1 and 3–6 rapidly killed the E. coli cells. In each of these cases, survival was reduced to less than 1% after only 15 min incubation. Cryptdin 2 was the only peptide tested that was not bactericidal under the assay condition. Cryptdins 2 and 3 differ only at amino acid position 10 (threonine and lysine, respectively).

The bactericidal activity of rat cryptdin 1 also was examined. E. coli ML35 cells, S. aureus 502A cells or mutant or wild type *S. typhimurium* cells were incubated with various concentrations of rat cryptdin 1 or rabbit NP-1. Ten μg/ml rat cryptdin 1 killed about 90% of the *S. aureus* cells and greater than 99% of the *E. coli* and mutant *S. typhimurium* cells, but was relatively ineffective in killing wild type *S. typhimurium* (not shown). Rat cryptdin 1 was more effective than NP-1 in killing the *E. coli* and mutant *S. typhimurium* cells, whereas NP-1 was more effective in killing *S. aureus*.

The effect of mouse cryptdins 1–3 and 6 at inhibiting the growth of the protozoan, *Giardia lamblia*, which is the most common cause of protozoan disease in the human small intestine, also was examined. Briefly, trophozoites of the C6 clone of *Giardia lamblia* WB (ATCC 30957) were grown to late log phase in TYI-S-33 medium containing bovine bile. Free-swimming trophozoites were discarded and tubes with attached trophozoites were refilled with warm Dulbecco's PBS. Trophozoites were detached by chilling 10 min on ice, then harvested by centrifugation, resuspended at $2 \times 10^7$/ml in 25 mM HEPES (pH 7.5) containing 9% (isotonic) sucrose and incubated for 2 hr at 37° C. with various concentrations of mouse cryptdins 1–3 or 6. Following incubation, trophozoite viability was determined by trypan blue exclusion.

The cryptdin peptides killed Giardia trophozoites in a dose-dependent manner (not shown). In particular, 20 μg/ml of cryptdin 2 or cryptdin 3 reduced Giardia growth by greater than 2 orders of magnitude (not shown). These results indicate that cryptdins are active against a variety of microorganisms.

EXAMPLE IV

Anti-cryptdin Antibody

A polyclonal rabbit antibody was prepared to a synthetic analogue of cryptdin 1. The peptide, termed cryptdin C, corresponding to residues 4–35 in cryptdin 1 (SEQ ID NO: 6; FIG. 1) was synthesized by solid phase chemistry using $N^\alpha$-butoxycarbonyl protection (Kent, *Ann. Rev. Biochem.* 57:957–989 (1988), which is incorporated herein by reference). Following cleavage/deprotection of synthetic cryptdin C with TFA-trifluoromethanesulfonic acid, the peptide was precipitated in ethyl ether and dried in vacuo. A 100 mg sample was dissolved in 10 ml 6.0 M guanidine-HCl, 0.2 M Tris-HCl, pH 8.2, containing 20 mg DTT. The sample was purged with nitrogen, heated to 50 ° C. for 4 hr and diluted 100-fold with deionized water, then was dialyzed exhaustively, first against 0.1 M sodium phosphate (pH 8.2), 20 mM guanidine-HCl, 100 mM NaCl, then against 5% acetic acid. The sample was lyophilized, dissolved in 10 ml 5% acetic acid and subjected to RP-HPLC on a 1×25 cm Vydac C-18 column. The earliest eluting peak, representing about 0.5% of the crude peptide, was determined by amino acid analysis to have the desired composition.

A sample (1.5 mg) of cryptdin C was supplied, without conjugation to carrier, to Berkeley Antibody Company (Berkeley, Cailf.) for immunization of 2 New Zealand White rabbits. Serum samples were collected for 12 weeks, until the anti-cryptdin C titer, determined by ELISA, reached about 1:10,000 for each rabbit. IgG was isolated from antiserum using DEAE Econo-Pac chromatography (Bio-Rad; Richmond Cailf.) as described by the manufacturer.

EXAMPLE V

Immunohistochemistry

Paraffin sections of formalin-fixed mouse mid-small bowel were deparaffinized, treated with 1.1% hydrogen peroxide for 40 min, then washed extensively with water followed by PBS. Slides were treated for 20 min at 37° C. with 500 μg/ml trypsin in PBS, washed twice with PBS, and blocked by incubation for 20 min with 5% porcine serum. Slides were incubated for 20 min in rabbit anti-cryptdin IgG (1:10 dilution relative to serum IgG concentration), then washed with blocking serum. Porcine anti-rabbit IgG was used as linking reagent between the primary antibody and rabbit antiperoxidase-peroxidase conjugate (Dako; Carpinteria Calif.). Diaminobenzidine was used as peroxidase substrate and parallel incubations were performed using equivalent dilutions of rabbit preimmune IgG as the primary antibody.

EXAMPLE VI

Preparation of Synthetic Cryptdin 1

This example provides a method for synthesizing, purifying and characterizing synthetic cryptdin 1.

A. Synthesis

Synthesis was initiated at the 0.13 mmole scale using Wang resin coupled to flourenylmethoxycarbonyl (Fmoc)-arginine using an acid labile linker. Synthesis was carried out in dimethylformamide (DMF) using (relative to resin substitution) a 3-fold excess of Fmoc-amino acids activated in situ with a 3-fold excess of BOP (benzotriazol-1-yl-oxytris (dimethylamino) phosphonium hexafluorophosphate) and HOBt (hydroxybenzotriazole) and a 6-fold molar excess of N-methylmorpholine (Nmmi). Fmoc removal during synthetic cycles was achieved using cycles of 50% and 25% piperidine in DMF. The side-chain protection scheme utilized the following Fmoc-amino acids: OtBut-aspartic acid, Pmc-arginine, tBut-tyrosine, tBut-serine, Trt-cysteine, tBoc-lysine, OtBut-glutamic acid, Trt-asparagine, tBut-threonine and Trt-histidine.

The peptide chain was assembled in a Synostat batch synthesizer using single couplings at all additions except at leucine and valine which were double coupled. The cycle sequence is as follows:

1. Wash with DMF 4× for 2 min;
2. Deblock: 50% piperidine 1× for 5 min;
3. Deblock: 25% piperidine 1× for 15 min;
4. Wash with DMF 4× for 2 min;
5. Dissolve amino acids + BOP + HOBt in DMF and transfer to reaction vessel;
6. Add Nmm to RV and mix for 60 min; and
7. Wash with DMF 1× for 2 min.

After coupling of the amino terminal residue, the terminal Fmoc group was removed using the following cycle:

1. Wash with DMF 4× for 2 min;
2. Deblock: 50% piperidine 1× for 5 min;
3. Deblock: 25% piperidine 1× for 15 min;
4. Wash with DMF 4× for 2 min;
5. Wash with dichloromethane 1× for 5 min;
6. Wash with isopropanol 4× for 5 min;
7. Dry under stream of $N_2$ 1× for 10–20 min; and
8. Dry under vacuum 1× for 12 hr.

The peptide-resin was weighed to determine mass increase. To cleave and deprotect the peptide-resin, it was first reswelled in dichloromethane, then cleaved and deprotected by addition of reagent R (90% trifluoroacetic acid, 5% thioanisole, 3% ethanedithiol, 2% anisole) at a ratio of 10 ml/g peptide-resin. Cleavage/deprotection was carried out under nitrogen for 18 hr at RT.

B. Purification

The cleavage mixture was separated from resin by filtration through a scintered glass funnel, washed with 1–2 ml fresh reagent R and diluted 5-fold with 50% acetic acid. Glacial acetic acid was added to a final acetic acid concentration of 50%. The resulting solution was extracted 3× with 0.33 vol methylene chloride and the aqueous phase was lyophilized to dryness, then dissolved in 50% acetic acid and relyophilized. The extraction and lyophilization steps were repeated 3–4 times, then the dry peptide was dissolved in 30% acetic acid at a concentration of 20 mg/ml and passed over an 800 ml Sephadex G-10 column equilibrated in 30% acetic acid. Peptide-containing fractions were pooled, lyophilized, dissolved in 5% acetic acid, then diluted ten-fold with water to a final protein concentration of about 1 mg/ml. The solution was adjusted to pH 8.0 with ammonium hydroxide and mixed rapidly with a magnetic stirrer at RT in a beaker open to room air. The pH was adjusted periodically to pH 8.0 over a period of 4 days. The solution was then acidified with acetic acid to pH 3.5 and lyophilized.

C-18 RP-HPLC using 0.1% TFA-water/acetonitrile gradients was used to purify the folded peptide. Fractions were analyzed on acid-urea gels and compared to natural cryptdin 1. The yield from an initial crude peptide preparation of 500 mg was approximately 30 mg.

C. Characterization

Synthetic cryptdin 1 was compared to natural peptide on analytical RP-HPLC, SDS-PAGE and under three different conditions on acid-urea PAGE. For analysis on acid-urea PAGE, peptide was electrophoresed either without modification, after reduction with DTT or after performic acid oxidation. Under all conditions described, native and synthetic cryptdin 1 behaved identically. The amino acid compositions of natural and synthetic cryptdin 1 were indistinguishable.

EXAMPLE VII

Cloning of Nucleic Acid Molecules Encoding Cryptdins

Individual crypts were isolated using a modification of the EDTA elution method of Bjerknes and Cheng, supra, 1981, as described by Cano-Gauci et al., *Expt. Cell Res.* 208:344–349 (1993), which is incorporated herein by reference. Briefly, the central 10 cm of small intestine from an adult C3H/HeJ mouse was everted on a Buchler gradient-making apparatus, then intact crypts were dislodged by vibration in ice cold 30 mM EDTA in calcium-free, magnesium-free PBS. Isolated crypts were disrupted in a sonicating water bath prior to cDNA synthesis.

The crypt library was constructed by mRNA-directed PCR amplification (Cano-Gauci et al., supra, 1992). Phage were screened at a density of approximately 300 PFU/dish using the partial cDNA clone, asb4/134, as a probe (Ouellette et al., supra, 1989a). Positive phage were collected and denatured plasmid cDNA was sequenced by the dideoxynucleotide termination method using Sequenase™ (U.S. Biochemical Corp.; Cleveland Ohio). Sequencing primers included T3 and T7 promoter primers and Defcr$_{p130}$, which is a 16-mer that corresponds to nucleotides 90–105 in cryptdin 1 mRNA (Huttner et al., *Genomics* 19: 448–453 (1994), which is incorporated herein by reference). Reaction mixtures were separated by electrophoresis in gels consisting of 5% Long Ranger™ (AT Biochem, Inc.; Malvern Pa.) and DNA sequence data were analyzed (Ouellette et al., supra, 1994). Computations for similarity searches of DNA sequences in nonredundant nucleic acid and protein sequence databases were performed at the National Center for Biotechnology Information with the BLAST network service (Ouellette et al., supra, 1994).

A cDNA library also was prepared by amplification of cryptdin mRNA (Huttner et al., supra, 1994). Total RNA was isolated from the small intestine of a male 129/SVJ mouse using RNazol™ (Biotecx Lab; Houston, Tex.). First strand cDNA synthesis was performed using the cDNA Cycle Kit (Invitrogen; San Diego CA). Amplification of 5' ends was performed using the 5' RACE method (Frohman et al., *Proc. Natl. Acad. Sci., USA* 85:8998–9002 (1988), which is incorporated herein by reference) with a reverse primer that was specific for a conserved region of the cryptdin 3'-untranslated sequence (UTS).

Blot hybridization of the PCR products using an oligonucleotide probe specific for the cryptdin prepro-coding region detected a single band. DNA from the band was isolated using the Geneclean II™ kit (Biolbl; La Jolla Calif.), subcloned into the Bluescript II plasmid using the pCR-Script SK(+) cloning kit (Stratagene) and transfected into competent XL-1 Blue cells (Stratagene). Colonies containing cryptdin-related sequences were identified by hybridization to a labelled asb4/134 probe. DNA sequence analysis of the positive clones was performed as described above, except that internal primers were utilized as required.

Using these methods, cDNA sequences encoding 17 distinct mouse cryptdin peptides were identified (FIG. 10; SEQ ID NOS: 40–56). The various mouse cryptdin cDNA sequences share 93–100% nucleotide sequence identity with cryptdin 1, except cryptdin 5 and cryptdin 4 share 73% and 69% sequence identity, respectively, with cryptdin 1.

The amino acid sequences were deduced from the cDNA sequences for the 17 mouse cryptdins (see FIG. 9.A.; SEQ ID NOS: 23 to 39). As shown in FIG. 9.A., the cDNA sequences encode prepro-cryptdin peptides consisting of a signal peptide, a propiece and the cryptdin peptide. The prepro-cryptdins, including the mature cryptdin peptide, share significant amino acid sequence identity with cryptdin 1, although cryptdins 4 and 5 are less homologous (FIG. 9.B.). Amino acid variability was most striking at position 10 of the mature cryptdin peptide, where either serine, threonine, alanine, isoleucine or lysine can be found. Interestingly, a single nucleotide change in the sequence of cryptdin 2 can account for each of these amino acids. In addition, position 15 can contain arginine or lysine. The amino acid variability among cryptdin peptides can be involved in conferring different antimicrobial properties to the cryptdins.

Mouse cryptdin genomic clones also were obtained and sequenced (Huttner et al., supra, 1994). Asb4/134 was used as a probe to screen a custom-made 129/SVJ mouse genomic library constructed in lambda DASH II (Stratagene Cloning Systems, Inc.; La Jolla Calif.). Approximately 1×10$^6$ phage were screened in duplicate and 25 positive phage were identified. Ten clones were purified and phage DNA was isolated using Qiagen 100 columns (Qiagen, Inc.; Chatsworth Calif.). Southern blots of Eco RI-digested DNA from individual phage were hybridized to asb4/134 and hybridizing fragments were subcloned into Bluescript II SK$^+$™ (Stratagene) or pUC18 (BRL; Gaithersburg Md.) for sequencing.

Sequencing was performed as described above, except that primers were selected based on the cryptdin 1 cDNA sequence and with the expectation that mouse cryptdin genes would be structurally homologous to the rabbit MCP-1 and MCP-2 defensin genes (see Huttner et al., supra, 1994). DNA sequence data were analyzed using the programs of Staden (*Biochem. Soc. Trans.* 12:1005–1008 (1984) and the University of Wisconsin Genetics Computer Group (Devereux et al., *Nucl. Acids Res.* 12:387–395 (1985)). Searches for homology were performed as described above.

As shown in FIG. 11, screening of the genomic library produced nucleic acid sequences that contained the complete coding sequences for mouse cryptdins 1, 2, 3, 5 and 6 (SEQ ID NOS: 58–62). In addition, a homologous gene, designated cryptdin i (Crypi; SEQ ID NO: 63), which apparently was inactivated due to a point mutation that changed a cysteine codon to an in-frame stop codon, was isolated. Examination of the nucleic acid sequences revealed that the cryptdin genes contain two exons, the first of which codes for the 5'-UTS and the prepro-coding region and the second of which encodes the mature cryptdin peptide and the 3'-UTS (not shown; but see FIG. 11.A.).

A similar structure has been described for the human cryptdin genes (Jones and Bevins, *J. Biol. Chem.* 267:23216–23225 (1992)).

Similar methods as described above were used to obtain the cDNA sequences encoding rat cryptdins 1–3 (FIGS. 14.A. to 14.C.; SEQ ID NOS: 65–67, respectively), except that RNA was obtained from the small intestine of Sprague-Dawley rats. In addition, genomic DNA sequences encoding rat cryptdins 1–3 (FIGS. 15.A. to 15.C.; SEQ ID NOS: 68–70, respectively) were obtained using methods as described above, except that a genomic library containing Sprague-Dawley DNA cloned in EMBL3 was purchased from Clontech (Palo Alto Cailf.).

Although the invention has been described with reference to the disclosed embodiments, it should be understood that various modifications can be made without departing from the spirit of the invention. Accordingly, the invention is limited only by the following claims.

We claim:

1. A method for detecting an inflammatory pathology in a subject's intestine, comprising the steps of:
   a) determining an amount of cryptdin in a sample obtained from the subject's intestine; and
   b) comparing said amount of cryptdin to an amount of cryptdin in a normal subject, wherein a deviation of at least one standard deviation from said amount of cryptdin in a normal subject is indicative of an inflammatory pathology in said subject's intestine,
said cryptdin having an amino acid sequence as follows:

$X_1$-C-$X_2$-C-R-$X_3$-C-$X_4$-E-$X_5$-C-$X_6$-C-C-$X_7$ wherein
$X_1$ is 3 to 9 amino acids;
$X_2$ is 1 amino acid;
$X_3$ is 2 or 3 amino acids;
$X_4$ is 3 amino acids;
$X_5$ is 5 amino acids;
$X_6$ is 6 to 10 amino acids; and
$X_7$ is 0 to 9 amino acids.

2. The method of claim 1, wherein the amount of cryptdin in said sample is determined by contacting said sample with an anti-cryptdin antibody and detecting specific binding of said anti-cryptdin antibody to cryptdin in said sample.

3. The method of claim 1, wherein said sample is selected from the group consisting of intestinal tissue and intestinal lavage.

4. The method of claim 1, wherein said inflammatory pathology in a subject's intestine is selected from the group consisting of inflammatory bowel disease, pancreatitis, malignancy, infection and ileitis.

5. An anti-cryptdin antibody, which specifically binds a cryptdin having an amino acid sequence as follows:

$X_1$-C-$X_2$-C-R-$X_3$-C-$X_4$-E-$X_5$-C-$X_6$-C-C-$X_7$ wherein $X_1$ is 3 to 9 amino acids;
$X_2$ is 1 amino acid;
$X_3$ is 2 or 3 amino acids;
$X_4$ is 3 amino acids;
$X_5$ is 5 amino acids;
$X_6$ is 6 to 10 amino acids; and
$X_7$ is 0 to 9 amino acids.

6. The anti-cryptdin antibody of claim 5, wherein said antibody is a monoclonal antibody.

* * * * *

UNITED STATES PATENT AND TRADEMARK OFFICE
CERTIFICATE OF CORRECTION

PATENT NO. : 5,840,498
DATED : November 24, 1998
INVENTOR(S) : Selsted et al.

It is certified that error appears in the above-identified patent and that said Letters Patent is hereby corrected as shown below:

Column 8,
Line 48, please delete "consistent 10" and replace with -- consistent --.

Column 12,
Line 26, please delete "be 25" and replace with -- be --.

Column 14,
Line 25, please delete "1x106" and replace with -- $1x10^6$ --.

Column 16,
Line 29, please delete "(Nmmi)." and replace with -- (Nmm). --.

Column 18,
Line 18, please delete "(Biolbl;" and replace with -- Bio101; --.

Signed and Sealed this

Twenty-ninth Day of June, 2004

JON W. DUDAS
*Acting Director of the United States Patent and Trademark Office*